United States Patent
Pal et al.

(10) Patent No.: US 9,233,244 B2
(45) Date of Patent: *Jan. 12, 2016

(54) TRANSDERMAL ELECTRICAL STIMULATION DEVICES FOR MODIFYING OR INDUCING COGNITIVE STATE

(71) Applicant: thync, inc., Los Gatos, CA (US)

(72) Inventors: Sumon K. Pal, Boston, MA (US); Jonathan Charlesworth, Boston, MA (US); Remi Demers, Saint-Nicolas (CA); Daniel Z. Wetmore, San Francisco, CA (US); Isy Goldwasser, Los Gatos, CA (US); William J. Tyler, Newton, MA (US); Raymond L. Gradwohl, Saratoga, CA (US); Philip Lamb, San Diego, CA (US); Christopher Voss, Dorval (CA)

(73) Assignee: thync, inc., Los Gatos, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/639,015

(22) Filed: Mar. 4, 2015

(65) Prior Publication Data
US 2015/0174403 A1      Jun. 25, 2015

Related U.S. Application Data

(63) Continuation of application No. 14/320,461, filed on Jun. 30, 2014, now Pat. No. 9,002,458.

(60) Provisional application No. 61/845,845, filed on Jul. 12, 2013, provisional application No. 61/875,424, (Continued)

(51) Int. Cl.
*A61N 1/18*      (2006.01)
*A61N 1/36*      (2006.01)
*A61N 1/04*      (2006.01)

(52) U.S. Cl.
CPC .......... *A61N 1/36025* (2013.01); *A61N 1/0456* (2013.01); *A61N 1/0476* (2013.01); *A61N 1/36014* (2013.01); *A61N 1/0484* (2013.01); *A61N 1/0492* (2013.01)

(58) Field of Classification Search
None
See application file for complete search history.

(56) References Cited

U.S. PATENT DOCUMENTS

| | | |
|---|---|---|
| 4,431,000 A | 2/1984 | Butler et al. |
| 4,503,861 A | 3/1985 | Entrekin |

(Continued)

FOREIGN PATENT DOCUMENTS

| | | |
|---|---|---|
| EP | 502919 B1 | 11/1993 |
| EP | 801957 A1 | 10/1997 |

(Continued)

OTHER PUBLICATIONS

Pal et al.; U.S. Appl. No. 14/634,551 entitled "Methods for user control of neurostimulation to modify a cognitive state," filed Feb. 27, 2015.

(Continued)

*Primary Examiner* — Brian T Gedeon
*Assistant Examiner* — Ankit Tejani
(74) *Attorney, Agent, or Firm* — Shay Glenn LLP

(57) ABSTRACT

Portable transdermal electrical stimulation (TES) applicators for modifying a subject's cognitive state. In general, the portable applicators described are specifically configured and adapted to be lightweight and may be wearable, and to deliver a high-intensity TES able to evoke or enhance a predetermined cognitive effect. These TES applicators may include a pair of electrodes and a TES control module comprising a processor, a timer and a waveform generator. TES control module is adapted to deliver a biphasic electrical stimulation signal of 10 seconds or longer between the first and second electrodes having a frequency of 400 Hz or greater, a duty cycle of greater than 10 percent, an intensity of 3 mA or greater, with a DC offset.

28 Claims, 32 Drawing Sheets

Related U.S. Application Data filed on Sep. 9, 2013, provisional application No. 61/841,308, filed on Jun. 29, 2013, provisional application No. 61/907,394, filed on Nov. 22, 2013, provisional application No. 61/888,910, filed on Oct. 9, 2013, provisional application No. 61/975,118, filed on Apr. 4, 2014, provisional application No. 62/002,860, filed on May 25, 2014, provisional application No. 62/002,909, filed on May 25, 2014, provisional application No. 62/002,910, filed on May 25, 2014.

(56) References Cited

U.S. PATENT DOCUMENTS

| | | |
|---|---|---|
| 4,638,436 A | 1/1987 | Badger et al. |
| 4,646,744 A | 3/1987 | Capel |
| 4,664,117 A | 5/1987 | Beck |
| 5,144,952 A | 9/1992 | Frachet et al. |
| 5,183,041 A | 2/1993 | Toriu et al. |
| 5,342,410 A | 8/1994 | Braverman |
| 5,397,338 A | 3/1995 | Grey et al. |
| 5,476,481 A | 12/1995 | Schondorf |
| 5,487,759 A | 1/1996 | Bastyr et al. |
| 5,514,175 A | 5/1996 | Kim et al. |
| 5,522,878 A | 6/1996 | Montecalvo et al. |
| 5,540,736 A | 7/1996 | Haimovich et al. |
| 5,573,552 A | 11/1996 | Hansjurgens |
| 5,578,065 A | 11/1996 | Hattori et al. |
| 5,593,427 A | 1/1997 | Gliner et al. |
| 5,655,539 A | 8/1997 | Wang et al. |
| 6,324,432 B1 | 11/2001 | Rigaux et al. |
| 6,445,955 B1 | 9/2002 | Michelson et al. |
| 6,463,328 B1 | 10/2002 | John |
| 6,526,318 B1 | 2/2003 | Ansarinia |
| 6,567,702 B1 | 5/2003 | Nekhendzy et al. |
| 6,623,430 B1 | 9/2003 | Slayton et al. |
| 6,983,184 B2 | 1/2006 | Price |
| 7,120,499 B2 | 10/2006 | Thrope et al. |
| 7,146,217 B2 | 12/2006 | Firlik et al. |
| 7,283,861 B2 | 10/2007 | Bystritsky |
| 7,376,467 B2 | 5/2008 | Thrope et al. |
| 7,422,555 B2 | 9/2008 | Zabara |
| 7,577,481 B2 | 8/2009 | Firlik et al. |
| 7,660,636 B2 | 2/2010 | Castel et al. |
| 7,891,615 B2 | 2/2011 | Bevirt |
| 7,949,403 B2 | 5/2011 | Palermo et al. |
| 8,086,318 B2 | 12/2011 | Strother et al. |
| 8,097,926 B2 | 1/2012 | De Graff et al. |
| 8,121,695 B2 | 2/2012 | Gliner et al. |
| 8,150,537 B2 | 4/2012 | Tanaka et al. |
| 8,190,248 B2 | 5/2012 | Besio et al. |
| 8,204,601 B2 | 6/2012 | Moyer et al. |
| 8,239,030 B1 | 8/2012 | Hagedorn et al. |
| 8,265,761 B2 | 9/2012 | Siever |
| 8,280,502 B2 | 10/2012 | Hargrove et al. |
| 8,380,315 B2 | 2/2013 | DeGiorgio et al. |
| 8,428,738 B2 | 4/2013 | Valencia |
| 8,494,627 B2 | 7/2013 | Bikson et al. |
| 8,506,469 B2 | 8/2013 | Dietrich et al. |
| 8,560,075 B2 | 10/2013 | Covalin |
| 8,639,343 B2 | 1/2014 | De Vos |
| 8,688,239 B2 | 4/2014 | Hartlep et al. |
| 8,843,210 B2 | 9/2014 | Simon et al. |
| 8,903,494 B2 | 12/2014 | Goldwasser et al. |
| 9,002,458 B2 | 4/2015 | Pal et al. |
| 9,014,811 B2 | 4/2015 | Pal et al. |
| 2002/0116036 A1 | 8/2002 | Daignault et al. |
| 2003/0060736 A1 | 3/2003 | Martin et al. |
| 2003/0225323 A1 | 12/2003 | Kiani et al. |
| 2004/0015079 A1 | 1/2004 | Berger et al. |
| 2004/0098065 A1 | 5/2004 | Hagglof et al. |
| 2004/0267333 A1 | 12/2004 | Kronberg |
| 2005/0143677 A1 | 6/2005 | Young et al. |
| 2005/0165460 A1 | 7/2005 | Erfan |
| 2005/0267388 A1 | 12/2005 | Hanna |
| 2007/0088419 A1 | 4/2007 | Fiorina et al. |
| 2007/0173890 A1 | 7/2007 | Armstrong |
| 2007/0213790 A1 | 9/2007 | Nolan et al. |
| 2007/0276451 A1 | 11/2007 | Rigaux |
| 2007/0299370 A1 | 12/2007 | Bystritsky |
| 2008/0045882 A1 | 2/2008 | Finsterwald |
| 2008/0132974 A1 | 6/2008 | Strother et al. |
| 2008/0194965 A1 | 8/2008 | Sliwa et al. |
| 2008/0208266 A1 | 8/2008 | Lesser et al. |
| 2008/0215113 A1 | 9/2008 | Pawlowicz |
| 2008/0319505 A1 | 12/2008 | Boyden et al. |
| 2009/0048642 A1 | 2/2009 | Goroszeniuk |
| 2009/0099623 A1 | 4/2009 | Bentwich |
| 2009/0112098 A1 | 4/2009 | Vaezy et al. |
| 2009/0112133 A1 | 4/2009 | Deisseroth et al. |
| 2009/0112280 A1 * | 4/2009 | Wingeier et al. ............... 607/45 |
| 2009/0177243 A1 | 7/2009 | Lebedev et al. |
| 2009/0210028 A1 | 8/2009 | Rigaux et al. |
| 2009/0270947 A1 | 10/2009 | Stone et al. |
| 2009/0287108 A1 | 11/2009 | Levy |
| 2010/0049264 A1 | 2/2010 | Henke et al. |
| 2010/0057154 A1 | 3/2010 | Dietrich et al. |
| 2010/0145399 A1 | 6/2010 | Johari et al. |
| 2010/0256436 A1 | 10/2010 | Partsch et al. |
| 2010/0298623 A1 | 11/2010 | Mishelevich et al. |
| 2011/0029038 A1 | 2/2011 | Hyde et al. |
| 2011/0082326 A1 | 4/2011 | Mishelevich et al. |
| 2011/0082515 A1 | 4/2011 | Libbus et al. |
| 2011/0092800 A1 | 4/2011 | Yoo et al. |
| 2011/0093033 A1 | 4/2011 | Nekhendzy |
| 2011/0112394 A1 | 5/2011 | Mishelevich |
| 2011/0114191 A1 | 5/2011 | Wheater et al. |
| 2011/0130615 A1 | 6/2011 | Mishelevich |
| 2011/0137381 A1 | 6/2011 | Lee et al. |
| 2011/0144716 A1 | 6/2011 | Bikson et al. |
| 2011/0160811 A1 * | 6/2011 | Walker ............... 607/72 |
| 2011/0178441 A1 | 7/2011 | Tyler |
| 2011/0178442 A1 | 7/2011 | Mishelevich |
| 2011/0190668 A1 | 8/2011 | Mishelevich |
| 2011/0190846 A1 | 8/2011 | Ruffini et al. |
| 2011/0196267 A1 | 8/2011 | Mishelevich |
| 2011/0208094 A1 | 8/2011 | Mishelevich |
| 2011/0213200 A1 | 9/2011 | Mishelevich |
| 2011/0230701 A1 | 9/2011 | Simon et al. |
| 2011/0230702 A1 | 9/2011 | Honour |
| 2011/0230938 A1 | 9/2011 | Simon et al. |
| 2011/0270138 A1 | 11/2011 | Mishelevich |
| 2011/0270345 A1 | 11/2011 | Johnston et al. |
| 2011/0276112 A1 | 11/2011 | Simon et al. |
| 2011/0288610 A1 | 11/2011 | Brocke |
| 2012/0016431 A1 | 1/2012 | Paul et al. |
| 2012/0029591 A1 | 2/2012 | Simon et al. |
| 2012/0029601 A1 | 2/2012 | Simon et al. |
| 2012/0046531 A1 | 2/2012 | Hua |
| 2012/0101366 A1 | 4/2012 | Ruohonen et al. |
| 2012/0109251 A1 | 5/2012 | Lebedev et al. |
| 2012/0149973 A1 | 6/2012 | Holloway |
| 2012/0165759 A1 | 6/2012 | Rogers et al. |
| 2012/0185020 A1 | 7/2012 | Simon et al. |
| 2012/0209346 A1 | 8/2012 | Bikson et al. |
| 2012/0245653 A1 | 9/2012 | Bikson et al. |
| 2012/0283502 A1 | 11/2012 | Mishelevich et al. |
| 2012/0302912 A1 | 11/2012 | Moffitt et al. |
| 2013/0035734 A1 | 2/2013 | Soler et al. |
| 2013/0041235 A1 | 2/2013 | Rogers et al. |
| 2013/0060304 A1 | 3/2013 | La Tendresse et al. |
| 2013/0066395 A1 | 3/2013 | Simon et al. |
| 2013/0079659 A1 | 3/2013 | Akhadov et al. |
| 2013/0158627 A1 | 6/2013 | Gozani et al. |
| 2013/0184779 A1 | 7/2013 | Bikson et al. |
| 2013/0197401 A1 | 8/2013 | Sato et al. |
| 2013/0204315 A1 | 8/2013 | Wongsarnpigoon et al. |
| 2013/0267761 A1 | 10/2013 | Bentwich |
| 2013/0282095 A1 | 10/2013 | Mignolet et al. |

(56) References Cited

U.S. PATENT DOCUMENTS

| | | |
|---|---|---|
| 2014/0277324 A1 | 9/2014 | DiUbaldi et al. |
| 2015/0088224 A1 | 3/2015 | Goldwasser et al. |

FOREIGN PATENT DOCUMENTS

| | | |
|---|---|---|
| EP | 1502623 B1 | 11/2007 |
| EP | 1551290 B1 | 8/2008 |
| EP | 2024018 A2 | 2/2009 |
| EP | 2314346 A1 | 4/2011 |
| EP | 1559369 B1 | 3/2012 |
| EP | 2069001 B1 | 2/2013 |
| WO | WO92/06737 A1 | 4/1992 |
| WO | WO93/17628 A1 | 9/1993 |
| WO | WO94/00188 A1 | 1/1994 |
| WO | WO94/00189 A1 | 1/1994 |
| WO | WO01/78834 A1 | 10/2001 |
| WO | WO03/105945 A2 | 12/2003 |
| WO | WO2006/113801 A2 | 10/2006 |
| WO | WO2006/138702 A2 | 12/2006 |
| WO | WO2008/155114 A1 | 12/2008 |
| WO | WO2009/089014 A1 | 7/2009 |
| WO | WO2009/137683 A2 | 11/2009 |
| WO | WO2010/047834 A1 | 4/2010 |
| WO | WO2010/067145 A1 | 6/2010 |
| WO | WO2011/057028 A1 | 5/2011 |
| WO | WO2011/147546 A1 | 12/2011 |
| WO | WO2012/082960 A2 | 6/2012 |
| WO | WO2012/089588 A1 | 7/2012 |
| WO | WO 2012/116407 A1 | 9/2012 |
| WO | WO2012/129574 A2 | 9/2012 |
| WO | WO2012/150600 A2 | 11/2012 |
| WO | WO2012/156052 A2 | 11/2012 |
| WO | WO2013/071307 A1 | 5/2013 |

OTHER PUBLICATIONS

Jeffery et al.; U.S. Appl. No. 14/634,664 entitled; "Cantilever electrodes for transdermal and transcranial stimulation," filed Feb. 27, 2015.

Jeffery et al.; U.S. Appl. No. 14/634,661 entitled "Methods for attaching and wearing a neurostimulator," filed Feb. 27, 2015.

Axelgaard Manufacturing Co. Ltd.; Little PALS® (product information); 2 pgs.; printed Feb. 11, 2013 from http://www.axelgaard.com/prod_little-pals.html.

Axelgaard Manufacturing Co. Ltd.; PALS® Platinum Blue (product information); 2 pgs.; printed Feb. 11, 2013 from http://www.axelgaard.com/prod_pals-platinum-blue.html.

Bachtold et al.; Focused ultrasound modifications of neural circuit activity in a mammalian brain; Ultrasound Med Biol; 24(4); 557-565; May 1998.

Breneman et al.; Piezo- and Flexoelectric Membrane Materials Underlie Fast Biological Motors in the Ear. Mat Res Soc Symp Proc; 1186E; Spring 2009 (author manuscript, 9 pgs.).

Bystritsky et al.; A review of low-intensity focused ultrasound pulsation. Brain stimulation; 4(3); 125-136; Jul. 2011.

Chaieb et al.; Transcranial alternating current stimulation in the low kHz range increases motor cortex excitability; Restor Neurol Neurosci; 29(3); pp. 167-175; Mar. 2011.

Dalecki, D.; Mechanical bioeffects of ultrasound. Annual review of biomedical engineering; 6; 229-248; Aug. 2004.

DaSilva et al.; Electrode positioning and montage in transcranial direct current stimulation; J Vis Exp; 51; e2744; 11 pgs.; May 2011.

Digitimer Ltd.; DS2 and DS3 Isolated Stimulator (product information); 2 pgs.; downloaded from http://www.digitimer.com/research/stimulators/index.htm on Feb. 10, 2014.

Electozyme; Company and Product Information; 3 pgs.; printed Feb. 11, 2014 from http://electrozyme.com/applications/.

Feurra et al.; Frequency specific modulation of human somatosensory cortex; Front Psychol; 2(13); 6 pgs.; Feb. 2011.

Garilov et al.; The effect of focused ultrasound on the skin and deep nerve structures of man and animal. Progress in brain research; 43; 279-292; 1976 (year of pub. sufficiently earlier than effective US filing date and any foreign priority date).

GoFLOW; tDCS Kit; product information; 9 pgs.; printed Feb. 10, 2014 (http://flowstateengaged.com/).

Griesbauer et al.; Wave Propagation in Lipid Monolayers; Biophysical Journal; 97(10); 2710-2716; Nov. 2009.

Grindhouse Wetware; Thinking Cap; product information; 1 pg.; printed Feb. 10, 2014 (http://www.grindhousewetware.com/thinkingcap.html).

Heimburg, T.; Lipid ion channels. Biophysical chemistry; 50; pp. 2-22; Aug. 2010.

Hynynen et al.; 500-element ultrasound phased array system for noninvasive focal surgery of the brain: a preliminary rabbit study with ex vivo human skulls. Magnetic resonance in medicine; 52(1), 100-107; Jul. 2004.

Yoo et al.; Focused ultrasound modulates region-specific brain activity; NeuroImage; 56(3); pp. 1267-1275; Jun. 2011.

Hynynen et al.; Clinical applications of focused ultrasound-the brain. International journal of hyperthermia ; 23(2), 193-202; Mar. 2007.

Kanai et al.; Frequency-dependent electrical stimulatioin of the visual cortex; Curr. Biol.; 18(23); pp. 1839-1843; Dec. 9, 2008.

Mihran et al.; Temporally-specific modification of myelinated axon excitability in vitro following a single ultrasound pulse. Ultrasound in Medicine & Biology; 16(3), 297-309; 1990 (year of pub. sufficiently earlier than effective US filing date and any foreign priority date).

Min et al.; Focused ultrasound-mediated suppression of chemically-induced acute epileptic EEG activity. BMC Neuroscience; 23, 12 pgs.; Mar. 2011.

Morris et al.; Lipid stress at play: Mechanosensitivity of voltage-gated channels; Mechanosensitive Ion Channels, B. Current Topics in Membranes; 59, Chapter 11; 297-338; 2007 (year of pub. sufficiently earlier than effective US filing date and any foreign priority date).

Morris et al.; Nav channel mechanosensitivity: activation and inactivation accelerate reversibly with stretch. Biophysical Journal; 93(3); 822-833; Aug. 2007.

O'Brien, Jr.; Ultrasound-biophysics mechanisms. Progress in biophysics and molecular biology; 93(1-3), pp. 212-255; Jan.-Apr. 2007 (author manuscript; 74 pgs.).

Paulus, W.; Transcranial electrical stimulation (tES-tDCS; tRNS, tACS) methods; Neuropsychol Rehabil.; 21(5); pp. 602-617; Oct. 2011.

Petrov et al.; Flexoelectric effects in model and native membranes containing ion channels; European biophysics journal; 22(4); pp. 289-300; Oct. 1993.

Prausnitz; The effects of electric current applied to skin: a review for transdermal drug delivery; Advanced Drug Delivery Reviews; vol. 18; pp. 395-425; Feb. 8, 1996.

Rinaldi et al.; Modification by focused ultrasound pulses of electrically evoked responses from an in vitro hippocampal preparation. Brain Research; 558(1); pp. 36-42; Aug. 1991.

Rossini et al.; Non-invasive electrical and magnetic stimulation of the brain, spinal cord and roots: basic principles and procedures for routine clinical application; Electroenceph. Clin. Neurophysiol.; 91(2); pp. 79-92; Aug. 1994.

Saiote et al.; High-frequency TRNS reduces BOLD activity during visuomotor learning; PLOS one; 8(3); e59669; 8 pgs.; Mar. 2013.

Schutter et al.; Brain oscillations and frequency-dependent modulation of cortical excitability; Brain Stimulation; 4(2); pp. 97-103; Apr. 2011.

Shealy et al.; Reversible effects of ultrasound on spinal reflexes; Archives of neurology; 6; pp. 374-386; May 1962.

STD Pharmaceutical Products; Idrostar intophoresis machine (product and use information); 9 pgs.; Dec. 2011 (printed Feb. 11, 2014 from http://www.iontophoresis.info/instructions/).

Sukharev et al.; Mechanosensitive channels: multiplicity of families and gating paradigms. Sci STKE; vol. 2004; p. re4 (24 pgs.); Feb. 2004.

Ter Haar; Therapeutic applications of ultrasound. Prog Biophysics Mol Biol; 93; pp. 111-129; Jan.-Apr. 2007.

Terney et al.; Increasing human brain excitability by transcranial high-frequency random noise stimulation; The Journal of Neuroscience; 28(52); pp. 14127-14155; Dec. 2008.

(56) References Cited

OTHER PUBLICATIONS

Tsui et al.; In vitro effects of ultrasound with different energies on the conduction properties of neural tissue; Ultrasonics; 43; pp. 560-565; Jun. 2005.

Tufail et al.; Transcranial pulsed ultrasound stimulates intact brain circuits; Neuron; 66, pp. 681-694; Jun. 2010.

Tufail et al.; Ultrasonic neuromodulation by brain stimulation with transcranial ultrasound. Nature protocols; 6(9); pp. 1453-1470; Sep. 2011.

Turi et al.; Both the cutaneous sensation and phosphene perception are modulated in a frequency-specific manner during transcranial alternating current stimulation; Restor. Neurol. Neurosci.; 31(3); pp. 275-285; 2013 (year of pub. sufficiently earlier than effective US filing date and any foreign priority date).

Tyler et al.; U.S. Appl. No. 61/663,409 entitled "Device and Methods for Noninvasive Neuromodulation Using Targeted Transcranial Electrical Stimulation," filed Jun. 22, 2012.

Tyler et al.; U.S. Appl. No. 61/550,334 entitled "Improvement of Direct Communication," filed Oct. 21, 2011.

Tyler et al; Remote excitation of neuronal circuits using low-intensity, low-frequency ultrasound. PLoS ONE; 3(10); e3511; pp. 1-11; Oct. 2008.

Velling et al.; Modulation of the functional state of the brain with the aid of focused ultrasonic action; Neuroscience and behavioral physiology; 18; pp. 369-375; Sep.-Oct. 1988.

Vickery et al.; Ubiquity and Specificity of Reinforcement Signals throughout the Human Brain. Neuron; 72; pp. 166-177; Oct. 2011.

Yang et al.; Transcranial ultrasound stimulation: a possible therapeutic approach to epilepsy. Medical Hypotheses; 76(3); pp. 381-383; Mar. 2011.

Yoo et al.; Transcranial focused ultrasound to the thalamus alters anesthesia time in rats; NeuroReport; 22(15); pp. 783-787; Oct. 2011 (author manuscript; 9 pgs.).

Zaghi et al.; Noninvasive brain stimulation with low-intensity electrical currents: putative mechanisms of action for direct and alternating current stimulation; Neuroscientist; 16(3); pp. 285-307; Jun. 2010 (pre-pub version; 24 pgs.).

Goldwasser et al.; U.S. Appl. No. 14/715,461 entitled "Wearable transdermal neurostimulator having cantilevered attachment," filed May 18, 2015.

Charlesworth et al.; U.S. Appl. No. 14/715,476 entitled "Methods and apparatuses for amplitude-modulated ensemble waveforms for neurostimulation," filed May 18, 2015.

Demers et al.; U.S. Appl. No. 14/715,483 entitled "Methods and apparatuses for control of a wearable transdermal neurostimulator to apply ensemble waveforms," filed May 18, 2015.

Demers et al.; U.S. Appl. No. 14/715,470 entitled "Transdermal neurostimulator adapted to reduce capacitive build-up," filed May 18, 2015.

Coutinho et al.; Musical emotions: predicting second-by-second subjective feelings of emotion from low-level psychoacoustic features and physiological measurements; Emotion; 11(4); pp. 921-937; Aug. 2011.

Gracenote; Timeline-metadata-api; 3 pages; retrieved from the internet Jul. 7, 2015; (https://github.com/gracenote/timeline-metadata-api/blob/master/README.md).

\* cited by examiner

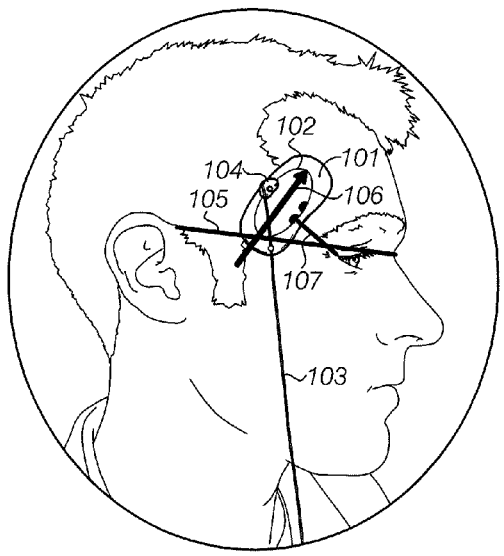
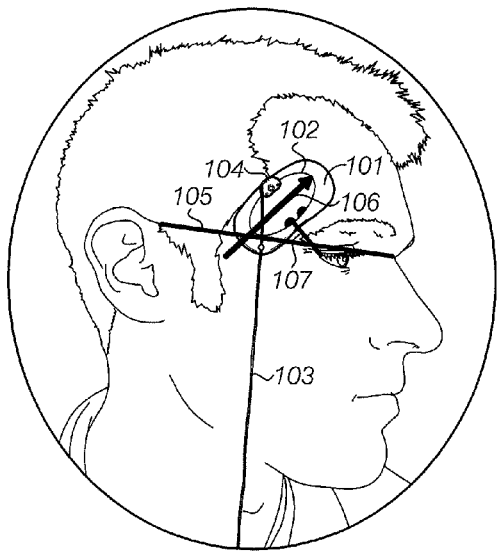
FIG.1A    FIG.1B
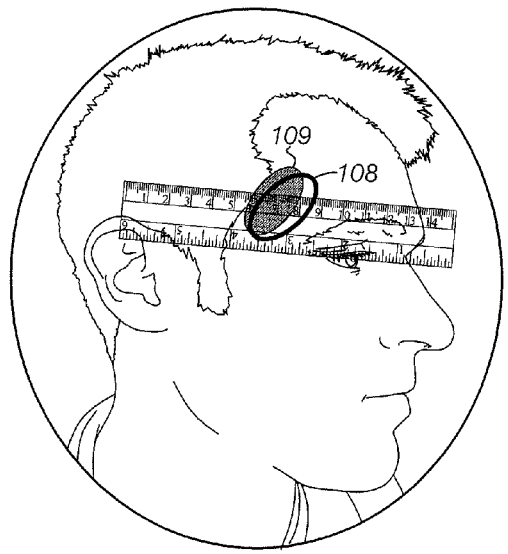
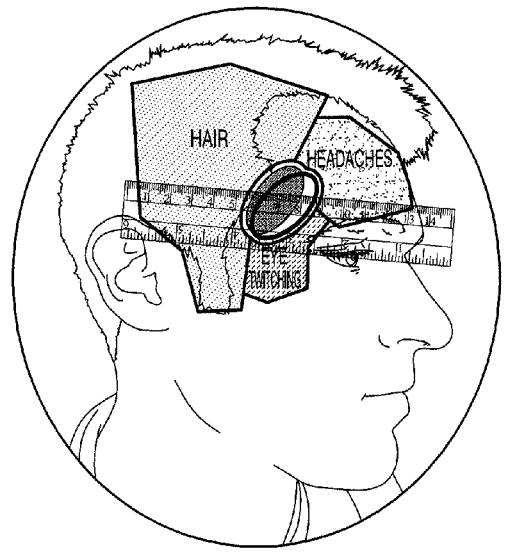
FIG.1C    FIG.1D

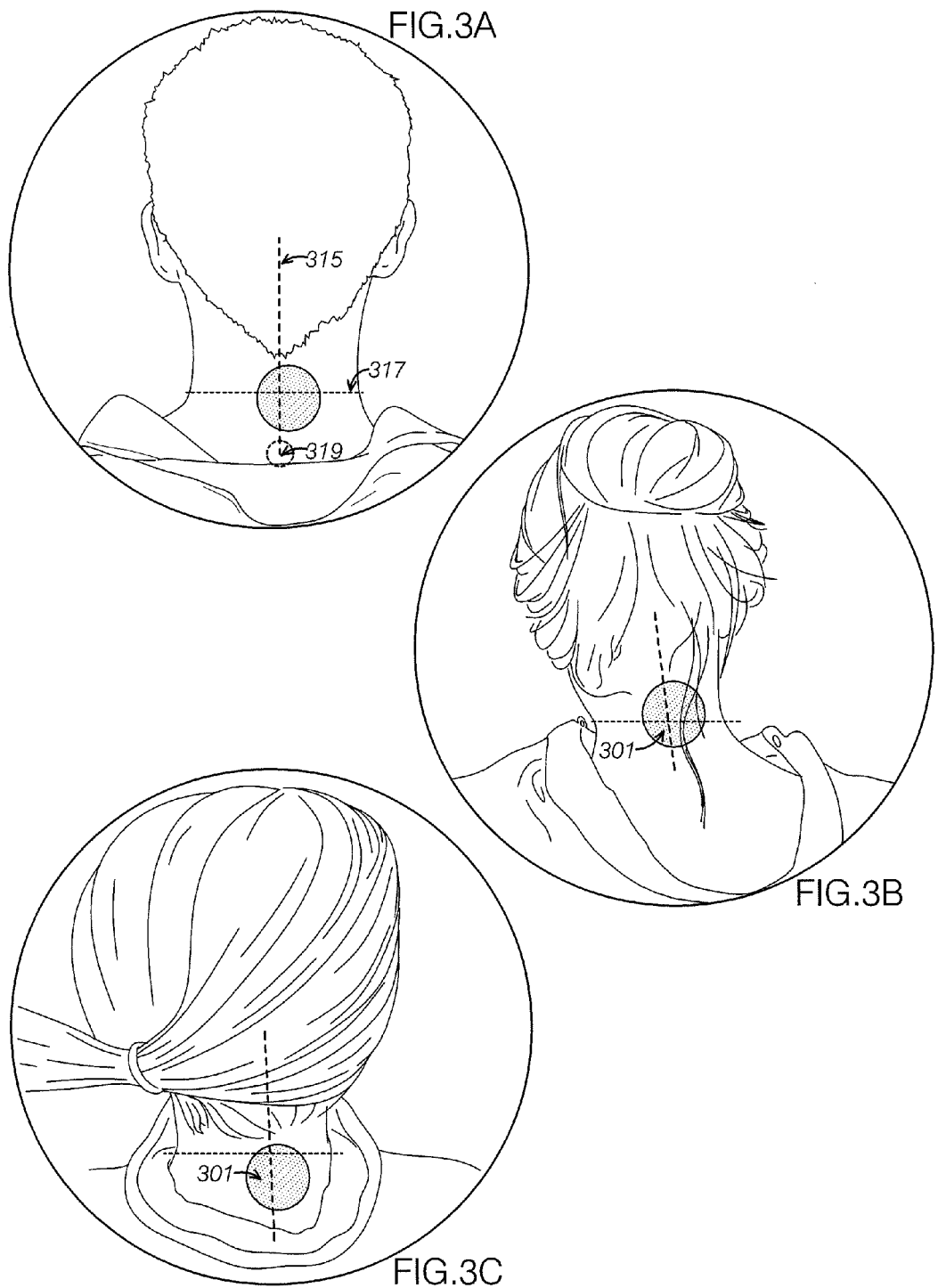

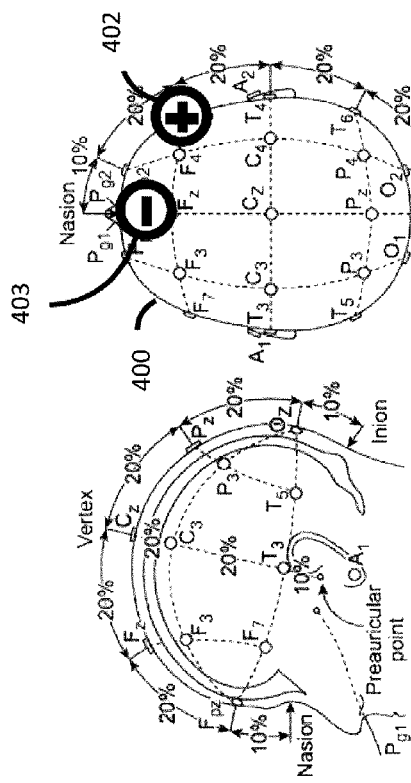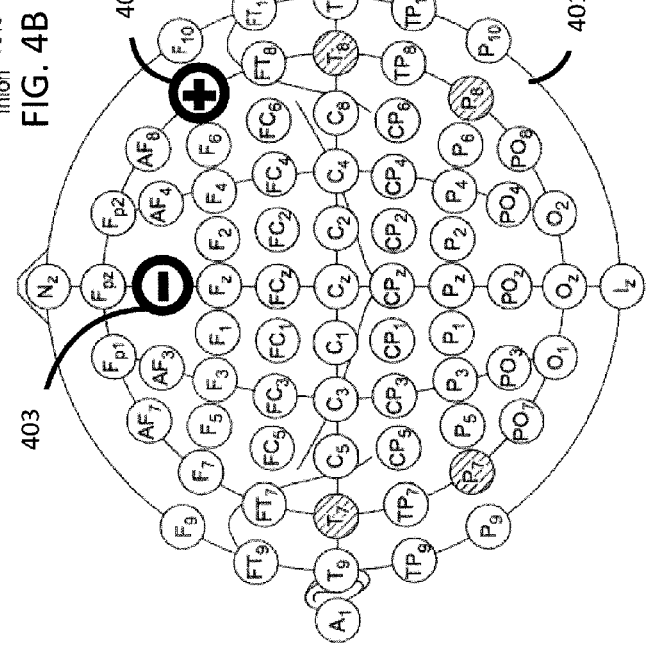
FIG. 4A
FIG. 4B
FIG. 4C

Time

Time

Time

Time

TRANSDERMAL ELECTRICAL STIMULATION DEVICES FOR MODIFYING OR INDUCING COGNITIVE STATE

CROSS REFERENCE TO RELATED APPLICATIONS

This patent application is a continuation of U.S. patent application Ser. No. 14/320,461, titled "TRANSDERMAL ELECTRICAL STIMULATION DEVICES FOR MODIFYING OR INDUCING COGNITIVE STATE," filed on Jun. 30, 2014, now U.S. Patent Application Publication No. US-2015-000584, which is herein incorporated by reference in its entirety.

Ser. No. 14/320,461 also claims priority to each of the following U.S. provisional patent applications, each of which is herein incorporated by reference in its entirety: U.S. Provisional Application No. 61/845,845, titled "TRANSCRANIAL ELECTRICAL STIMULATION SYSTEMS AND METHODS" and filed on Jul. 12, 2013; U.S. Provisional Application No. 61/875,424, titled "TRANSCRANIAL ELECTRICAL STIMULATION SYSTEMS AND METHODS" and filed on Sep. 9, 2013; U.S. Provisional Application No. 61/841,308, titled "TRANSCRANIAL ELECTRICAL STIMULATION SYSTEMS" and filed on Jun. 29, 2013; U.S. Provisional Application No. 61/907,394, titled "TRANSCRANIAL ELECTRICAL STIMULATION SYSTEMS AND METHODS" and filed on Nov. 22, 2013; U.S. Provisional Application No. 61/888,910, titled "TRANSCRANIAL ELECTRICAL STIMULATION SYSTEMS AND METHODS" and filed on Oct. 9, 2013; U.S. Provisional Application No. 61/975,118, titled "TRANSDERMAL ELECTRICAL STIMULATION SYSTEMS" and filed on Apr. 4, 2014; U.S. Provisional Application No. 62/002,860, titled "TRANSDERMAL ELECTRICAL STIMULATION SYSTEMS FOR INDUCING COGNITIVE EFFECTS AND METHODS OF USING THEM" and filed on May 25, 2014; U.S. Provisional Application No. 62/002,909, titled "TRANSDERMAL ELECTRICAL STIMULATION SYSTEMS AND METHODS OF USING THEM" and filed on May 25, 2014; and U.S. Provisional Application No. 62/002,910, titled "TRANSDERMAL ELECTRICAL STIMULATION ELECTRODE DEGRADATION DETECTION SYSTEMS AND METHODS OF USING THEM" and filed on May 25, 2014.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are transdermal electrical stimulation (TES) methods, apparatuses and systems, including applicators, for inducing cognitive effects.

BACKGROUND

The brain is composed of neurons and other cell types in connected networks that process sensory input, generate motor commands, and control all other behavioral and cognitive functions. Neurons communicate primarily through electrochemical pulses that transmit signals between connected cells within and between brain areas. Noninvasive neuromodulation technologies that affect neuronal activity can modulate the pattern of neural activity and may cause altered behavior, cognitive states, perception, and motor output without requiring an invasive procedure.

Non-invasive neuromodulation includes the broad category of "transdermal electrical stimulation," which generally refers to electrical stimulation of the nervous system (brain, cranial nerves, peripheral nerves, etc.) through a subject's skin. Specific examples of transdermal electric stimulation (hereinafter "TES") may include transcranial stimulation, for example, through scalp electrodes and have been used to affect brain function in humans in the form of transcranial alternating current stimulation (hereinafter "tACS"), transcranial direct current stimulation (hereinafter "tDCS"), cranial electrotherapy stimulation (hereinafter "CES"), and transcranial random noise stimulation (hereinafter "tRNS"). Systems and methods for TES have been disclosed (see for example, Capel U.S. Pat. No. 4,646,744; Haimovich et al. U.S. Pat. No. 5,540,736; Besio et al. U.S. Pat. No. 8,190,248; Hagedorn and Thompson U.S. Pat. No. 8,239,030; Bikson et al. US patent application 2011/0144716; and Lebedev et al. US patent application 2009/0177243). tDCS systems with numerous electrodes and a high level of configurability have been disclosed (see for example Bikson et al. US Patent applications 2012/0209346, 2012/0265261, and 2012/0245653), as have portable TES systems for auto-stimulation (Brocke U.S. Pat. No. 8,554,324).

In general, TES has been shown to improve motor control and motor learning, improve memory consolidation during slow-wave sleep, regulate decision-making and risk assessment, affect sensory perception, and cause movements. TES has been used therapeutically in various clinical applications, including treatment of pain, depression, epilepsy, and tinnitus. In at least some cases of TES (e.g., tDCS) therapeutic use, more data concerning the efficacy of tDCS in treatment is needed.

Despite research done on TES neuromodulation, existing systems and methods for TES are lacking in at least some cases in their capacity to safely and robustly affect cognitive function and induce cognitive states in human subjects. The development of new TES methods, TES stimulation protocols, TES systems, and TES electrode configurations that induce substantial changes in cognitive function and/or cognitive state comfortably would be advantageous. Existing systems and methods can cause skin irritation or pain and are lacking with regard to the reliability and amount of change in cognitive state that can be achieved.

Electrotherapy for muscles and other peripheral nervous system applications (e.g. TENS & transdermal drug delivery) have used strategies to reduce pain, irritation, and tissue damage, including (1) higher frequencies of alternating current stimulation and (2) a beat frequency generally between 1 Hz and 200 Hz created from a difference frequency of two channels (anode-cathode pairs) of electrodes. Reduced side-effects (e.g. pain and irritation) are approximately linear across a wide range from ~1 kHz to 100 kHz. Skin impedance is frequency dependent, with lower impedances at higher electrical stimulation frequencies. For interferential stimulation, a beat frequency of between 1 and 200 Hz is an advantageous frequency to avoid activating pain & muscle fibers that are perceived as irritating or painful. Power density also affects skin resistivity, with lower resistivity occurring at higher power densities. However, systems and methods for TES are lacking in terms of mitigation of pain, irritation, and tissue damage.

Typical transcranial alternating current stimulation protocols are also typically below 150 Hz (see Paulus 2011), consistent with frequencies of brain rhythms or below 640 Hz as used in tRNS protocols. Recently, Chaieb et al. used 1 kHz, 2 kHz, and 5 kHz tACS to induce neuromodulation (Chaieb L, Antal A, Paulus W. "Transcranial alternating current stimulation in the low kHz range increases motor cortex excitability." Restor Neurol Neurosci. 2011; 29(3):167-75, incorporated fully herein by reference). Patent Application No. WO 2012/089,588 by inventors Paulus and Warschewske describes systems and methods of tACS at frequencies between 1 Hz and 50 kHz, including interferential tACS from two anode-cathode electrode pairs and pulsed tACS. However, existing tACS systems for neuromodulation are less than ideal for inducing cognitive effects robustly and comfortably.

One advantage of transcranial alternating current stimulation relative to transcranial direct current stimulation is reduced pain and irritation. However, existing tACS systems for neuromodulation are less than ideal in at least some instances, because alternating currents affect nervous system function (i.e., brain function) differently than direct currents. One advantage of pulsed transcranial direct current stimulation relative to unpulsed transcranial direct current stimulation is reduced pain and irritation. Pulsed transcranial direct current stimulation has been previously reported for peripheral use in patients but has not been used for targeting the brain transcranially. The Idrostar Iontophoresis Machine (STD Pharmaceutical Products Ltd, Hereford, England) delivers pulsed direct current stimulation (7 kHz, about 42% duty cycle) to address hyperhidrosis (excess sweating). Alternative transcranial electrical stimulation protocols that achieve desired effects on the nervous system with manageable amounts of pain and/or irritation would be advantageous.

It would generally be advantageous to provide devices and methods that allow transdermal electrical stimulation in a manner that overcomes the problems with pain and efficacy discussed above. In particular, it would be beneficial to provide TES devices and methods for modulating (e.g., inducing, enhancing, reversing, or otherwise increasing or changing) a cognitive effect and/or mental state. For example, TES stimulation protocols and electrode configurations that induce a relaxing, calming, anxiolytic, dissociated, high mental clarity, or worry-free state of mind in a subject would be advantageous for improving the subject's experiences and state of mind, as well as addressing insomnia and mitigating negative responses to stress. Similarly TES stimulation protocols and apparatuses that increase a subject's motivation, subjective (and/or physiological) energy level, or focus would be advantageous for improving a subject's productivity and providing beneficial states of mind. Described herein are methods and apparatuses (including devices and systems) and methods that may address the problems and opportunities discussed above.

SUMMARY OF THE DISCLOSURE

Described herein are apparatuses (including devices and systems) and methods for transdermal electrical stimulation (hereinafter "TES"), including transcranial electrical stimulation, to induce neuromodulation.

In general, the devices described herein include a pair of electrodes that may be connected to different, predefined regions of a subject's head and/or neck, and a TES control module that is configured specifically to deliver stimulation within a range of parameters, including intensity and frequency, determined to be effective for inducing, enhancing, or promoting (collectively, "modifying") a desired cognitive state and/or effect while minimizing pain and discomfort due to the relatively large magnitude stimulation provided. For example, an apparatus (such as an applicator) may include a control module having circuitry (e.g., hardware), software and/or firmware that allows the apparatus to apply signals within an effective range, including, for example, one or more processors, timers and waveform generators. In general, the TES control module may be specifically adapted to deliver a biphasic electrical stimulation signal of 10 seconds or longer between the first and second electrodes, where the signal has a frequency of 100 Hz or greater (e.g., 200 Hz or greater, 400 Hz or greater, 450 Hz or greater, 500 Hz or greater, 600 Hz or greater, 700 Hz or greater, etc.) and an intensity of 2 mA or greater (e.g., 3 mA or greater, 4 mA or greater, 5 mA or greater, etc.). The control module may also be configured to reduce pain when applying the stimulation by controlling the duty cycle (e.g., the percent of time that the current applied is non-zero, and/or greater than zero), e.g. so that the duty cycle of the applied energy is greater than 10 percent (e.g., greater than 15 percent, greater than 20 percent, greater than 30 percent). In addition, the control module may be configured so that the applied current is biphasic and/or is not charge balanced (e.g., has a DC offset, also referred to as DC bias, so that the mean amplitude of the applied waveform is non-zero). Alternatively or in addition, the control module (TES control module) may be configured to discharge capacitance built up on the electrodes, e.g., by occasionally or periodically "shorting" the electrodes, and/or by applying an opposite current(s). In general, a control module may be configured to generate stimulation that includes these parameters, and may be configured to prevent stimulation outside of these parameters, in order to avoid inducing pain.

These parameters, which are described in greater detail below, are generally adapted to cause a cognitive effect. The devices and methods described herein allow the reproducible evoking of cognitive effects, as are described herein. The nature of the cognitive effect resulting from the methods and devices described may depend, at least in part, on the positioning of the electrodes on the subject's body (e.g., head, neck, etc.). For example, a class of cognitive effects generally results in the subject experiencing an increased mental focus and may include: enhanced focus and attention; enhanced alertness; increased focus and/or attention; enhanced wakefulness; increased subjective feeling of energy; increased objective (i.e. physiological) energy levels; higher levels of motivation (e.g. to work, exercise, complete chores, etc.); increased energy (e.g., physiological arousal, increased subjective feelings of energy); and a physical sensation of warmth in the chest. This class of cognitive effects may be referred to collectively as enhancing (or enhanced) attention, alertness, or mental focus.

Another example of a class of cognitive effects includes those associated with relaxation and a calm mental state, for example: a state of calm, including states of calm that can be rapidly induced (i.e. within about 5 minutes of starting a TES session); a care-free state of mind; a mental state free of worry; induction of sleep; a slowing of the passage of time; enhanced physiological, emotional, or and/or muscular relaxation; enhanced concentration; inhibition of distractions; increased cognitive and/or sensory clarity; a dissociated state; a state akin to mild intoxication by a psychoactive compound (i.e. alcohol); a state akin to mild euphoria induced by a psychoactive compound (i.e. a morphine); the induction of a state of mind described as relaxed and pleasurable; enhanced enjoyment of auditory and visual experiences (i.e., multimedia); reduced physiological arousal; increased capacity to handle emotional or other stressors; a reduction in psychophysiological arousal as associated with changes in the activity of the hypothalamic-pituitary-adrenal axis (HPA axis) generally associated with a reduction in biomarkers of stress, anxiety, and mental dysfunction; anxiolysis; a state of high mental clarity; enhanced physical performance; promotion of resilience to the deleterious consequences of stress; a physical sensation of relaxation in the periphery (i.e., aims and/or legs); a physical sensation of being able to hear your heart beating, and the like. This class of cognitive effects may be referred to collectively as "a calm or relaxed mental state".

The methods described herein include methods of positioning the electrodes on the subject to evoke a particular cognitive effect when applying stimulation. Devices (e.g., applicators) may be particularly adapted or configured for a particular positioning configuration. For example, an applicator may include the surface of an electrode (or electrodes) that is adapted to fit into a particular location on the subject's body to evoke a predetermined cognitive effect. Also, although the majority of the examples described herein refer to a single electrode (anode/cathode) positioned at a first location and a single (counter, e.g., cathode/anode) electrode positioned at a second location, multiple electrodes (including multiple anodes and/or multiple cathodes) may be positioned at each location. In general, the electrode positioning relative to a particular body site refers to the positioning the electrode so that the peak density of the applied current from the electrode(s) is at the target location; thus the electrodes may be smaller or larger than the target region. Proper electrode positioning, as described in greater detail herein, may also prevent pain and discomfort. In general, the electrodes referred to herein form pairs that are separated on the subject's body; although one end of a pair may be made up of multiple electrodes. For example, a first electrode (or collection of electrodes) may be positioned on a first location on the subject's head or neck. A second electrode (or collection of electrodes) may be positioned at a second location on the subject, including the head or neck. This first electrode may be an anode and the second electrode may be a cathode; or conversely the first electrode may be a cathode and the second electrode an anode. TES current is typically applied between the two electrodes (or two groups of electrodes).

For example, in one configuration (referred to herein for convenience as "configuration A" or "configuration 2") a first electrode may be applied to the subject near the temple area (e.g., laterally to the eye, such as slightly above and to the right of the right eye or the left eye) and at least one second electrode may be positioned behind the right ear in the mastoid region (e.g., on or near the mastoid). The electrode may be any appropriate size (e.g. area), for example, an electrode may have an area at least about 10 cm$^2$ (e.g., at least about 20 cm$^2$) near the right temple and a smaller mastoid electrode between about 3 cm$^2$ and about 10 cm$^2$. TES stimulation of this region may result in enhanced attention, alertness, or mental focus.

Another configuration (referred to herein for convenience as "configuration B" or "configuration 3") may include an electrode positioned on the subject's skin near the subject's temple area (e.g., above and to the right of the right eye) and a second electrode on the subject's neck (e.g., on a superior portion of the neck centered to the right of the midline and, optionally, partially overlapping the spinal cord). Beneficial embodiments comprise electrodes for the neck having an area of at least about 20 cm$^2$ and an electrode having area at least about 10 cm$^2$ (optimally at least about 20 cm$^2$) near the right temple. TES stimulation of this region may result in enhancing a calm or relaxed mental state.

For both of these exemplary configurations, waveforms of transdermal electrical stimulation as provided herein may induce a strong and reliable cognitive effect while mitigating skin irritation, pain, and tissue damage. Waveforms may be defined according to one or more of: frequency, peak intensity, duty cycle, the proportion of non-zero current flow that is positive-going (i.e. 'percent direct current'), whether the waveform is biphasic or only transmits current in one direction, and whether the electrical stimulation system shorts the electrical paths between the anode and cathode between pulses. In some embodiments, ramping of parameters (i.e. frequency, peak intensity, duty cycle) between two values occurs during a waveform or portion of a waveform.

Any of the waveforms described herein may be applied continuously or intermittently, including with variations such as transitions states (e.g., ramps) from outside of these ranges into these ranges or within the ranges of current and frequency (and in some variations, DC offset and/or duty cycle). In general, ramping and other waveform features can be incorporated in order to shift a waveform between different effective ranges of parameters for inducing a particular cognitive effect and thus achieve a more intense, longer lasting cognitive effect. Shifting between effective waveforms may be iterative (i.e. one parameter changes, than another changes) and may be repetitive (i.e. change from one waveform to a second waveform, then back to the first waveform, etc.; or toggling between three or more effective waveforms). In some embodiments, rapidly shifting one or more waveform parameters within an effective range induces a stronger cognitive effect, wherein rapid generally refers to less than 15 seconds and may be as short as one second or less.

As mentioned, the devices described herein may include a controller having components operating at high voltage so that sufficiently high peak currents can be achieved (i.e. greater than 10 V, greater than 15 V, greater than 20 V, greater than 25 V, greater than 30 V, greater than 35 V, greater than 40 V, greater than 45 V, greater than 50 V, greater than 55 V, greater than 60 V, greater than 65 V, and greater than 75V). Impedances of a subject's tissue (mostly due to skin impedance) and hardware components of the system including electrodes are generally between 1 kOhm and 20 kOhm (though occasionally up to 30 kOhm or higher), so high voltage current sources above 50 V are beneficial for delivering higher peak currents required for inducing a cognitive effect.

In general, described herein are methods of modifying a subject's cognitive state. For example, a method of modifying a subject's cognitive state may typically include: placing a first electrode of a transdermal electrical stimulation (TES) applicator on the subject's skin on a temple region on a first side of the subject's body; placing a second electrode on the subject's skin on either the mastoid region of the first side of the subject's body or on the subject's neck above the vertebra prominens; activating the TES applicator to deliver a transdermal electrical stimulation having a frequency of 100 Hz or greater and an intensity of 2 mA or greater; and modifying the subject's cognitive state by applying the transdermal electrical stimulation between the first and second electrodes for 10 seconds or longer.

For example, described herein are methods of modifying a subject's cognitive state, the method comprising: placing a first electrode of a portable transdermal electrical stimulation (TES) applicator on the subject's skin on a temple region on a first side of the subject's body; placing a second electrode on the subject's skin on either the mastoid region of the first side of the subject's body or on the subject's neck; activating the TES applicator to deliver a biphasic transdermal electrical stimulation having a frequency of 400 Hz or greater and an intensity of 3 mA or greater, wherein the biphasic transdermal electrical stimulation has a DC offset; and modifying the subject's cognitive state by applying the biphasic transdermal electrical stimulation between the first and second electrodes for 10 seconds or longer. Activating the portable TES applicator may include activating the TES applicator to deliver the biphasic transdermal electrical stimulation having a duty cycle of greater than 10 percent.

These methods may be specific to methods for enhancing attention, alertness, or mental focus or for enhancing a calm or relaxed mental state. For example, modifying the subject's cognitive state may comprise enhancing attention, alertness, or mental focus, and placing the second electrode may comprise placing the second electrode on the mastoid region of the first side of the subject's body. Similarly, modifying the subject's cognitive state may comprise enhancing a calm or relaxed mental state, and placing the second electrode may comprise placing the second electrode on the back of the subject's neck.

Any of the methods described herein may be performed by the subject wearing the device. This is possible because the devices described herein are configured to be relatively light-weight and easy to work with so that an untrained user may be able to operate them. For example the subject may place the first electrode and the second electrode on his/her head and/or neck, without the need for a physician or third party to participate.

Once applied, the application of TES may be triggered automatically (e.g., after sensing attachment), or manually and either locally (e.g., operating a switch on the device) or remotely, e.g., using a device that wirelessly communicates with the device once applied to the subject's head. The subject may activate and/or modify operation of the TES himself or herself. For example, activating the portable TES applicator may include wirelessly triggering activation of the portable TES applicator. Activating the portable TES applicator comprises triggering activation of the portable TES applicator from a handheld device.

As mentioned, during the application of the TES, the applied TES does not need to be constant, but may preferably be variable and/or intermittent. For example, application of TES may include varying the applied biphasic transdermal electrical stimulation while the biphasic transdermal stimulation is applied. The applied biphasic transdermal electrical stimulation may be varied while keeping the biphasic transdermal electrical stimulation within a duty cycle of greater than 10 percent, a frequency of 400 Hz or greater, and an intensity of 3 mA or greater (and with a DC offset).

In general, to provide effective and comfortable TES, the parameters of intensity and frequency may be held within the specified ranges. For example, intensity (current) may be high, e.g. greater than about 2 mA, greater than 3 mA, or preferably greater than 4 mA or greater than 5 mA (e.g., between 5 mA and 20 mA). The frequency of the stimulation may be generally relatively high, for example, greater than 100 Hz, greater than 200 Hz, greater than 400 Hz or more particularly greater than 450 Hz or greater than 500 Hz. Operation of these parameters may typically be done with a biphasic stimulation (e.g., having a periodic rise and fall, typically having two phases), and may also include a DC offset so that the signal is not charge balanced. As mentioned, in general a direct current (DC) offset (also referred to as a DC component, DC bias, or DC coefficient) is the mean value of the waveform. If the mean amplitude is zero, there is no DC offset. Thus, the applied TES may typically be pulsed, biphasic and asymmetric. Similarly, the TES stimulation may also have a duty cycle that is between 10% and 100% (e.g., less than 100% and greater than 10%), including greater than 20% or greater than 30%.

In any of these TES protocols, the electrodes may be 'shorted' during the stimulation (within the application of the TES periodically or occasionally) to discharge capacitive build up on the electrodes. Similarly, any of the devices (e.g., TES applicators) described herein may include short-circuiting features. For example, a short-circuit for the electrodes may be made with a fixed current source similar to the main current source, but the 'shorting' source may be saturating at 0V and then can just discharge the accumulated charges. In some variations the nominal (or maximal) short-circuit current may be preset (e.g., 40 mA) and/or may be changed by changing a resistor. Alternatively, discharging can be made by the regular current source with an adjustable current inside the range. For example, the range may be up to 20 mA, and turning on rectified switches may avoid reverse charging.

In general, ramping the biphasic transdermal electrical stimulation during the application may be achieved by decreasing one or more of the intensity, duty cycle or DC offset and then increasing one or more of the intensity, duty cycle or DC offset (similarly, frequency may be ramped by increasing then decreasing the frequency).

When placing the electrode on the temple, placement may be made to optimize the effect while avoiding pain. For example, placement on the temple may comprise placing the electrode lateral to the subject's eye and above the subject's cheekbone; for example, slightly above and to the right of the right eye, or to the left of the left eye. Placing the electrode on the temple may exclude placing the electrode on or near the subject's orbital region (to avoid pain and/or distracting muscle twitches around the eye) or below the cheekbone (to avoid reduced efficacy and/or muscle twitch).

In some variations, an electrode may be placed on the subject's forehead. In particular, the electrode may be placed so that the region of peak current is delivered on the skin over the subject's nasion, between the eyebrows and immediately above the nose (e.g., directly between the eyes, just superior to the bridge of the nose). For example, a first electrode may be placed on the nasion region and a second electrode on the temple, or the second electrode may be placed on the neck, or the second electrode may be placed behind the ear, as described, and TES applied as generally described herein. The use of the nasion electrode placement, particularly with the temple placement for the second electrode, may be used to for evoking, enhancing or improving a cognitive state such for enhancing attention, alertness, or mental focus.

In general, the electrodes may be placed on the same side of the subject's body (e.g., both on the right side or both on the left side).

In any of the methods described, the TES applicator may be self-contained, and may be lightweight. In particular, the applicator may be wearable. For example, the applicator may be adhesively secured to the subject's body (e.g., face, head, neck, etc.). Wearable devices (including applicators) are described in greater detail below, and are generally low-profile, e.g. projecting from the skin by less than about 2 cm, less than 1.5 cm, less than 1 cm, less than 0.5 cm, etc., and lightweight, e.g., less than 60 grams, less than 50 grams, less than 40 grams, less than 30 grams, etc.

The overall duration of the applied TES is generally longer than 10 seconds (though may be shorter in some variations) but may be more robustly applied for longer, including longer than 15 seconds, longer than 20 seconds, longer than 30 seconds, longer than 1 minute, longer than 5 minutes, etc. For example, modifying the subject's cognitive state may comprise applying the biphasic transdermal electrical stimulation between the first and second electrodes for 5 minutes or longer.

When placing the second electrode on the neck, an appropriate region of the neck may be the region of the neck above the vertebra prominens. The placement may be laterally offset from the midline of the neck, e.g., towards the side of the subject that the first electrode (the temple electrode) is positioned on.

As mentioned, any of the methods for modifying a subject's cognitive state may be performed by the subject. For example, described herein are methods of modifying a subject's cognitive state (including a calm or relaxed cognitive state or a cognitive state of attention, alertness, or mental focus), and may include the steps of: instructing a subject to place a first electrode of a portable transdermal electrical stimulation (TES) applicator on the subject's skin on a temple region on a first side of the subject's body; instructing the subject to place a second electrode on the subject's skin on the subject's head or neck on the first side of the subject's body; instructing the subject to modify their cognitive state by activating the portable TES applicator, wherein the portable TES applicator is configured to deliver a biphasic transdermal electrical stimulation between the first and second electrodes, the biphasic transdermal electric stimulation having a duty cycle of greater than 10 percent, a frequency of 400 Hz or greater, an intensity of 3 mA or greater, and a DC offset.

For example, a method of enhancing attention, alertness, or mental focus may include: placing a first electrode of a wearable transdermal electrical stimulation (TES) applicator on the subject's skin on a temple region on a first side of the subject's body; placing a second electrode on the subject's skin in the mastoid region of the first side of the subject's body; activating the wearable TES applicator to deliver a biphasic transdermal electrical stimulation having a duty cycle of greater than 10 percent, a frequency of 400 Hz or greater, and an intensity of 3 mA or greater, wherein the biphasic transdermal electrical stimulation has a DC offset; and enhancing attention, alertness or mental focus by applying the biphasic transdermal electrical stimulation between the first and second electrodes for 10 seconds or longer. As mentioned, the subject may place the first electrode and the second electrode, and/or may trigger or activate the wearable TES applicator, e.g., by wirelessly triggering activation of the wearable TES applicator. As described in more detail below, the subject may operate a remote controller (e.g., mobile phone/smart phone, laptop computer, pad, tablet, etc.).

Similarly, a method of enhancing a calm or relaxed mental state may include: placing a first electrode of a wearable transdermal electrical stimulation (TES) applicator on the subject's skin on a temple region on a first side of the subject's body; placing the second electrode on the back of the subject's neck above the vertebra prominens; activating the wearable TES applicator to deliver a biphasic transdermal electrical stimulation having a duty cycle of greater than 10 percent, a frequency of 400 Hz or greater, and an intensity of 3 mA or greater, wherein the biphasic transdermal electrical stimulation has a DC offset; and enhancing a calm or relaxed mental state by applying the biphasic transdermal electrical stimulation between the first and second electrodes for 10 seconds or longer. As mentioned, the subject may place the first electrode and the second electrode, and/or may trigger or activate the wearable TES applicator.

Also described herein are portable transdermal electrical stimulation (TES) applicators for modifying a subject's cognitive state. In general, these applicators may be lightweight (e.g., less than 60 grams, less than 50 grams, less than 40 grams, less than 30 grams, less than 25 grams, less than 20 grams, etc.) and may be wearable, including self-contained wearable devices that can be secured directly to the subject (e.g., by an adhesive).

For example, portable TES device (applicator) may include: a body (which may include a housing); a first electrode that is configured to be secured to the subject's skin; a second electrode that is configured to be secured to a second portion of the subject's skin, and is connected to the rest of the device by a cable, cord, etc.; and a TES control module at least partially within the body and comprising a processor, a timer and a waveform generator, wherein the TES control module is adapted to deliver a biphasic electrical stimulation signal of 10 seconds or longer between the first and second electrodes having a frequency of 400 Hz or greater, a duty cycle of greater than 10 percent, an intensity of 3 mA or greater, with a DC offset. The device may also include a wireless receiver coupled to the TES control module, a battery, and additional electronic components, including memory and the like.

A wearable transdermal electrical stimulation (TES) applicator for modifying a subject's cognitive state may include: a body adapted to be worn by the subject; a first electrode; a second electrode; a TES control module at least partially within the body, the TES control module including a power source, a processor, a timer, and a waveform generator, wherein the TES control module is adapted to deliver a biphasic electrical stimulation signal of 10 seconds or longer between the first and second electrodes having a frequency of 400 Hz or greater, a duty cycle of greater than 10 percent, an intensity of 3 mA or greater, with a DC offset; and a wireless receiver connected to the TES control module; wherein the wearable TES applicator weighs less than 50 grams.

A wearable transdermal electrical stimulation (TES) applicator for modifying a subject's cognitive state may include: a body adapted to be worn against the subject's skin; a first electrode on the body; a second electrode coupled to the body by a cord; and a TES control module at least partially within the body and comprising a processor, a timer and a waveform generator, wherein the TES control module is adapted to deliver a biphasic electrical stimulation signal of 10 seconds or longer between the first and second electrodes having a frequency of 400 Hz or greater, a duty cycle of greater than 10 percent, an intensity of 3 mA or greater, with a DC offset; further wherein the wearable TES applicator weighs less than 50 grams.

As mentioned above, any of the devices described herein may be configured to discharge capacitance built up on the electrodes during operation of the device. For example, any of these devices may include a capacitive discharge circuit. A capacitive discharge circuit may be controlled by the TES control module and may remove the discharge occasionally, periodically, or regularly during the application of stimulation by the device. Thus, a TES control module may be configured to occasionally or periodically trigger the capacitive discharge circuit to discharge capacitance on the electrodes during the delivery of the biphasic electrical stimulation.

Another example of the portable transdermal electrical stimulation (TES) applicators for modifying a subject's cognitive state described herein may include TES devices having the capacitive discharging features ('short circuiting' applicator) described. For example, a portable TES device for modifying a subject's cognitive state may include: a body; a first electrode; a second electrode; a TES control module at least partially within the body and comprising a processor, a timer and a waveform generator, wherein the TES control module is adapted to deliver a biphasic electrical stimulation signal of 10 seconds or longer between the first and second electrodes having a frequency of 400 Hz or greater, a duty cycle of greater than 10 percent, an intensity of 3 mA or greater, with a DC offset; and a capacitive discharge circuit, wherein the TES control module is configured to occasionally trigger the capacitive discharge circuit to discharge capacitance on the electrodes during the delivery of the biphasic electrical stimulation. The device may include a switch on the capacitive discharge circuit, wherein the switch is coupled to the TES control module.

Any of the methods described herein may include discharging the capacitance on the electrodes (e.g., short circuiting them) briefly during the application of the TES. For example, a method of modifying a subject's cognitive state may include: placing a first electrode of a transdermal electrical stimulation (TES) applicator on the subject's skin; placing a second electrode of the TES applicator on the subject's skin; activating the TES applicator to deliver a biphasic transdermal electrical stimulation having a frequency of 400 Hz or greater and an intensity of 3 mA or greater, wherein the biphasic transdermal electrical stimulation has a DC offset; modifying the subject's cognitive state by applying the biphasic transdermal electrical stimulation between the first and second electrodes for a treatment period of 10 seconds or longer; and triggering a capacitive discharge circuit for a sufficiently long enough time to discharge capacitance occasionally during the treatment period.

In general, the body region of any of the applicators described herein may include a housing to at least partially enclose some or all of the electronics. In general, the housing may be adapted to protect the electronics and the circuitry (such as the power supply, e.g., batteries, capacitors, etc., and the TES control module, etc.). In wearable variations the housing may be low-profile (e.g., thinner than 30 mm, thinner than 25 mm, thinner than 20 mm, thinner than 18 mm, thinner than 15 mm, etc.), and/or may be adapted to conform to a particular region of the head, such as the temple region. For example, the body may be elongate and curved, so that it can fit to the head and not overlap with the eye orbit region, which may interfere with vision. In some embodiments of the devices described herein the first electrode may be positioned on an outer surface of the body, and the second electrode may be connected to the body (e.g., to the TES control module) by a cord (wire, conductor, cable, etc.). The device may also include an adhesive (e.g. a biocompatible and/or conductive adhesive). In some variations both the first electrode and the second electrode are coupled to the body by a cord (either the same cord or two separate cords). In some variations the device is not held on the body, but is positioned nearby (e.g., by being worn on the subject's clothes, etc., or positioned near the subject (e.g., on a desk, in a pocket, etc.)).

Any of the devices described herein may include an input, and particularly a manual input, for entering control commands to regulate action/activity of the device. For example, the device may include a manual control on the body of the device that is coupled to the control module. A manual control may be a button, switch, touch screen, etc.

The TES controller may generally include one or more circuits specifically adapted to drive stimulation in the range of parameters that is relatively high-intensity (to effectively induce a cognitive state) but configured to prevent discomfort and/or pain. For example, the waveform generator of the TES module may include an oscillator (oscillator circuit) that can drive between 100 Hz and 30 KHz) as well as filters and rectifiers, as illustrated herein. In particular the devices described herein may generally include safety features such as current limiters, which may act as a fuse, to prevent harming the subject wearing the device. The TES controller may include or may be connected to a memory (e.g., a volatile memory such a one or more registers, flash memory, etc.) adapted to store information on the operation of the TES applicator.

Also described herein are methods and devices for TES modulation of a subject's cognitive state that provide or include TES with fast transitions during a TES treatment regime. Fast transitions may be referred to as ramps or as excursions, since they typically include a transition or excursion from a cognitive state-modifying simulation level to a stimulation level that is sub-threshold for inducing the cognitive effect, and then quickly back to the suprathreshold level for inducing the cognitive effect. The excursion stimulation ("ramping") is typically within the TES protocol, and enhances the cognitive effect and/or perception of the cognitive effect. While more gradual transition (or ramps) may be useful for reducing habituation, rapid (as described below) transitions may be particularly useful for enhancing the subject's experience of the induced cognitive state.

In general, a method of enhancing transdermal electrical stimulation (TES) for modifying a subject's cognitive state may include changing at least one of intensity, frequency, duty cycle and/or DC offset to change the stimulation being applied from the suprathreshold level for inducing the cognitive effect into a sub-threshold level for inducing the cognitive effect. The TES typically remains in the sub-threshold range only briefly (e.g., for less than 15 seconds, less than 10 seconds, less than 5 seconds, less than 2 seconds, etc.), before the stimulation is changed back to a suprathreshold level for inducing the cognitive effect. The change in the parameter level may occur relatively slowly compared to the time to restore the parameter to the suprathreshold level for inducing the cognitive effect, which typically occurs on the order of a few seconds.

For example a method of enhancing transdermal electrical stimulation (TES) for modifying a subject's cognitive state may include delivering a TES stimulation having an intensity, frequency, duty cycle and DC offset to the subject to evoke a cognitive state, the TES stimulation comprising a biphasic electrical stimulation having a target frequency of 400 Hz or greater, a target intensity of 3 mA or greater, a target duty cycle of greater than 10 percent, and a target DC offset of greater than 10 percent; and enhancing the subject's cognitive state during the application of the TES stimulation by performing one or more of: reducing the intensity by more than 20% of the target intensity, and, after a delay of less than 15 seconds, restoring the intensity to the target intensity at a rate of greater than a 5% change in intensity per second, increasing the frequency by more than 10% of the stimulation frequency, and, after a delay of less than 15 seconds, restoring the frequency to the target frequency at a rate of greater than 5% change in frequency per second, decreasing the duty cycle by 2% or more from the target duty cycle, and after a delay of less than 15 seconds, restoring the duty cycle to the target duty cycle at a rate of greater than 0.5% per second, or modifying the DC offset to +/−5% from the target DC offset, and after a delay of less than 15 seconds, restoring the DC offset to the target DC offset at a rate of greater than 1% per second.

Any of these methods may include placing a first electrode of a TES applicator on the subject's skin and placing a second electrode of the TES applicator on the subject's skin, wherein delivering TES stimulation comprises applying the TES stimulation between the first and second electrodes. In any of the methods described herein, delivering a TES stimulation may include delivering the TES stimulation for more than 10 seconds (e.g., for more than 30 seconds, for more than 1 minute, for more than 2 minutes, for more than 5 minutes, for more than 10 minutes, for more than 12 minutes, for more than 15 minutes, for more than 20 minutes, for more than 25 minutes, for more than 30 minutes, etc.). Also, any of the methods described herein may be useful to modify any appropriate cognitive state, including, for example, a calm or relaxed mental state or an alert or focused metal state.

As mentioned, any of these methods may also be driven by the subject himself or herself triggering the enhanced cognitive state. For example, enhancing the subject's cognitive state may comprise the subject triggering the start, triggering ramping (to enhance the stimulation), the subject modifying the waveform, etc. For example, the subject may trigger the ramping (excursion) described above to enhance the experience of the induced cognitive effect, or the ramping may be triggered automatically. Triggering the ramping described above may be referred to as boosting the induced cognitive effect.

For example, in one variation a boost to the induced cognitive effect may be triggered (e.g. by a subject), wherein the apparatus reduces the intensity by more than 50% of the target intensity (suprathreshold stimulation parameters) and, restores the intensity comprises restoring the intensity to the target intensity at a rate of greater than a 50% change in intensity per 500 ms.

In general, although precise supra threshold stimulation parameters may be subject-dependent, and may be empirically determined, described herein are generic suprathreshold parameters that can be generally applied, and may be referred to as target stimulation parameters, including a target intensity of about 3 mA or greater, a target frequency of about 400 Hz or greater, a target duty cycle of 10% or greater, and a target DC offset of greater than about 10%.

For example, increasing the frequency and restoring the frequency may include restoring the frequency to the target frequency at a rate of greater than 50% change in frequency per 500 ms. Decreasing the duty cycle and restoring the duty cycle may comprise restoring the duty cycle to the target duty cycle at a rate of greater than 15% per 500 ms. Modifying the DC offset and restoring the DC offset may comprise restoring the DC offset to the target DC offset at a rate of greater than 15% per 500 ms.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A and 1B illustrate placement of first electrode in the temple region of a subject's head. FIG. 1C shows alternative variations of the temple electrode placement. FIG. 1D illustrates a schematic representation of exemplar electrode placement for a temple electrode. The temple electrode placement shown may be used with another electrode placed in another part of the subject's body for TES modulation of cognitive state.

FIG. 3A illustrates the back of the neck region for placement of an electrode, which may be used in conjunction with a second electrode such as the temple electrode shown in FIG. 1A-1D. FIGS. 3B and 3C illustrate examples of this electrode placement showing an electrode positioned off-center on the back of the neck.

FIGS. 4A-4C illustrate exemplary electrode placement positions on a subject's head (shown in the context of a 10/20 system of positions) for another configuration ("configuration 1" for enhanced attention, alertness, or mental focus.

DETAILED DESCRIPTION

Figure 2A:
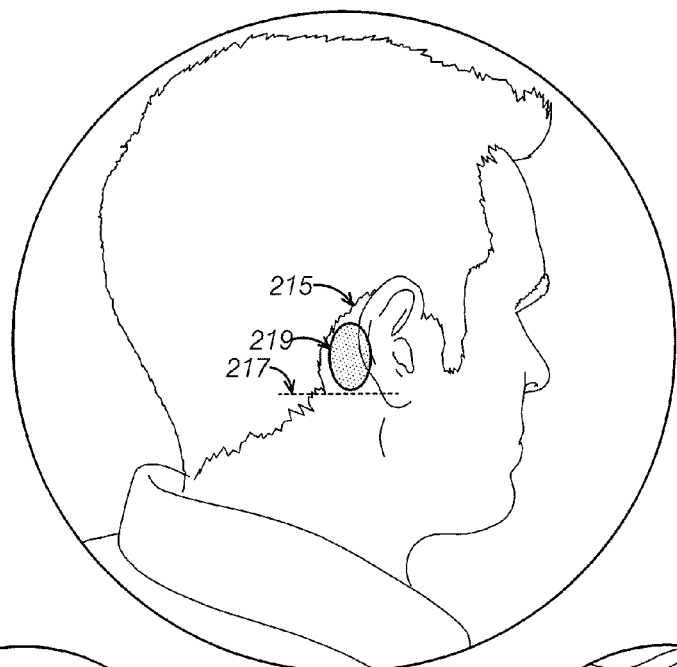
FIG. 2A illustrates the mastoid region for behind-the-ear placement of an electrode, which may be used in conjunction with a second electrode such as the temple electrode shown in FIG. 1A-1D.

Described herein are transdermal electrical stimulation (TES) methods and apparatuses, including devices and systems, such as TES applicators for modifying a subject's cognitive state. In general, these applicators and methods for TES may induce neuromodulation with electrical stimulation delivered to a human subject to induce a beneficial or desired change in cognitive function and/or cognitive state. Other examples of devices and methods for transdermal electrical stimulation (including transcranial electrical stimulation) are described in U.S. patent application Ser. No. 14/091,121 by named inventors of this application titled "Wearable transdermal electrical stimulation devices and methods of using them" and is incorporated in its entirely herein.

In general, described herein are general TES waveforms parameters that may be used to invoke, enhance, or modify a variety of cognitive states. Although the apparatuses and methods described herein may be used to provide TES to induce and/or modify a variety of cognitive states, two particular examples are described in detail herein, including inducing enhancing attention, alertness, or mental focus and inducing a calm or relaxed mental state. Configurations of apparatuses and methods specific to enhancing attention, alertness, or mental focus and inducing a calm or relaxed mental state, including specific configurations for causing neuromodulation that achieves one of these particular cognitive effects in a subject are described in particular detail.

A generic TES applicator (device or system) for modifying a cognitive state may include a pair of two electrodes (or two sets of electrodes), one anode and one cathode, that can be applied to specific regions of the subject's body and used to provide TES stimulation within the relatively high-intensity, high-frequency ranges described as effective herein. Current is typically applied between the anode and cathode electrodes (or groups of anodes and cathode electrodes); without being bound by a particular theory of operating, the current may be passed through the body between the anode and cathode, potentially applying energy in an appropriate treatment regime to underlying neural tissue (cranial nerves, brain, etc.) in a particular neural pathway to result in the desired target effect (e.g., attention, alertness, or mental focus and inducing a calm or relaxed mental state). Thus, the placement locations of the electrodes on the subject's body are important to provide the desired cognitive effect. The placement positions for the pairs of electrodes (anodal and cathodal electrodes) specific to a desired cognitive effect may be referred to as a placement regime or configuration. For example, a first placement configuration for inducing a cognitive state of attention, alertness, or mental focus, which may be referred to as "configuration A" or "configuration 2" includes a first electrode applied to the subject near the temple area (e.g., laterally to the eye, such as slightly above and to the right of the right eye or above and to the left of the left eye) and a second electrode positioned behind the ear on the same side as the first electrode in the mastoid region (e.g., on or near the mastoid). High-intensity TES stimulation (as described in greater detail below) of this region may result in enhanced attention, alertness, or mental focus. A second configuration (referred to for convenience herein as "configuration C" or "configuration 1") for enhanced attention, alertness, or mental focus may include placement of a first electrode on the temple area (e.g., laterally to the eye, such as slightly above and to the right of the right eye or above and to the left of the left eye) and a second electrode positioned on the forehead, e.g., near or above the nasion).

For example, TES using configuration A to enhance attention, alertness, or mental focus may result in: enhanced focus and attention; enhanced alertness; increased focus and/or attention; enhanced wakefulness; increased subjective feeling of energy; increased objective (i.e. physiological) energy levels; higher levels of motivation (e.g. to work, exercise, complete chores, etc.); increased energy (e.g., physiological arousal, increased subjective feelings of energy); and a physical sensation of warmth in the chest.

Another configuration (referred to herein for convenience as "configuration B" or "configuration 3") may include an electrode positioned on the subject's skin near the subject's temple area (e.g., above and to the right of the right eye) and a second electrode on the subject's neck (e.g., on a superior portion of the neck centered to the right (or left) of the midline and partially overlapping the spinal cord). TES stimulation of this region may result in enhancing a calm or relaxed mental state.

TES using Configuration B may result in cognitive effects including, but not limited to: a state of calm, including states of calm that can be rapidly induced (i.e. within about 5 minutes of starting a TES session); a care-free state of mind; a mental state free of worry; induction of sleep; a slowing of the passage of time; enhanced physiological, emotional, or and/or muscular relaxation; enhanced concentration; inhibition of distractions; increased cognitive and/or sensory clarity; a dissociated state; a state akin to mild intoxication by a psychoactive compound (i.e. alcohol); a state akin to mild euphoria induced by a psychoactive compound (i.e. a morphine); the induction of a state of mind described as relaxed and pleasurable; enhanced enjoyment of auditory and visual experiences (i.e. multimedia); reduced physiological arousal; increased capacity to handle emotional or other stressors; a reduction in psychophysiological arousal as associated with changes in the activity of the hypothalamic-pituitary-adrenal axis (HPA axis) generally associated with a reduction in biomarkers of stress, anxiety, and mental dysfunction; anxiolysis; a state of high mental clarity; enhanced physical performance; promotion of resilience to the deleterious consequences of stress; a physical sensation of relaxation in the periphery (i.e. arms and/or legs); and a physical sensation of being able to hear your heart beating.

In general, cognitive effects may be stereotypical across a population (though with individual variation and degree) and may be demonstrated by any appropriate means. For example, the effect of neuromodulation according to configuration A or configuration B (or any other Configuration) may be detected by one or more method chosen from the group including, but not limited to: subjectively by the recipient as a perception, movement, concept, instruction, other symbolic communication by modifying the recipient's cognitive, emotional, physiological, attentional, motivational, or other cognitive state; (ii) through physiological measurement of brain activity by one or a plurality of: electroencephalography (EEG), magnetoencephalography (MEG), functional magnetic resonance imaging (fMRI), functional near-infrared spectroscopy (fNIRS), positron emission tomography (PET), single-photon emission computed tomography (SPECT), computed tomography (CT), functional tissue pulsatility imaging (fTPI), xenon 133 imaging, magnetic resonance spectroscopy (MRS), or other techniques for measuring brain activity known to one skilled in the art; and (iii) by making a physiological measurement of the body such as by electromyogram (EMG), galvanic skin response (GSR), electrocardiogram (EKG), pulse oximetry (e.g. photoplethysmography), heart rate, blood pressure, respiration rate, pupil dilation, eye movement, gaze direction, measurement of circulating hormone (e.g. cortisol or testosterone), protein (e.g. amylase), or gene transcript (i.e. mRNA); and other physiological measurement.

For both Configuration A and Configuration B, the first electrode may be either an anode or a cathode. For convenience, the first (temple) electrode may be referred to as the anode. The anode (or set of isoelectric anodes) in all of configurations A, B and C may be positioned at the right temple, above and to the right of the right eye, between the eyebrow and hairline. Two exemplary electrode placements are shown in FIGS. 1A and 1B for an electrode assembly having connector between TES apparatus and an anode-cathode pair 104, wire to second electrode 103 (second electrode not shown), plastic backing 101 (top, away from skin), active electrode region 102 (i.e. for conducting current transdermally), and adhesive hydrocolloid region (bottom, adherent to skin). In this example, the bottom edge of active electrode region 102 is approximately aligned with a line running between the nasion and top of the ear 105. The nearest edge of the active electrode region may be at least about 0.5 cm from the eye (and optimally at least about 1 cm from the eye) to prevent distracting and uncomfortable eye muscle twitching caused by TES waveforms delivered (see FIG. 1D). Line running between eye and edge of active electrode region 107 indicates a beneficial distance between the edge of the electrode and the eye. FIG. 1A show a first effective orientation rotated counter-clockwise relative to a second effective orientation in FIG. 1B. The electrode angles are represented schematically by arrows 106. For subjects with a low hairline, the positioning of FIG. 1B may be preferred to avoid placing adhesive or electrode overlaying hair. The approximate location of the active electrode region is shown schematically in FIG. 1C for the position of FIG. 1A (109) and FIG. 1B (108).

For configurations A, B, and C, the anode electrode area may generally be greater than about 5 cm$^2$ and may be somewhat larger (i.e. greater than about 7 cm$^2$; greater than about 10 cm$^2$; or greater than about 15 cm$^2$. Larger electrode areas than 20 cm$^2$ (e.g., composed of a single anode or set of anodes) may be less effective for inducing the cognitive effects associated with configurations A, B, and C than smaller electrodes due to less precise targeting of electric fields delivered transdermally. Effective electrode shapes for these configurations may be generally longer than wide, including but not limited to rectangles, ovals, and irregular oblong shapes.

Figure 2B:
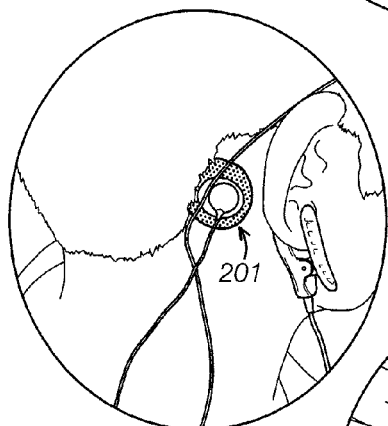
FIGS. 2B-2D show other variations of mastoid electrode placement for TES modulation of cognitive state.
Figure 2C:
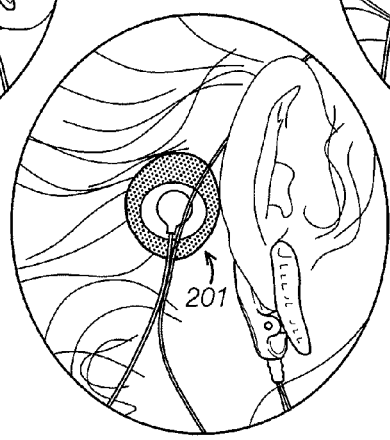
Figure 2D:
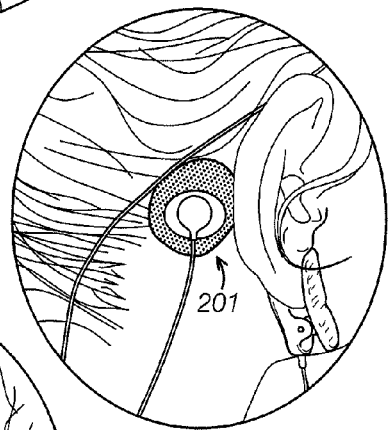

The second electrode position for configuration A may (for convenience) be referred to as a cathode (or set of isoelectric cathodes) covering most of the right mastoid process, behind the right ear (FIG. 2A). Preferably, the second electrode for configuration A should not touch the back of the ear. An effective electrode shape for the cathode (or set of cathodes) of configuration A may be round or oval with a diameter between about 0.5" to 1"—or may have an irregular shape to fit the mastoid area more effectively (i.e. a crescent shape). Conformable electrodes are preferred for making uniform (or near uniform) contact with the skin over the mastoid. In some cases the transdermally contacting portion of the cathode may be somewhat larger, particularly in the vertical dimension but is generally limited in size by the presence of hair above and behind the mastoid process. In FIG. 2A, the electrode may extend from the upper region of the mastoid region 215 to a lower region 217 (see oval region 219). The center of this electrode may be aligned with the ear canal, or it may be shifted up or down by about 5 mm, depending on the hairline and mastoid bone location of the subject. As with the first electrode, the hair may be avoided. FIGS. 2B-2D illustrate other positioning variations within acceptable ranges.

Figure 2E:
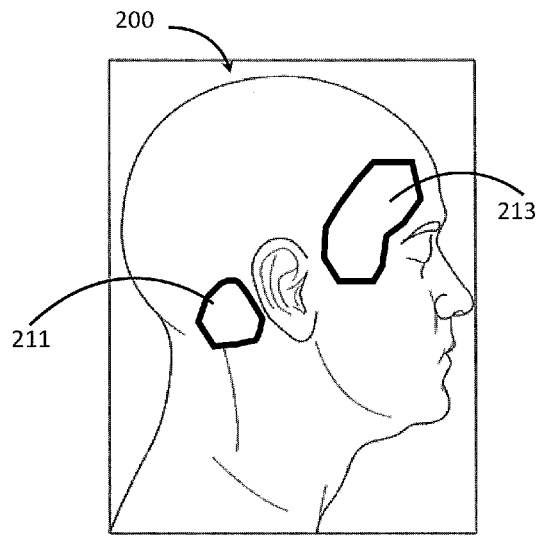
FIG. 2E illustrates the electrode placement regions for a configuration (configuration 2) to evoke a cognitive state of attention, alertness, or mental focus.
Figure 2F:
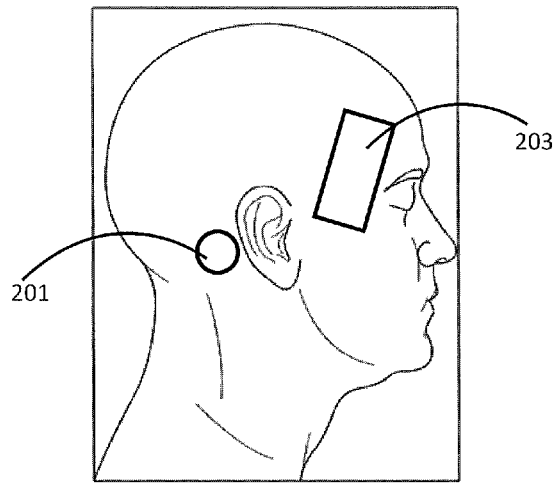
FIGS. 2F-2H schematically illustrate electrodes placed per this configuration.
Figure 2G:
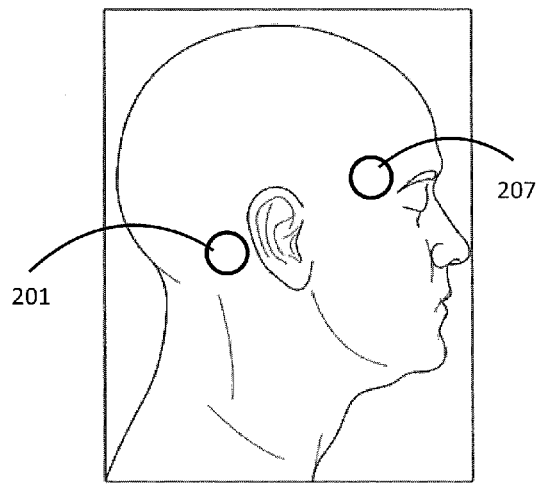
Figure 2H:
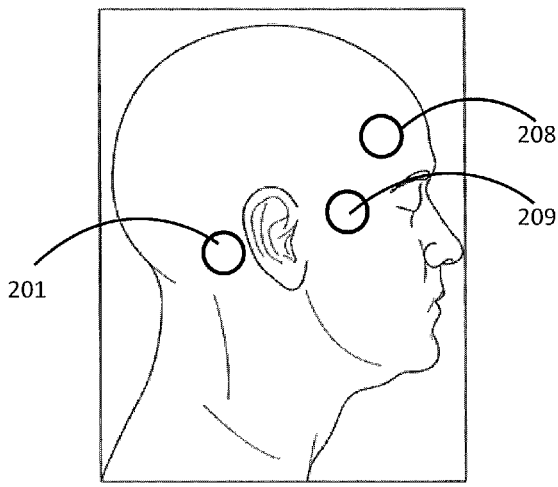

FIGS. 2E-2H illustrate other examples of electrodes and electrode placement for configuration A. In FIG. 2E a subject's head 200 is shown with the regions for temple electrode placement 213 and mastoid region electrode placement 211 outlined. FIG. 2F illustrates an example of a rectangular electrode at the temple 203 and a circular electrode 201 at the mastoid region. Similarly, in FIG. 2G, the temple electrode 207 is circular. FIG. 2H illustrates an example having two circular electrodes 208, 209 that may be configured as anodes (or both as cathodes).

Figure 3D:
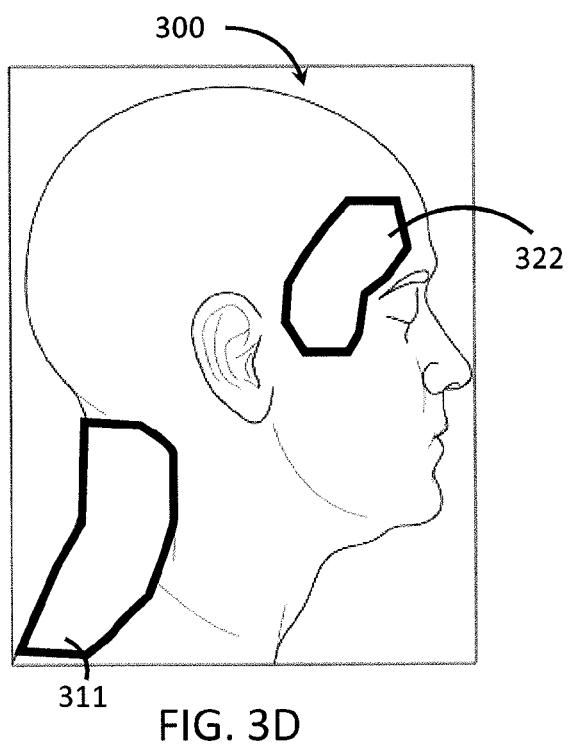
FIG. 3D shows electrode placement regions for a configuration (configuration 3) for enhancing a calm or relaxed mental state, including placing the TES electrodes on the back of the subject's neck and at the temple region.

In addition to the first, temple-positioned electrode, configuration B uses a second electrode (or set of isoelectric electrodes, e.g., for convenience referred to as cathodes) 301 placed on the superior portion of a subject's neck (i.e. with the superior edge of the electrode at or near the edge of a user's hairline) at the midline or, optimally, shifted to the subject's right by up to about 2 cm as shown in FIGS. 3A-3C. The electrode size for the cathode (or set of cathodes) of configuration B preferably has an area greater than about 10 cm$^2$; or optimally greater than about 15 cm$^2$; or optimally greater than about 20 cm$^2$. Electrodes for configuration B greater than about 40 cm$^2$ may be less effective for inducing the desired cognitive effect from neuromodulation due to less precise targeting of electrode fields into the body. The cathode (or set of cathodes) for configuration B may be round, oval, square, rectangular, or another regular or irregular shape. The second electrode position 301 in FIGS. 3A-3C are shown shifted to the right; in general, the second electrode may be off-centered from the neck midline (dashed vertical line 315 in the same direction as the side of the subject that the temple electrode is placed (e.g., right or left). Thus, the position of the second electrode is slightly to the right or to the left of off-center. Vertically on the subject's neck, the electrode may be positioned between the base of the hairline and the upper extent of the vertebra prominens 319 (e.g., closer to the hairline, such as above the region where the neck starts to curve into the shoulders 317). FIGS. 3B and 3C show alternative examples of position of the electrode 301 on the neck, each for a subject wearing the temple electrode on their right side. FIG. 3D illustrates the approximate regions for electrode placement of configuration B. In FIG. 3D, the electrodes may be placed in the temple region 322 of the subject 300 as well as on the back of the neck 311.

Electrode positioning for the anodes and cathodes of both configurations may be beneficially selected to be in areas that have minimal or no hair so that low impedance and uniform electrical contact can be made to the skin without requiring messy gel or saline. For example, beneficial electrode configurations may comprise electrodes sized such that the current density is less than 2 mA/cm$^2$.

Figure 4D:
FIG. 4D illustrates one example of the configuration shown in FIGS. 4A-4C.

FIGS. 4A-4D illustrate electrode positions for configuration 1 (configuration C). Electrodes placed on the head according to configuration 1 can be used as part of a TES system for delivering electrical stimulation to increase attention and/or alertness. The default mode network (a distributed functional network in the cerebral cortex) exhibits reduced activity during sustained attention and increased activity during mind-wandering & daydreaming. The right anterior insula and frontal operculum (along the inferior frontal gyrus) have been identified in functional magnetic resonance imaging (fMRI) studies as brain regions activated during sustained attention. The placement of electrodes in this configuration may increase the activity of areas near the right inferior frontal gyrus (including the right insula) and reduce activity in the default mode network, but other brain regions may be activated, inhibited, or modulated in at least some instances. A first electrode may be placed over the right inferior frontal gyrus near position F8 on the 10/20 standard and a second electrode near position AFz. FIG. 4A-4C shows exemplar placements of anode and cathode electrodes according to configuration 1 on schematics showing 10/20 electrode locations 401. The approximate center of anode 402 is shown with a plus sign in a circle and the approximate center of cathode 403 is shown with a minus sign in a circle. An exemplar electrode location is shown on subject's head 400. Rectangular anode electrode 406 is indicated with a plus sign and cathode electrode 405 is indicated with a minus sign. Note anode wire 407 that connects the electrode to a portable handheld tDCS unit. In a preferred embodiment, larger electrodes (about 1" by about 2" or larger) are effective in configuration 1. In some embodiments, a single larger anode is replaced by two or more smaller anodes placed near 10/20 position F8. In at least some instances a larger anode electrode is used that extends from just below eye-level upwards laterally of the right eye (ranging from F10 to F6 on the 10/20 system). The placement of the cathode is approximately over the midline at the center of a user's forehead.

Figure 4E:
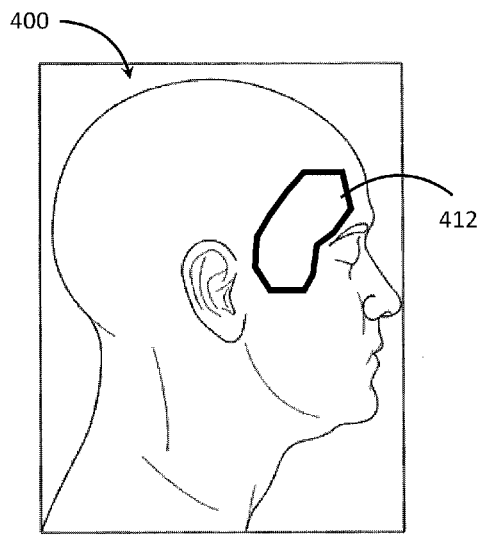
FIGS. 4E and 4F show the temple and forehead, respectively, of one example of electrode placement regions for configuration 1.
Figure 4F:
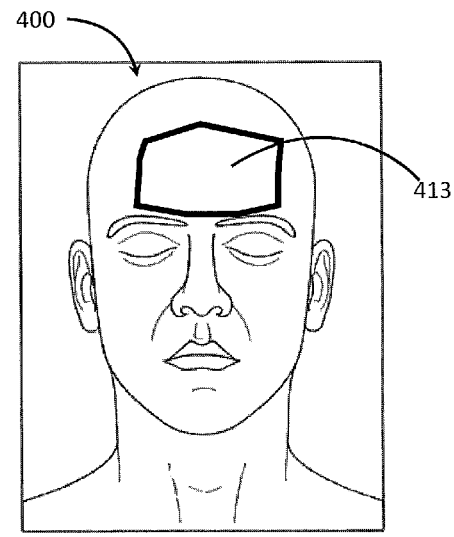
Figure 4G:
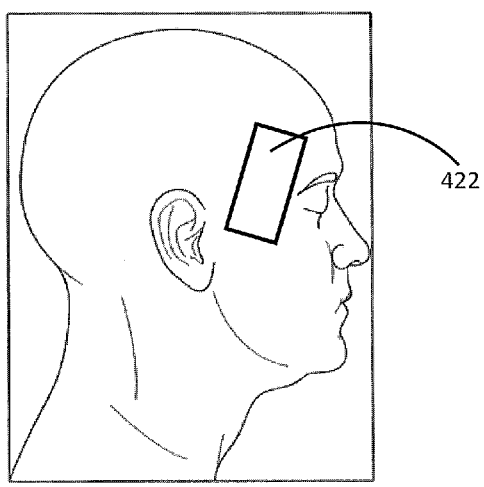
FIGS. 4G and 4H illustrate a subject with electrodes positioned per this configuration.
Figure 4H:
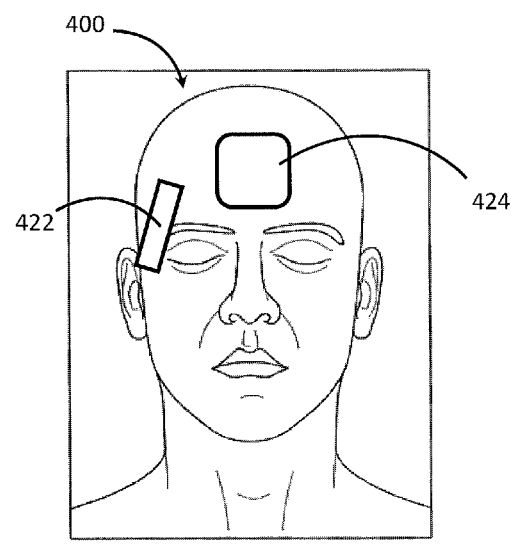

FIGS. 4E-4H show different variations of electrodes placed according to configuration C. FIGS. 4E and 4F illustrate approximate regions on a subject's head 400 where electrodes may be placed. In FIG. 4E the temple region 412 is illustrated, while in FIG. 4F the forehead region 413 is shown. FIG. 4G shows an approximately rectangular electrode 422 positioned at the temple location and FIG. 4H shows both the temple electrode 422 and a rounded square forehead electrode 424.

Any of the electrode configurations described herein can be achieved with adherent electrodes placed on the skin of a subject; non-adherent electrodes (e.g. saline-soaked sponges) held in low impedance contact with the skin of a subject by a wearable assembly (e.g. hat, headband, armband, or other wearable attachment system, which itself may be adherent, even if an electrode of the system is non-adherent); or a combination of adherent and non-adherent electrodes whereby a first set of electrodes are adherently attached to a subject and a second set of electrodes are non-adherently attached to the subject. Adherent electrodes are convenient because they can be configured to be removed while leaving minimal residue on the skin of the subject and to deliver TES to the subject without addition saline or gel. Non-adherent electrodes (e.g. saline-soaked sponges or gel-based electrode systems) are useful on hairy areas of the head, face, and body because a low impedance contact can be made through the hair with the conductive liquid or gel. The TES electrodes are electrically coupled to TES control circuitry that supplies appropriate electrical stimulation waveforms to the at least two electrodes. In embodiments using adherent electrodes, the TES control circuitry can be a component of the adherent assembly that contains the at least one electrode. In alternative embodiments using adherent electrodes, the TES control circuitry is contained in a separate assembly from the electrodes and connected by wires to the power and control circuitry.

In some embodiments, a single anode or cathode electrode can be replaced by a larger number of electrically continuous electrodes (i.e. replacing a single large anode electrode with two smaller anode electrodes placed in proximity to each other). The size and shape of each electrode used is a parameter that allows control over the area of stimulation delivered and the level of pain or irritation perceived by a subject. In some embodiments, each electrode position for a given configuration can be one electrode or more than one electrode positioned in a target area and conductively connected to each other (optionally at least 2 electrodes, optionally at least 3 electrodes, optionally at least 4 electrodes, optionally at least 5 electrodes, optionally at least 10 electrodes, optionally at least 25 electrodes, optionally at least 50 electrodes, optionally at least 100 electrodes, or optionally at least 1000 electrodes).

In general, peak stimulation intensities above at least 3 mA may be advantageous for transdermal electrical stimulation that causes neuromodulation by targeting the brain, nerves (e.g., cranial nerves, vagal nerve, peripheral nerves), and/or spinal cord. To achieve these peak intensities without causing pain, irritation, or discomfort in a subject may require appropriate electrodes and TES waveforms. Beneficial electrodes may have pH buffering properties and may contain components for uniformly (or more uniformly) delivering current across the dermal-facing portion of the electrode.

Functional lateralization is present in the human brain. The degree and side of functional lateralization can vary between individuals. For instance, left-handed people and women may have a lower degree of lateralization than right-handed men. For each of the configurations described above for the right side of the head and neck, electrodes placed at similar locations on the left side of the head and neck or both sides of the head may be as effective or more effective for some subjects.

In some users, improved efficacy may occur for electrodes placed on the left side of the user's head and neck; for two sets of electrodes placed bilaterally and connected so that anode-cathode pairs are unilateral; or for two pairs of electrodes placed bilaterally and connected so that anode-cathode pairs are transhemispheric. In embodiments with two sets of electrodes positioned bilaterally, the laterality of stimulation can be configured to be: constant for a particular session (e.g. only right side, only left side, or bilateral); selected automatically according to a measurement of a user's physiology or cognitive state; user-selected; switched between unilateral anode-cathode pairing and transhemispheric anode-cathode pairing; or varying over time. In some embodiments wherein the laterality of stimulation is time varying, stimulation alternates between one configuration of stimulation and another (e.g. right side stimulation for a period of time, then left side stimulation for a period of time—or unilateral stimulation through bilateral sets of electrode for a period of time followed by transhemispheric stimulation through bilateral sets of electrode for a period of time).

Multiple anode-cathode electrodes pairs positioned according to one of the configurations described herein may use identical stimulation protocols. Multiple anode-cathode electrodes pairs positioned according to one of the configurations described herein may use a stimulation protocol that differs in at least one parameter selected from the list including but not limited to: current intensity, waveform, duration, and other stimulation parameter. One of ordinary skill in the art would appreciate there are many positions in which the electrodes could be functionally arranged, and embodiments of the present invention are contemplated for use with any such functional arrangement.

In general, the TES waveforms for use with any of the configurations described herein may be a pattern of currents delivered into tissue of a subject (e.g. transdermally). Although there may be variations (optimizations) of these waveforms and electrical protocols for each configuration (electrode placement) and each target cognitive state, in general, the patterns may be within the same range of values to provide high-intensity, high frequency, high-duty cycle and not charge balanced (e.g., DC offset) signals that are applied to robustly evoke a response in most individuals while causing at most a low level (e.g. minimal or none) of discomfort and/or pain.

The time varying pattern of electrical stimulation delivered transcranially to induce neuromodulation may be referred to as a transdermal electrical stimulation waveform ('TES waveform'). A stimulation protocol may define the temporal pattern of current delivered to an anode-cathode set and can incorporate one or more waveform components including but not limited to: direct current, alternating current, pulsed current, linear current ramp, nonlinear current ramp, exponential current ramp, modulation of current (e.g. amplitude modulation at one or more frequencies), and more complex (including repeated, random, pseudo-random, and chaotic patterns). In operation, the device may provide current flow at target areas (e.g., in the brain, facial nerves, vagal nerve, or other neuronal targets) to induce neuromodulation when appropriate electrode configurations and stimulation protocols are delivered.

Figure 5A:
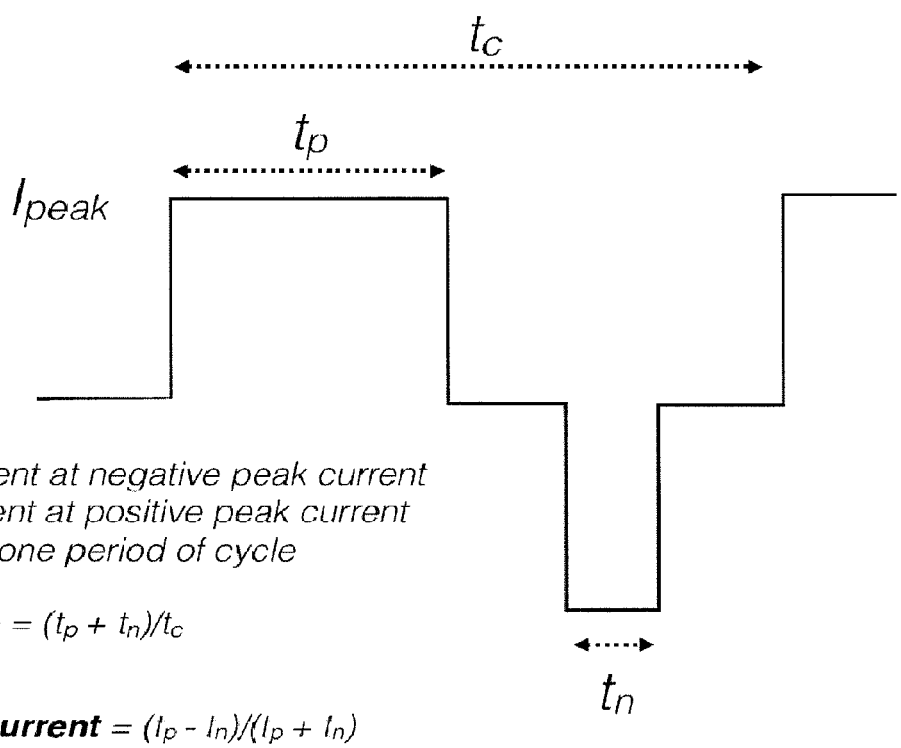
FIG. 5A schematically illustrates one example of a cycle of a transdermal electrical stimulation waveform and illustrates duty cycle percentage and percent direct current parameters of the TES waveform.

In general, a TES waveform may be defined by a duration, direction, peak current, and frequency. In some embodiments, a TES waveform is further defined by a percent duty cycle (FIG. 5A), percent direct current (FIG. 5A), ramping or other amplitude modulation, one or multiple frequency components, phase relationship of biphasic current, flat or structured noise, wave shapes (i.e. sawtooth, triangular, sine wave, square wave, exponential, or other wave shape), capacitance compensation features, or other parameters as discussed in U.S. patent application Ser. No. 14/091,121, titled "Wearable Transdermal Electrical Stimulation Devices and Methods of Using Them", filed on Nov. 26, 2013, which is herein incorporated by reference in its entirety. As used herein, 'percent duty cycle' may refer to the proportion of a cycle of a waveform that causes non-zero (or nominally non-zero) current to be delivered transdermally (see equation, FIG. 5A). Further, 'percent direct current' may refer to the non-zero portion of a waveform cycle that is positive-going (see equation, FIG. 5A).

Inducing significant, robust, and/or reliable cognitive effects typically requires an appropriate TES waveform defined by a set of parameters. A stimulation protocol ('TES waveform') may define the temporal pattern of current delivered to an anode-cathode set and can incorporate one or more waveform components including but not limited to: direct current, alternating current, pulsed current, linear current ramp, nonlinear current ramp, exponential current ramp, modulation of current, and more complex (including repeated, random, pseudo-random, and chaotic patterns). In operation, the device may provide current flow at target areas (e.g., in the brain) to induce neuromodulation when appropriate electrode configurations and stimulation protocols are delivered.

A set of waveform parameters may be selected based on the desired cognitive effect (e.g., configuration A, configuration B, etc.) and the number of electrodes, positions of electrodes, sizes of electrode, shapes of electrode, composition of electrodes, and anode-cathode pairing of electrodes (i.e., whether a set of electrodes is electrically coupled as an anode or cathode; also whether multiple independent channels of stimulation are present via current sources driving independent anode-cathode sets). Changing any of the features in the preceding list may require adapting a TES waveform by changing one or more parameters in order to achieve a desired cognitive effect.

Figure 5B:
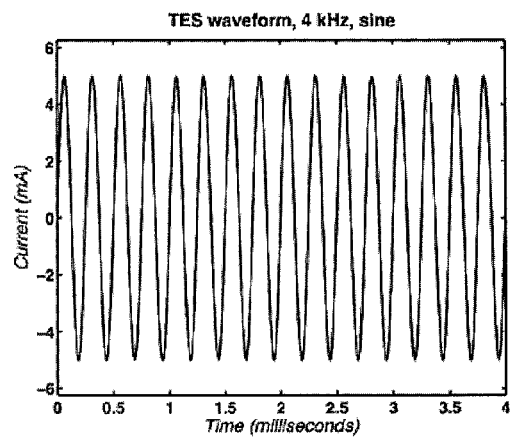
FIGS. 5B and 5C show exemplary biphasic waveforms for TES using a sine wave pattern or a square wave pattern, respectively.
Figure 5C:
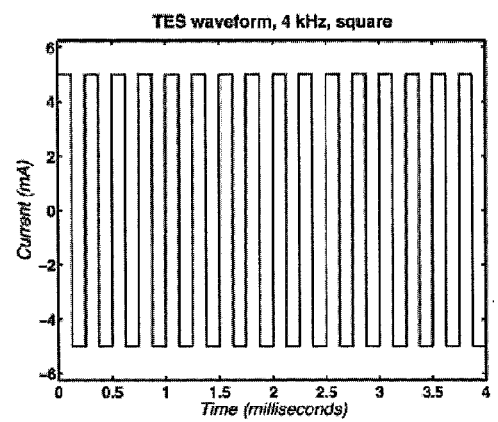
Figure 5D:
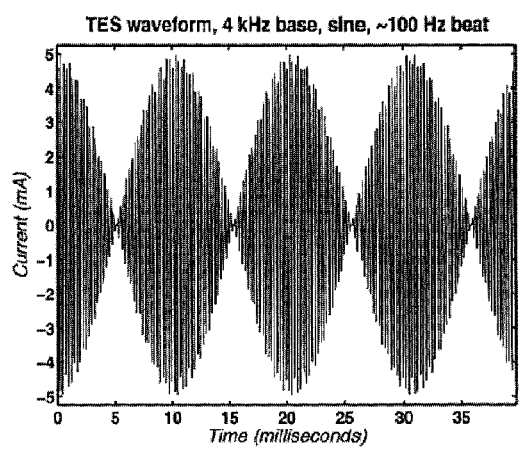
FIGS. 5D and 5E show two different temporal scales of a biphasic waveform for interferential transcranial alternating current stimulation.
Figure 5E:
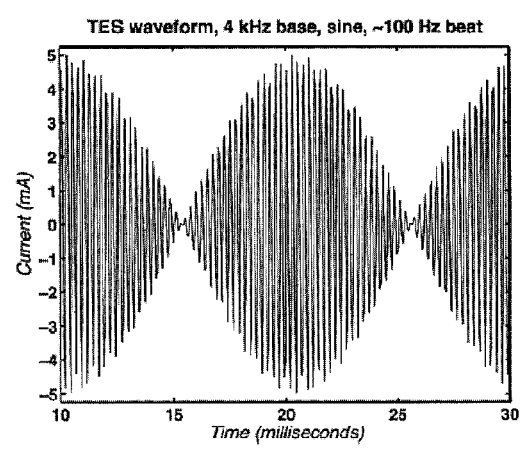
Figure 5F:
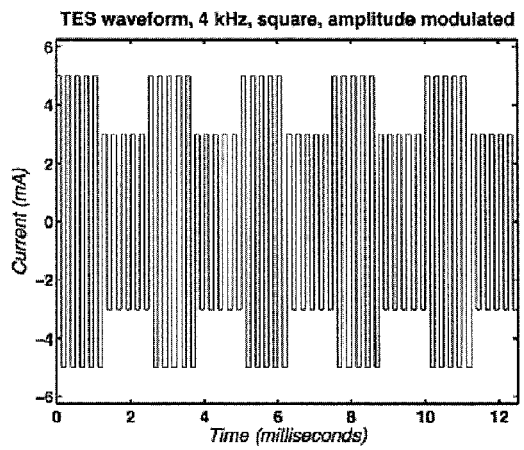
FIGS. 5F and 5G show TES stimulation waveforms for high frequency biphasic alternating current stimulation (square wave, amplitude modulated).
Figure 5G:
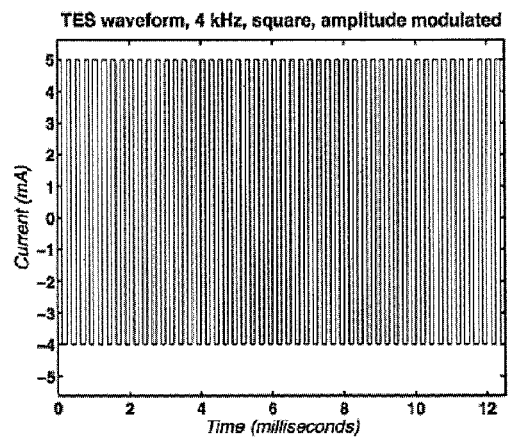

FIGS. 5B and 5C show an example of a sine wave (FIG. 5B) and square wave (FIG. 5C) at 4 kHz that maybe used to form the waveforms described herein. For example, FIGS. 5F and 5G show an example of a 4 kHz square wave with amplitude modulation (shown in FIG. 5F). FIG. 5G shows an example of a 4 kHz square wave with a direct current shift of 1 mA. Note that advantageous pulsing regimes can include amplitude modulation, frequency modulation, and other linear and nonlinear techniques for modulating an alternating current. For example, sine wave and square wave (e.g., 4 kHz waveforms) may be useful for TES stimulation as described herein. One example of an effective pulsing regime is 4 ms on, 16 ms off. Moreover, pulsing can be used to stimulate neural circuits at biologically relevant frequencies less than about 200 Hz.

Figure 5H:
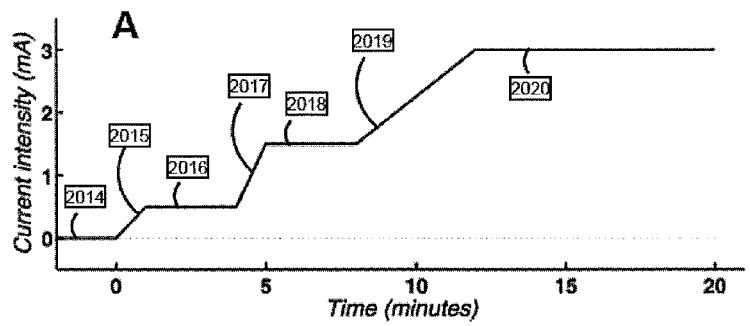
FIG. 5H shows an exemplary schematic of a ramp for gradually increasing the current intensity for TES as described herein.
Figure 5I:
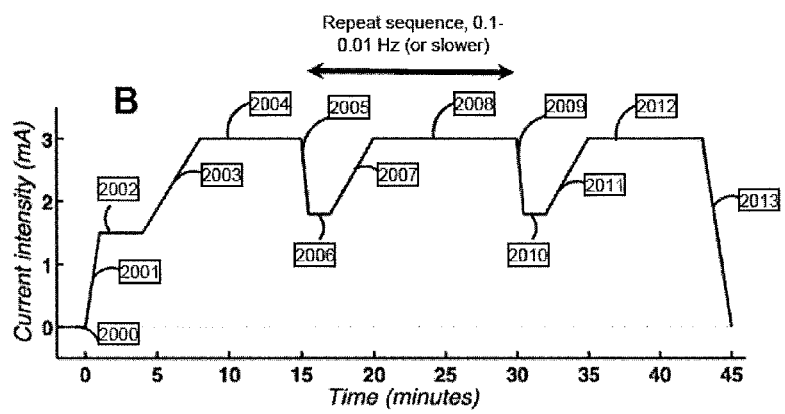
FIG. 5i shows an exemplary schematic of a treatment waveform protocol including multiple excursion stimulations (ramps) which may enhance the TES stimulation to modify a cognitive state.
Figure 5J:
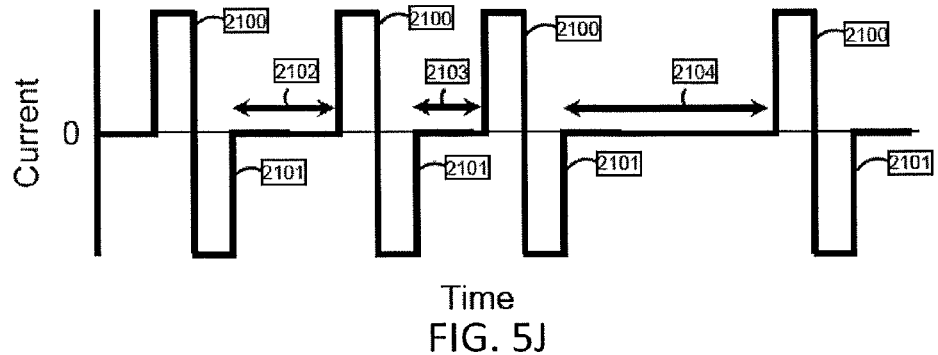
FIGS. 5J and 5K illustrate exemplary biphasic waveforms for TES (e.g., transcranial alternating current stimulation) to modify a cognitive state.
Figure 5K:
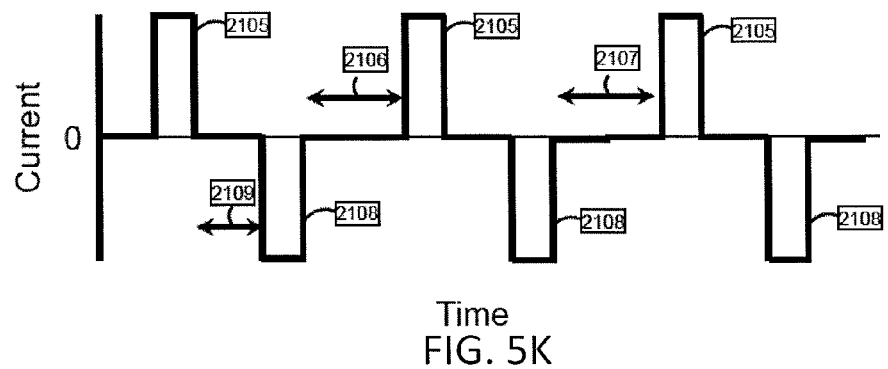
Figure 5L:
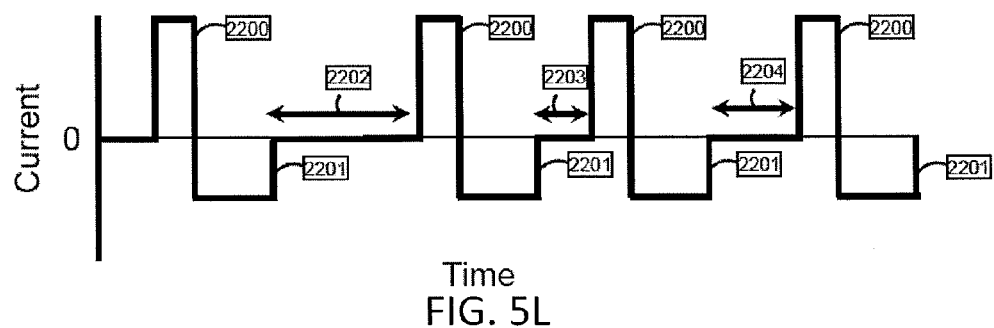
FIGS. 5L and 5M illustrate exemplary biphasic waveforms for TES to modify a cognitive state as described herein.
Figure 5M:
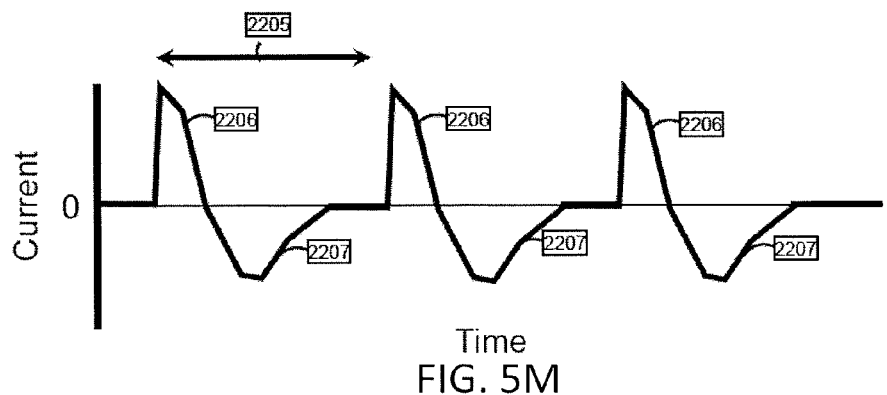

FIGS. 5J and 5K illustrate two pulsing strategies with zero net current. One pulsing strategy has negative-going phases 2101 that follow immediately after positive-going phases 2100 with variable inter-pulse intervals 2102, 2103, 2104 consistent with frequency modulation. In alternative embodiments, a constant inter-pulse interval is used. Another pulsing strategy separates positive-going pulse phase 2105 from negative-going pulse phase 2108 by intervals 2106, 2107, 2109. FIGS. 5L and 5M show two additional pulsing strategies with zero net current. One pulsing strategy has brief, high-current positive-going phase 2200 followed by longer, lower-current negative-going phase 2201 and variable inter-pulse intervals 2202, 2203, 2204. Another pulsing strategy delivers non-square waveforms with positive going phase 2206, negative-going phase 2207, and interval between the start of pulses 2205.

For high frequency biphasic stimulation, current intensity can be ramped up very quickly without discomfort relative to direct current stimulation. This feature is advantageous for being able to induce beneficial cognitive effects quickly without painful, irritating, or distracting side effects. Accordingly, changes in cognitive state are more immediate for high frequency biphasic alternating current stimulation as described here than for tDCS.

An alternative strategy for pain relief may include the use of interferential stimulation. Interferential stimulation uses two anode-cathode pairs, for example, one pair at a constant 4 kHz and one pair at a variable frequency between about 4001 kHz and 4200 Hz. This produces a 'beat frequency' between 1 and 200 Hz in the tissue beneath the electrodes, which is intended to reduce pain transmission. The advantage of this method over stimulation via one anode-cathode pair at 1-200 Hz is that uncomfortable sensory side effects of stimulation may be minimized. For interferential stimulation, the 'beat frequency' of between 1 & 200 Hz is the important frequency for modulating pain and muscle fibers. The 'carrier frequency' of about 4 kHz reduces discomfort typically associated with applying high intensity stimulation between 1 and 200 Hz. In order to deliver a beat frequency to the brain of a subject, two channels (i.e. anode-cathode sets) are required (e.g. one channel delivering stimulation at 4000 Hz and a second channel delivering stimulation at 4100 Hz). FIGS. 5D and 5E shows two views of an iriterferential tACS waveform comprised of a 4000 Hz sine wave and a 4100 Hz sine wave.

The current threshold for inducing changes in mental state with a high-frequency biphasic stimulation protocol is between 3 and 10 mA or higher (higher than for tDCS in at least some cases), but using the stimulation protocols described herein, at these higher currents there may be much less tingling, itching, and burning than expected. In some variations, a net zero current waveform of the biphasic stimulation may reduce or eliminate skin irritation. However, as described herein, it may also be (surprisingly) beneficial to have biphasic current with a DC offset that would otherwise result in a charge imbalance; as described below, one or more techniques for reducing irritation (including removing capacitive charge by short-circuiting the electrodes) may be used. One possible side effect is muscle contractions, which can be noticeable at high currents (>6 mA) and which may be distracting for some users but are not painful. Up to 11 mA has been used without too much discomfort from muscle contractions, but muscle contractions typically become noticeable between 5 and 10 mA. Even higher frequencies (e.g. up to 50 kHz) can be used to prevent muscle contractions. Smaller electrodes (e.g. 1 square inch) may result in a lower threshold for muscle contractions and lower threshold for changes in mental state (presumably both effects are related to current density).

In some variations, low or zero net current may be an advantageous feature of biphasic high frequency TES, because skin irritation is directly related to pH changes under the electrodes, which is proportional to current density under the electrodes, and low net current may be similarly effective for reducing pain and irritation from pH changes in the skin. For instance, a DC offset similar to the threshold current density for getting skin irritation with DC (about 0.5 mA/cm$^2$ with Little PALS electrodes and about 0.2 mA/cm$^2$ with regular adherent skin electrodes) could be used together with high frequency alternating current stimulation (FIG. 5G) to provide TES with minimal irritation, pain, and tissue damage. However, as described above, in some variations, having a charge imbalance (e.g., a DC offset) is particularly effective, particularly in combination with 'short-circuiting' during stimulation to remove capacitive charge.

Preliminary data suggests a different 'rule' with pulsed stimulation than with DC stimulation. With DC stimulation in at least some instances, cognitive effects last throughout stimulation. With biphasic pulsed stimulation in at least some instances, the effects are much greater when you are raising and lowering the max amplitude current around a certain threshold value. With this protocol habituation does not occur in at least some instances. In at least some instances, the current can be increased and decreased repeatedly to induce desirable cognitive effects with each increase, but when you leave the amplitude at a certain value (even if that value is at threshold), the effects may subside. This finding inspired an additional embodiment wherein a secondary (slower) frequency modulates the amplitude of the high-frequency biphasic tACS (FIG. 5F). This slower modulation would sustain the effect by having frequent rises and dips above and below the threshold for sensations. In the example shown in FIG. 5F, the amplitude of the biphasic high frequency TES signal alternates between +/−5 mA (above threshold for a cognitive effect) and +/−3 mA (below threshold for a cognitive effect). Note that other patterns of amplitude modulation between suprathreshold and subthreshold current intensities can be used (e.g. linear or nonlinear ramping, sawtooth pattern, sine wave, or other amplitude modulation waveform).

In another alternative embodiment, high-frequency biphasic TES (e.g., tACS) may be applied to a subject to induce a desired cognitive effect, then the system switches to a DC mode of operation to sustain a cognitive effect. High-frequency biphasic TES may be applied concurrently with a DC offset or DC bias (of for example 0.5 mA or 1 mA) to induce large cognitive effects while at the same time reducing painful or irritating sensations (FIG. 5G).

Adherent, self-contained TES systems that apply one or more of the above pulsing, TES, and interferential stimulation strategies may be advantageous for achieving a desirable form of neuromodulation with minimal pain, irritation, and tissue damage.

TES systems that incorporate "short-circuiting" (e.g., discharging the capacitance on the electrodes) may be useful for pulsed stimulation regimes, and may help reduce or prevent pain and discomfort. In some variations the apparatus includes short circuiting (or capacitance discharging) circuitry in connection with the electrodes. For example, capacitance discharging circuitry may include electronic components and firmware features that short the anode-cathode path with a low ohm resistor (e.g. 50 Ohms) to permit discharge of capacitance that builds up during a pulse (e.g. in the subject's skin). In some instances, short-circuiting is beneficial for reducing discomfort and accordingly increasing the cognitive effects induced by TES (due to one or both of: reducing the distraction of discomfort so that other cognitive effects can be experienced by a subject and permitting higher peak current intensities to be delivered that induce more significant cognitive effects). Other systems and methods for rapidly discharging capacitive current to minimize side-effects that are irritating and thus distract from desired cognitive effects or mental states—or limited with regard to peak intensity delivered—may be used as an alternative to a short-circuiting mode and system as described. For example, a capacitive discharging circuitry may include a fixed current source similar to the main current source in the device, but saturating at 0V and allowing discharge of the accumulated charges. The discharge time may be fixed or may depend on the voltage and electrode capacitance. In one example a nominal short-circuit current may be adjustable (e.g., to 40 mA), which could be changed by changing a resistor. The discharge could be made by the regular current source with an adjustable current inside the range, e.g., up to 20 mA; turning on the two rectified bottom switches may avoid reverse charging in this case. In general, a short circuiting discharge can be very quick (e.g. on the microsecond timescale) and could use a very high current, e.g., tens of mA to 100 mA.

For both configuration A and configuration B described above, within a range of acceptable TES waveforms, changing one or more parameters may vary the modification of the cognitive state, e.g., changing the subjective experience of an induced cognitive effect. Some stimulation parameters may be more effective in one subject as opposed to another.

In general, ramping and other waveform features can be incorporated in order to shift a waveform between different effective ranges of parameters for inducing a particular cognitive effect and thus achieve a more intense, longer lasting cognitive effect. Shifting between effective waveforms may be iterative (i.e. one parameter changes, than another changes) and it may be repetitive (i.e. change from one waveform to a second waveform, then back to the first waveform, etc.; or toggling between three or more effective waveforms). In some embodiments, rapidly shifting one or more waveform parameters within an effective range induces a stronger cognitive effect, wherein rapid generally refers to less than 15 seconds and may be as short as one second or less.

In both configuration A and configuration B, biphasic TES waveforms (direct current <100%) for neuromodulation may have the center of the positive-going and negative-going pulses separated by 180 degrees in phase or may have a smaller phase offset so long as the positive-going and negative-going pulses are non-overlapping. In general, a TES waveform for any of the configuration described herein may be added, subtracted, convolved, or otherwise amplitude modulated. Moreover, in embodiments, a TES waveform for either configuration described herein may have its amplitude ramped using linear, exponential, or another ramp shape. Pulses of a TES waveform can comprise square waves, sine waves, sawtooth waves, triangular waves, rectified (uniphasic) waves, pulse-width modulated, amplitude-modulated, frequency-modulated, or other pattern of alternating current waveform.

Figure 6:
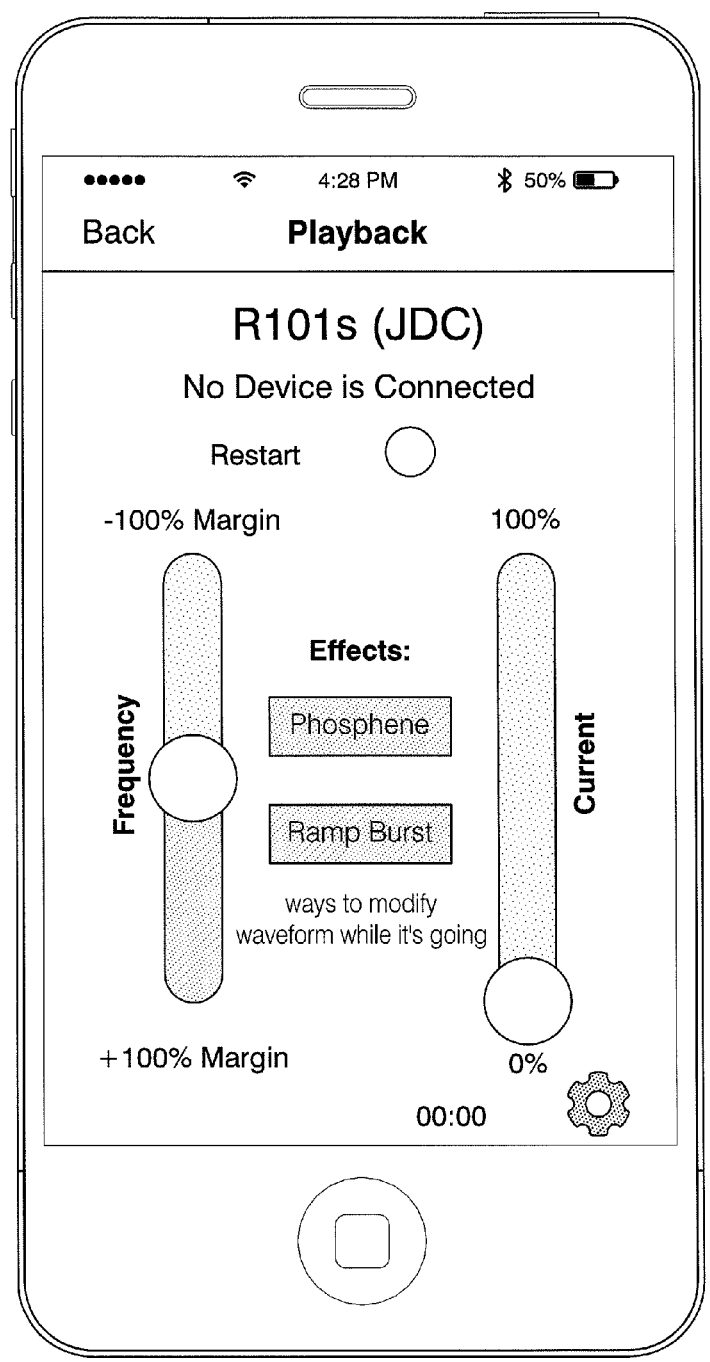
FIG. 6 illustrates one example of a handheld apparatus having a processor configured (e.g., containing a non-transitory computer-readable storage medium storing a set of instructions capable of being executed by the remote processor such as a smartphone or the like) to display user interface controls of TES waveform parameters.

The delivery of the waveform may start, pause, stop, or be modulated (e.g. a parameter of a TES waveform be changed) when a subject activates a user interface (a physical button, switch, or the like; or a non-transitory computer-readable storage medium storing a set of instructions capable of being executed by a remote processor (and particularly a smartphone or the like), when executed by the computing device containing the remote processor causes a user interface for commencing a TES waveform to be displayed on the screen of a TES apparatus or a computing device communicably connected to the TES apparatus). See, for example, FIG. 6, illustrating one example of remote processor that may be used to trigger stimulation of a wearable device worn by a subject. The remote processor may be a smartphone, and may communicate (two-way or one-way) with the device, for selecting the stimulation parameters, etc.).

Changes in cognitive state induced by TES can be difficult for a user to recognize subjectively and assign causally to the electrical stimulation. By incorporating intermittent, transient periods of reduced current intensity (increased frequency, reduced duty cycle, reduced DC offset, etc.), the cognitive change that occurred moments earlier is made apparent, improving the user experience and positive reaction to the system. In short, transiently (and quickly) decreasing and then increasing current intensity to create a stark subjective contrast for the subject may provide an induced cognitive effect at higher current level more obvious to a user. Accordingly, methods and systems that guide a user's perception of induced change in cognitive state by a TES session are beneficial. For example, after maintaining a current intensity above a threshold for inducing neuromodulation, suprathreshold level for inducing the cognitive effect, the current intensity may be rapidly (e.g. over less than 5 seconds; optionally over less than 10 seconds; optionally over less than 15 seconds) decreased below a threshold value for inducing a cognitive effect (subthreshold for inducing the cognitive effect), thereby causing a subject to more readily recognize an induced cognitive effect at the preceding higher current intensity.

An exemplary sequence can be described by the following four-steps: (1) rapid ramp down to an intermediate current intensity below that is below that required for an induced cognitive effect, (2) maintenance at the intermediate level for a period of time sufficient for the subject to recognize the absence of the previously induced change in cognitive state, (3) gradual increase in current intensity at a rate sufficiently slow such that the increasing current intensity is minimally irritating and/or painful for the subject, and (4) maintenance of a current intensity for TES that is sufficient to induce a cognitive effect of interest. The four-step sequence can be delivered a single time to a subject or repeated at a fixed or variable frequency chosen to be between about 0.001 Hz and 0.1 Hz.

For example, FIGS. 5H and 5i show exemplary patterns including both slow ramps (ramp on) and rapid ramps (transient excursions) to improve TES efficacy. In the example of FIG. 5i, current intensity starts at level of 0 mA 2000, increases linearly 2001 to intermediate sub-threshold (for neuromodulation to induce an intended cognitive effect in a subject) current 2002, then ramps up again 2003 to current 2004 that is above threshold for neuromodulation to induce an intended cognitive effect in a subject. Next, rapid decrease in TES current 2005 delivered occurs over a brief time period down to level of current intensity below the minimum for inducing the change in cognitive state 2006 that is maintained for a minute or two minutes before gradual increase in current intensity 2007 back to higher current level 2008 that is above threshold for neuromodulation to induce an intended cognitive effect in a subject. In this example, transient decrease in current intensity 2009, 2010, 2011, 2012 is repeated once before the current level is reduced back to 0 mA 2013. In some variations it has been found to be even more effective if the intensity is ramped down (subthreshold) either quickly or slowly, but the time to ramp back up to suprathreshold is much faster (e.g., less than a few seconds, etc.).

Sets of waveforms intended for use with the same electrode configuration may be used to induce cognitive effects that are sustained, more intense, or that provide a related but subjectively distinct experience (e.g. a first TES stimulation waveform may cause increased motivation while a second, related TES stimulation waveform induces an increase in mental clarity and focus). An apparatus (including the applicator and/or remote processor paired with the applicator) may include these various waveform sets and may be selected (and in some cases modified) by the subject.

One way to cause a sustained, longer-lasting cognitive effect in a subject is to deliver a first TES waveform that causes the induction of a desired cognitive effect, then delivering a second TES waveform following a pause after the first TES waveform. When the first TES waveform ends, the induced cognitive effect may endure for some period of time but gradually degrades in intensity or quality. A second TES waveform can then be presented that causes a boost or re-induction of the degrading cognitive effect caused by the first TES waveform. Generally, an induction protocol may be longer (i.e., one minute or longer; beneficially 3 minutes or longer; or 5 minutes or longer; or 10 minutes or longer) relative to the second TES waveform that will generally last seconds to minutes. This arrangement may be beneficial relative to simply re-triggering the first, longer TES waveform because it is more comfortable, more power efficient (so that the batteries on a TES system are longer lasting), and safer because it induces a similar cognitive effect while introducing less energy into the body.

For example, an 8 minute induction TES waveform configured for electrodes placed according to configuration A may be delivered transdermally to a subject, then some minutes to tens of minutes (or hours) after the end of the 'induction' TES waveform, a second TES waveform is selected to 'recharge' or 're-induce' the effect through a more brief (i.e., less than two minutes; or less than five minutes) TES waveform. The re-induction TES waveform is intended to be reused as needed by a user. In an embodiment for which a smartphone app is used by a subject to select an effect, a user interface element may be presented to the subject automatically at a particular time after the end of the first session so that the user may trigger a 're-induction' (or 'recharge') TES waveform matched to the first induction TES waveform.

Some methods for inducing 're-induction' or 'recharge' TES waveforms may permit a user to remove electrodes between the induction session and the recharge session (or between multiple recharge sessions) and optionally remind them to place the electrodes when it is time for recharge session. The timing of a recharge session may be determined purely based on time (i.e. open loop) or may be triggered automatically based on physiological, behavioral, cognitive, and/or other data and an appropriate algorithm that determines when an induced cognitive effect has worn off thus requiring a 'recharge' TES waveform.

Examples of effective TES waveforms to induce cognitive effects associated with configuration A may use pulsed biphasic stimulation waveforms (i.e. with stimulation in both directions during a cycle), though pulsed monophasic stimulation waveforms and alternating current stimulation waveforms may also be effective for inducing similar cognitive effects in at least some instances.

Pulsed biphasic stimulation may be effective for inducing the cognitive effects associated with Configuration A with a duty cycle between 30% and 50%. For example, a direct current percentage between 30% and 50%; a dominant frequency between 750 Hz and 6 kHz; and a minimum peak current intensity that is frequency-dependent and in the range of 3 mA to 16 mA. Peak intensity useful to induce the cognitive effects of configuration A may be approximately linearly proportional to the dominant frequency of the TES waveform. For example, to induce the cognitive effects of configuration A reliably across individuals the required peak currents may be: at least 3 mA at 750 Hz; at least 7 mA at 4 kHz; and at least 16 mA at 10 kHz. In general, a peak current of at least 3 mA is useful to robustly induce cognitive effects of configuration A. In general, as frequency increases, current to experience the effect may increase. However, the effective range for duty cycle and percentage direct current may not change as a function of stimulation frequency.

For devices with high voltage (e.g., at least 50V) and high power (e.g. at least 700 mW), there are also comfortable and effective waveforms with a dominant frequency component above 6 kHz. However, since frequency and current needed for the effect are approximately proportional, only a small percentage of the population with relatively low skin impedance (e.g., 10 kOhm or less)—estimated to be less than 20%—can achieve these effects with lower powered devices. When feasible, TES waveforms comprised of a dominant frequency above 6 kHz (i.e., between 6 kHz and 25 kHz; or between 6 kHz and 15 kHz; or between 10 kHz and 15 kHz) are also effective for inducing effects of configuration A. Since higher current intensities are required with increasing frequency, peak currents above about 7 mA (and preferably above about 10 mA) are required to induce effects of configuration A in this higher frequency range.

For devices configured with short-circuiting between pulses (which reduces capacitive charge buildup and thus increases comfort and reduces side effects), TES waveforms comprised of a dominant frequency in a lower frequency range in the traditional range of nerve stimulation (i.e. between about 80 Hz and about 150 Hz) can yield effective cognitive effects associated with Configuration A, possibly due to stimulation of the facial nerve. For TES waveforms comprised of a dominant frequency in this lower range, duty cycle and percentage direct current are optimally below about 30 percent.

As mentioned, in general, rapid ramps of stimulation frequency (e.g. occurring over less than 10 seconds and optimally over less than 3 seconds) within effective frequency ranges can induce stronger cognitive effects associated with configuration A. To improve comfort, it is generally preferred to use a peak current intensity at or near the lower end of the frequency range that is comfortable for a subject while shifting frequency. Repeated shifts in frequency may also be beneficial for inducing strong cognitive effects. For example, a shift from 2 kHz to 6 kHz then back to 6 kHz occurring over 3 seconds or less may be an effective TES waveform feature for improving the strength of cognitive effects associated with configuration A.

An exemplar effective TES waveform for inducing effects associated with configuration A lasts between five and 15 minutes with a 40% duty cycle, 38% direct current, a 10 mA peak intensity (which optionally increases gradually over the course of a waveform, e.g. from 8 mA to 10 mA), and a dominant frequency that shifts between 4 kHz and 6 kHz.

In general, a short-term increase in the level of cognitive effects associated with Configuration A can be achieved by transiently and rapidly modulating one or more parameters of stimulation, including increasing peak current; increasing duty cycle; and reducing stimulation frequency. However, modulating the percentage direct current is not a reliable way to increase the intensity of cognitive effects induced by configuration A. To achieve the desired short-term increase in cognitive effect requires modulating a TES waveform parameter that ideally occurs within 1 second, but up to 5 seconds can be somewhat effective. In general, a preceding (optionally occurring more gradually; i.e. overs 10 or more seconds up to minutes or longer) modulation of the TES waveform parameter in the opposite direction is required in order to deliver the modulation that causes the short-term increase in cognitive effect while remaining within an effective range for the modulated parameter. In general, rapid increases in current or duty cycle require a responsive TES current control circuit that can quickly recruit the needed higher power.

Effective TES waveforms to induce the 'relaxation' cognitive effects associated with configuration B may use pulsed biphasic stimulation waveforms (e.g., with stimulation in both directions during a cycle) or pulsed monophasic stimulation waveforms, though alternating current stimulation waveforms may also be effective for inducing similar cognitive effects in at least some instances. Pulsed biphasic stimulation may be effective for inducing the cognitive effects associated with configuration B with a duty cycle between 30% and 60%; a direct current percentage between 85% and 100% (where 100% direct current corresponds to a monophasic pulsed stimulation waveform); a dominant frequency between 5 kHz and 50 kHz (e.g., 5 kHz and 25 25 kHz; up to 50 kHz, etc.); and a peak current intensity between 1 mA and 20 mA (though in some instances higher peak intensities above 20 mA may also be effective if comfortable for the user).

TES waveforms that include cycles of lowering and increasing peak current may be beneficial for inducing cognitive effects associated with configuration B. For example, such a cycle may comprise 3 to 4 minutes at a high peak intensity (e.g. 15 mA) followed by a transient reduction to a lower peak intensity (e.g. 4 mA or lower) for a period between 10 seconds and 1 minute. For example, TES waveforms that have at least 3 cycles of reducing then increasing current intensity over a period of about 10 minutes are effective for inducing cognitive effects associated with configuration B. In general, shifts or ramps of a dominant stimulation frequency of about +/−1000 Hz while at peak current is another strategy for inducing strong cognitive effects associated with configuration B.

TES waveforms that incorporate gradual increases in effective intensity may be beneficial for enhancing cognitive effects associated with configuration B. Effective intensity can be increased by increasing peak current, lowering stimulation frequency, increasing duty cycle, increasing direct current percentage, or any combination thereof.

As mentioned above, TES waveforms delivered by a TES system with short-circuiting enabled (including capacitive discharging of the electrodes) may be a beneficial feature due to the high direct current percentages required to induce effects associated with configuration B. High direct current typically means more charge imbalance of stimulation and thus a higher capacitive load to discharge via a short-circuiting mode. However, in some instances, cognitive effects associated with configuration B may be induced without short-circuiting (e.g. with a TES waveform having parameters of: 2-4 kHz, 7-8 mA, 80% duty cycle, and 15% direct current).

An exemplar effective TES waveform for inducing effects associated with configuration B uses a 38% duty cycle, 100% direct current (monophasic pulses), a 16 mA peak intensity (which optionally increases gradually over the course of minutes of a waveform, e.g., from 14 mA to 16 mA), a dominant frequency of 7 kHz (that optionally shifts up and/or down by up to about 1 kHz during the waveform), and ramps down to and back up from 11 mA intermittently during the waveform.

Another exemplar effective TES waveform for inducing effects associated with configuration B uses a 44% duty cycle, 95% direct current, a 13 mA peak intensity (which optionally increases gradually over the course of minutes of a waveform, e.g. from 10 mA to 13 mA), a dominant frequency that modulates within a range of 7.5 kHz to 8.5 kHz, and intensity ramps down to and back up from 4 mA intermittently during the waveform.

In general, TES waveforms for inducing effects associated with configurations A and B are at least three minutes in duration (though 'recharge' waveforms as described herein may be shorter, e.g., tens of seconds or longer).

In general, the comfort of TES waveforms for inducing effects associated with Configurations A and B may be increased by having a gradual ramp from zero (or near zero) current to an effective current intensity so that the subject may habituate to the current.

In general, TES waveforms for inducing effects associated with configuration A or B may include shifts or ramps between parameter values within effective ranges. Gradual increases in intensity over minutes of a TES waveform for configuration A or configuration B (e.g., from 8 mA to 10 mA over 10 min) are beneficial for inducing robust and/or long-lasting effects since subjects tend to initially be very sensitive to the side-effects but later adapt to the side-effects.

Applicators

The methods of modifying a subject's cognitive state described above may be implemented by a variety of different devices, such as TES applicators. In general, a TES applicator may include hardware and software system for TES such as: a battery or power supply safely isolated from mains power; control hardware, firmware, and/or software for triggering a TES event and controlling the waveform, duration, intensity, and other parameters of stimulation of each electrode; and one or more pairs of electrodes with gel, saline, or another material for electrical coupling to the scalp. The hardware, firmware, and software for TES may include additional or fewer components. Hardware, firmware, and software for TES may include a variety of components.

Embodiments of the TES applicators described herein may be adherent and self-contained transdermal electrical stimulation (TES) systems. In at least some embodiments, an adherent and self-contained TES system is battery powered, communicates wirelessly with a controller unit, and can detach into two independent assemblies, a master assembly and a slave assembly, coupled only by an electrically conductive wire. The master incorporates a microcontroller for managing the current delivery, a battery, a microcontroller, a wireless communication module, other electronic circuitry, and an adherent electrode assembly. The slave assembly contains an adherent electrode assembly, is tethered to the master assembly (only) by a multicore wire, and fits in the case of the master assembly until a subject is ready for a TES session. To begin a TES session a subject separates the slave assembly from the master assembly housing and places both adherent electrodes on his/her head. The electrode assemblies are replaceable and/or disposable.

Figure 7A:
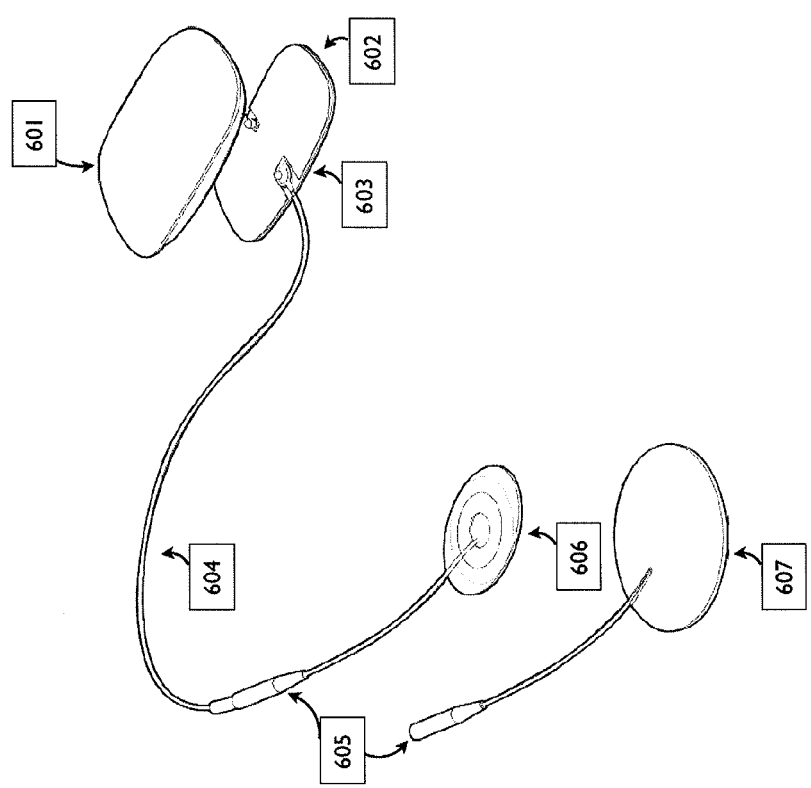
FIG. 7A is one example of a TES applicator in a kit including a reusable transdermal electrical stimulation controller and multiple electrodes that may be connected thereto.

FIG. 7A illustrates one example of a TES applicator as described herein. In FIG. 7A, the TES applicator includes a pair of electrodes, a first electrode 601 that is coupled directly to the body 603 of the TES applicator 602, and a second electrode 606 that is connected 605 by a cable or wire 604 to the body 603 of the applicator. The electrodes may be replaceable/disposable. Different shaped electrodes 607 may be used with the same re-usable TES applicator device. This apparatus is compact (low-profile) and extremely lightweight and may be worn by the subject, e.g., on the subject's head or face.

Figure 7B:
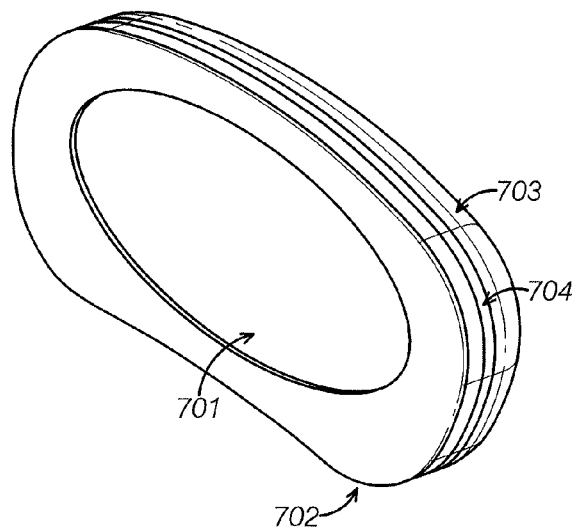
FIG. 7B shows one example of an electrode and housing (body) for a TES applicator.
Figure 7C:
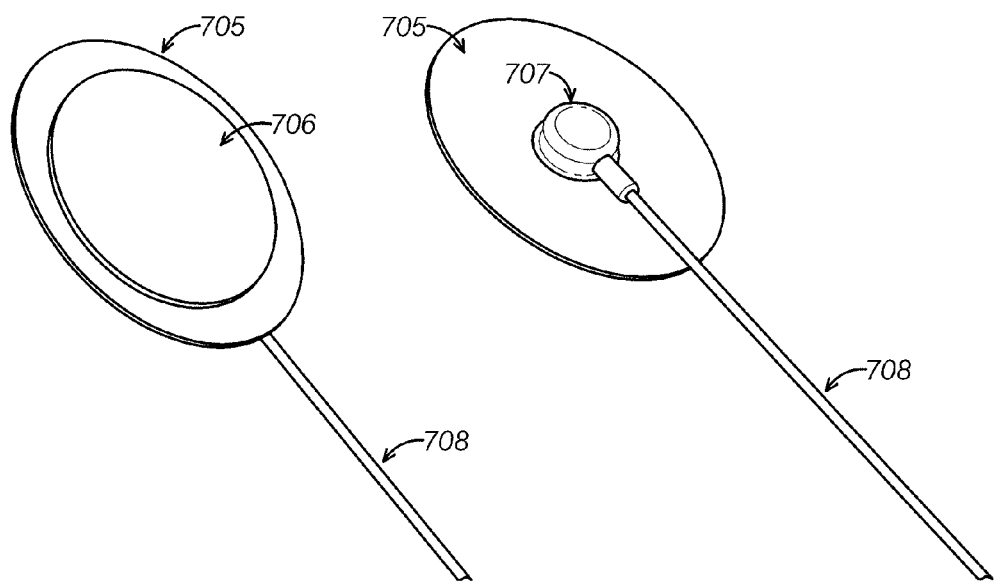
FIG. 7C shows one example of a TES electrode that may be used (e.g., to attach to the neck, behind the ear, etc.) as described herein.

FIG. 7B is another example of an applicator including a first electrode 701 attached to the body 703 of the device including plastic backer 704. The electrode may be removably attached 702 to the body 703. A second electrode (shown in FIG. 7C in front and back views) may also be connected to the body 703 of the device and includes an electrode contact portion 706 and an adhesive portion 705. The second electrode includes a cord or wire 708 electrically connecting it 707 to the body of the device.

Figure 7D:
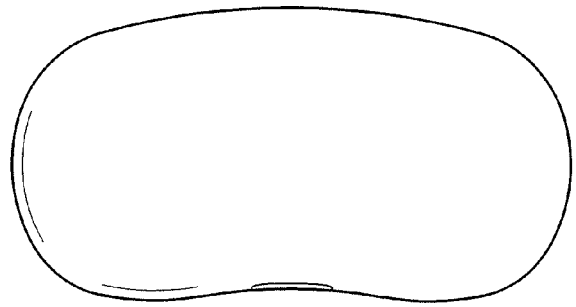
FIG. 7D schematically illustrates one variation of an applicator (showing top, side bottom and front views) of a device (including exemplary dimensions in mm) including a body of a TES applicator that may be wearably attached to the subject.
Figure 7D:
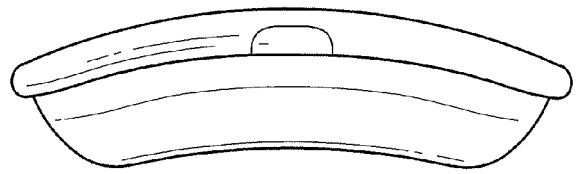
Figure 7D:
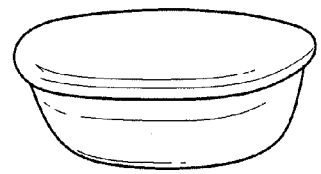
Figure 7D:
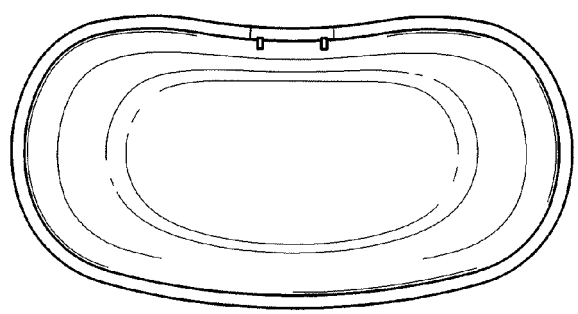

FIG. 7D shows different views (top, bottom, side, and front) of a body portion of another variation of a lightweight, wearable applicator in which an electrode may be attached to the device. In this example, which is particularly useful for connecting to the temple region of the subject, the applicator housing is thin and encloses much of the electronic components of the device.

TES methods and the various configurations described herein may be used with any TES system capable of delivering an appropriate TES waveform transdermally. In general, a TES system may use adherent electrodes and/or electrodes held in place by a wearable apparatus (i.e. cap, headband, necklace, eyeglass frame, or other form factor that enables an electrode to be in physical contact with the subject's skin). In general, the composition of transdermal electrodes of a TES system may have one or more features selected from the group including but not limited to: a hydrogel that contacts the skin, an $Ag/AgCl_2$ component for efficiently transforming an electrical current to an electrochemical one (i.e. carried by charged ions); a layer or other structure for improving the uniformity of current across the face of the electrode; an adhesive (e.g. hydrocolloid) for more securely holding the electrode in consistent contact with the skin; a saline soaked sponge component for delivering current transdermally; or other transdermal electrode technology known to one skilled in the art of transdermal electrical stimulation. In general, the power supply, current controller, and other electronic circuitry (e.g. safety circuitry and, optionally, wireless communication chip sets) of a TES controller may be in a handheld, tabletop, or other portable controller system; wearable components that connect directly to one or both electrodes or connect to the electrodes by wire and are otherwise wearable by a user (or placed within another worn structure (e.g. a headband or armband; a pocket; a necklace, earing, or eyeglass frame)); or completely disposable and integrated with one or more transdermal electrodes of the system.

For example, embodiments of the invention include methods for using electrodes according to configuration A and/or configuration B to induce a cognitive effect as described above by delivering an appropriate TES waveform from a transdermal electrical stimulation system to a subject. Generally, embodiments of the invention also include systems whereby a TES apparatus includes a power supply (e.g. battery), current control and safety circuitry, processor (i.e. microprocessor, microcontroller or the like), electrically conductive connectors and/or cables connecting to the anode(s) and cathode(s), and, optionally, a wireless communication module, in addition to a non-transitory computer-readable storage medium storing a set of instructions capable of being executed by the processor that, when executed by the processor causes a TES waveform to be delivered transdermally between the anode (or set of isoelectric anodes) and cathode (or set of isoelectric cathodes).

Stimulation intensities above 10 mA may be used for inducing a beneficial cognitive effect. However, electrodes for TES need to be small in at least some instances (e.g. to achieve improved localization of an electrode field to a target portion of the nervous system; or because an electrode location is near an area that is covered with hair and thus less than optimal for electrode placement; or because an area of skin sensitivity is nearby, such as the mastoid area behind the ear; or because an area of sensitivity to muscle twitching is nearby, such as the area around the eye). Relative to larger electrodes, embodiments of the TES system that use smaller electrodes have higher impedance due to reduced surface area of contact with the subject. Moreover, electrodes comprised of hydrogels (including adhesive hydrogels) or other compositions for coupling electrically to the body without leaving a significant residue (or wetness, as occurs for saline-soaked sponge electrodes) may be limited in terms of how low electrode impedance can be while maintaining other required properties (e.g. capacity to buffer pH changes from charge imbalanced stimulation).

Despite the known reduction of tissue impedance at increasing frequencies (e.g. from 100 s of Hz to low 10 s of kHz)—and the effect of other waveform features on impedance, the system impedance of a TES apparatus and electrode configuration as described herein for inducing a beneficial cognitive effect is generally between 1 kOhm and 25 kOhm. Impedance values above 10 kOhm are not uncommon. Accordingly, high supply voltages are required to deliver peak currents above 3 mA (or up to and above 15 mA in some instances) according to Ohm's law.

Thus, TES systems described herein incorporate electronic circuitry to achieve high voltage electrical stimulation, where high voltage corresponds to a circuit supply voltage generally greater than 10 V and optionally greater than 15 V, greater than 20 V, greater than 30 V, greater than 40 V, greater than 50 V, greater than 55 V, greater than 60 V, greater than 65 V, or greater than 75 V. An apparatus for delivering high current stimulation comprises a power source (generally a battery) with rapid discharge properties (generally 1 C or higher; preferably 3 C or higher; 5 C or higher; or 10 C or higher) so that peak currents can be delivered; a transformer (buck boost or other) to take lower voltage output of a battery or other power source and provide high voltage levels needed to provide specified power level; and other electronic circuit components designed to operate predictably and reliably at high voltage.

Previous systems for transdermal electrical stimulation targeting the nervous system have generally used direct current stimulation for which currents above 2 mA (and especially for currents above 3 mA) often cause irritation, pain, or tissue damage. Thus, high voltage transdermal electrical stimulation systems for inducing neuromodulation have not previously been considered.

Special care must be taken to ensure that the high voltage TES systems described herein operate safely and do not shock, burn, irritate, or otherwise induce discomfort in or tissue damage to a user. In general, safety elements can be incorporated in electrical circuit and firmware components of a TES system, including but not limited to: maximum instantaneous power output; maximum instantaneous current output; maximum temporal average power output; maximum temporal average current output; maximum controller operating temperature; maximum battery operating temperature; minimum battery supply voltage and/or capacity); and other features to ensure that stimulation delivered meets specifications for safety.

In embodiments of the invention, a wearable assembly constrains the position of electrodes so that when a user wears the assembly, the electrode positions are at or near the locations required for a configuration. Alternatively, the shape or other features (e.g. tactile features) can guide a user to place an electrode in an appropriate location for a particular Configuration. The wearable assembly can take a variety of forms, including, but not limited to, a hat, headband, necklace, around-the-ear form factor, or another wearable system that constrains electrode positions. Optionally, a wearable assembly that constrains electrode positions according to Configuration A or Configuration B also contains a battery or other power source and programmable controller that delivers a TES waveform to electrodes. One of ordinary skill in the art would appreciate there are many usable forms for a wearable assembly, and embodiments of the present invention are contemplated for use with any such wearable assembly.

Generally, the apparatuses described herein may include two electrodes (e.g., cathodes or sets of cathodes) placed at appropriate locations for both Configuration A and Configuration B on a subject and further comprising a switch (electrical, mechanical, optical, or the like) that alternatively connects the single anode (or set of isoeletric anode electrodes) to the cathode for configuration A or configuration B and is further configured to deliver an appropriate TES waveform to induce the cognitive effect associated with the cathode configuration.

Figure 8:
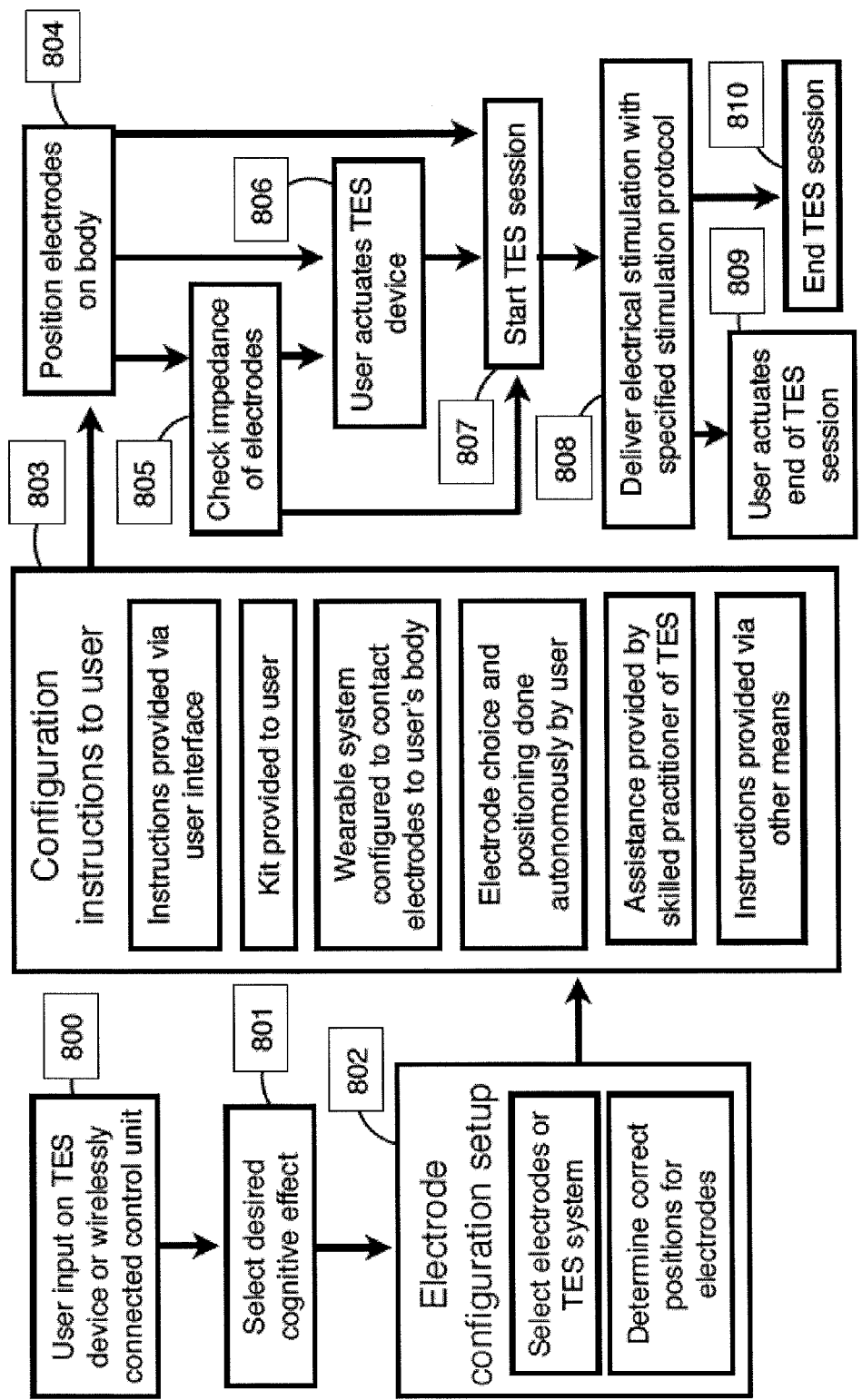
FIG. 8 illustrates one variation of a workflow for configuring, actuating, and ending a TES session.

FIG. 8 illustrates one variation of a schematic diagram showing the composition and use of TES systems. FIG. 8 shows an exemplary workflow for configuring, actuating, and ending a TES session. User input on TES device or wirelessly connected control unit 800 may be used to select desired cognitive effect 801 which determines electrode configuration setup 802 to achieve the desired cognitive effect, including selection of electrodes or a TES system that contains electrodes and determination of correct positions for electrodes. In an embodiment, configuration instructions to user 803 are provided by one or more ways selected from the list including but not limited to: instructions provided via user interface; kit provided to user; wearable system configured to contact TES electrodes to appropriate portions of a user's body; electrode choice and positioning done autonomously by user (e.g. due to previous experience with TES); assistance provided by skilled practitioner of TES; and instructions provided via other means.

Based on these instructions or knowledge, a user or other individual or system positions electrodes on body 804. In some embodiments, the TES session starts 807 automatically after electrodes are positioned on the body. In other embodiments, the impedance of the electrodes 805 is checked by a TES system before the TES session starts 807. In some embodiments, after impedance of the electrodes 805 is checked by a TES system, user actuates TES device 806 before the TES session starts 807. In other embodiments, after positioning electrodes on the body 804 the user actuates the TES device 806 to start the TES session 807. Once the TES session starts, the next step is to deliver electrical stimulation with specified stimulation protocol 808. In some embodiments, a user actuates end of TES session 809. In other embodiments, the TES session ends automatically when the stimulation protocol completes 810.

Figure 9:
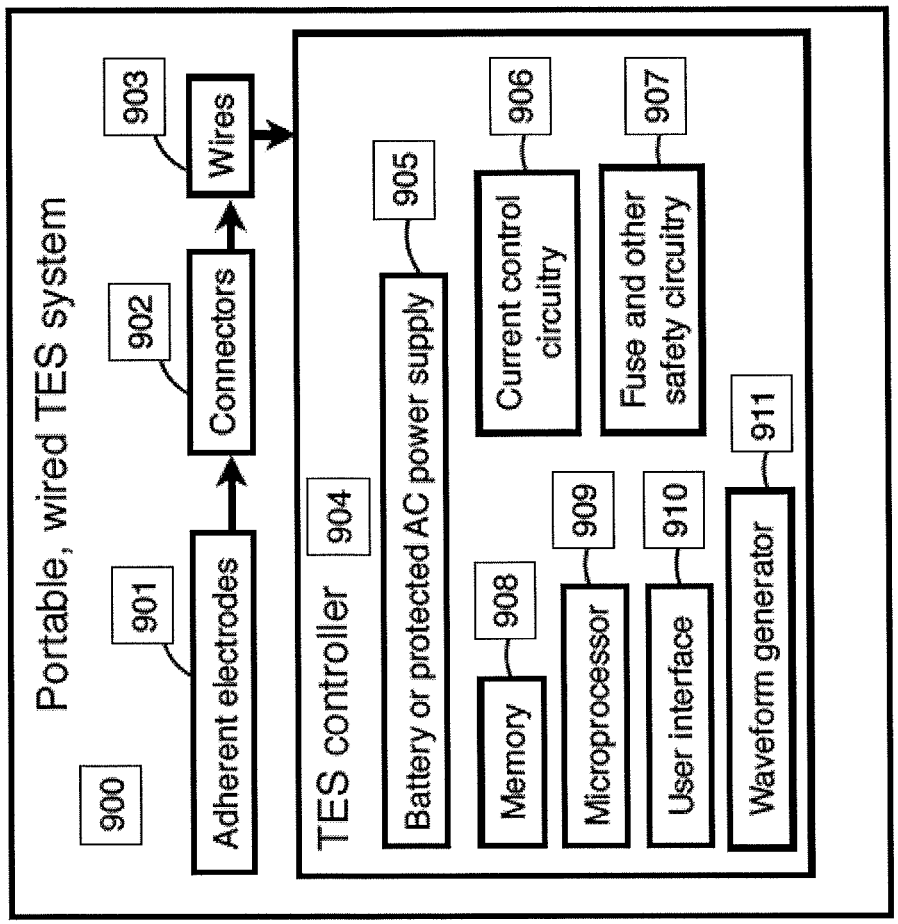
FIG. 9 schematically illustrates components of a portable, wired TES system.

FIG. 9 shows components of portable, wired TES system 900. Adherent electrodes 901 may be connected to TES controller 904 via connectors 902 and wires 903. TES controller 904 has several components including battery or protected AC power supply 905, fuse and other safety circuitry 907, memory 908, microprocessor 909, user interface 910, current control circuitry 906, and waveform generator 911. The neuroConn DC-stimulator (neuroConn GmbH, Ilmenau, Germany) and Activadose II (Activatek Inc. Salt Lake City, Utah) are commercially available portable systems that connect to electrodes by wires that can be used for tDCS. The inTENSity™ product line (Current Solutions LLC, Austin, Tex.) are commercially available portable systems that connect to electrodes by wires and can be configured for constant and interferential tACS. Other commercial or custom systems can be used as a portable, wired TES system to deliver tACS, tDCS, tRNS, or another form of TES.

Figure 10:
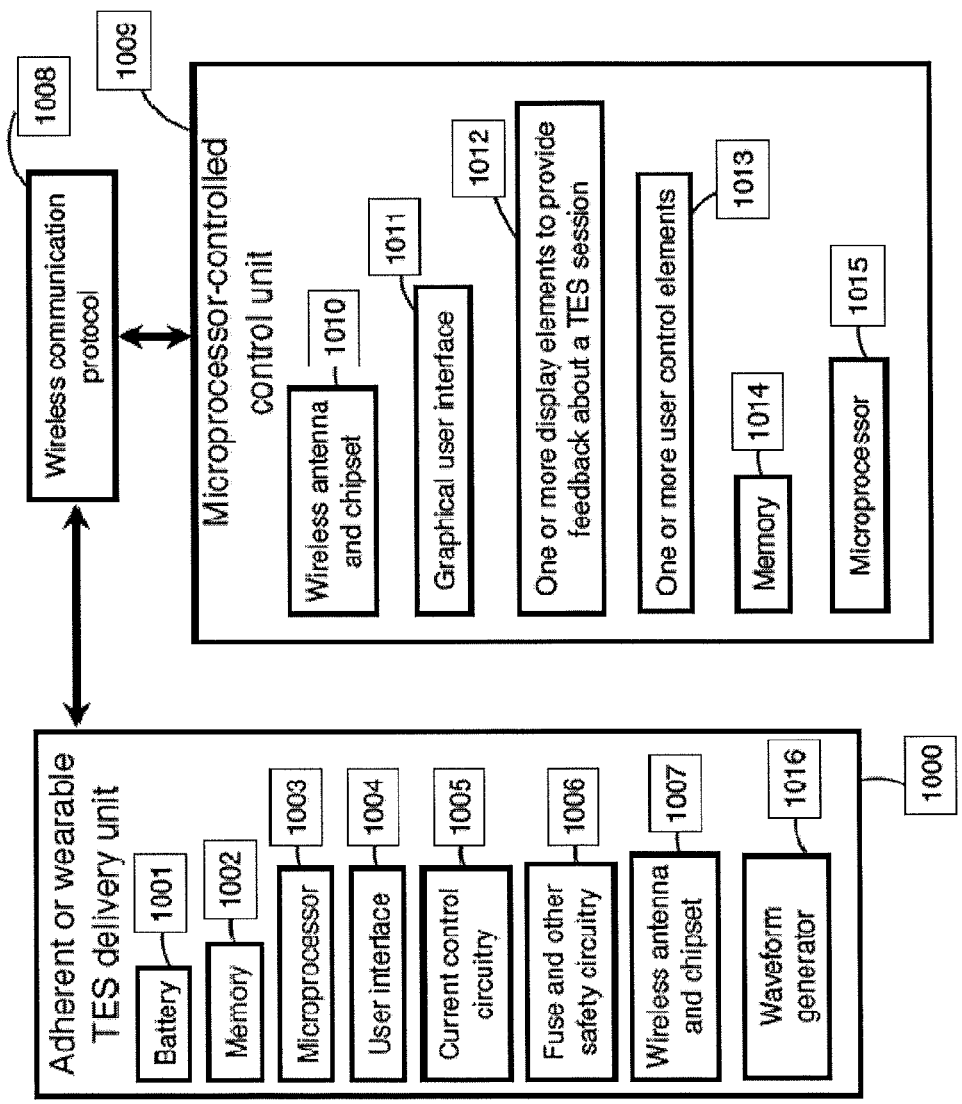
FIG. 10 schematically illustrates components of a TES system that connects wirelessly to a control unit comprising a microprocessor.

FIG. 10 shows a TES system comprising adherent or wearable TES delivery unit 1000 that communicates wirelessly with microprocessor-controlled control unit 1009 (e.g. a smartphone running an Android or iOS operating system such as an iPhone or Samsung Galaxy, a tablet such as an iPad, a personal computer including, but not limited to, laptops and desktop computers, or any other suitable computing device). In this exemplar embodiment, adherent or wearable TES delivery unit 1000 holds two or more electrodes in dermal contact with a subject with one or more of: an adhesive, a shaped form factor that fits on or is worn on a portion of a user's body (e.g. a headband or around-the-ear 'eyeglass' style form factor). In an exemplar embodiment, adherent or wearable TES delivery 1000 comprises components: battery 1001, memory 1002, microprocessor 1003, user interface 1004, current control circuitry 1005, fuse and other safety circuitry 1006, wireless antenna and chipset 1007, and waveform generator 1016. Microprocessor-controlled control unit 1009 includes components: wireless antenna and chipset 1015, graphical user interface 1011, one or more display elements to provide feedback about a TES session 1012, one or more user control elements 1013, memory 1014, and microprocessor 1015. In an alternate embodiment the TES delivery unit 1000 may include additional or fewer components. One of ordinary skill in the art would appreciate that a TES delivery unit could be comprised of a variety of components, and embodiments of the present invention are contemplated for use any such component.

Adherent or wearable TES delivery 1000 may be configured to communicate bidirectionally with wireless communication protocol 1008 to microprocessor-controlled system 1009. The system can be configured to communicate various forms of data wirelessly, including, but not limited to, trigger signals, control signals, safety alert signals, stimulation timing, stimulation duration, stimulation intensity, other aspects of stimulation protocol, electrode quality, electrode impedance, and battery levels. Communication may be made with devices and controllers using methods known in the art, including but not limited to, RF, WIFI, WiMax, Bluetooth, BLE, UHF, NHF, GSM, CDMA, LAN, WAN, or another wireless protocol. Pulsed infrared light as transmitted for instance by a remote control is an additional wireless form of communication. Near Field Communication (NFC) is another useful technique for communicating with a neuromodulation system or neuromodulation puck. One of ordinary skill in the art would appreciate that there are numerous wireless communication protocols that could be utilized with embodiments of the present invention, and embodiments of the present invention are contemplated for use with any wireless communication protocol.

Adherent or wearable TES delivery unit 1009 may not include user interface 1004 and is controlled exclusively through wireless communication protocol 1008 to control unit 1009. In an alternate embodiment, adherent or wearable TES delivery unit 1009 does not include wireless antenna and chipset 1007 and is controlled exclusively through user interface 1004. One skilled in the art will recognize that alternative TES systems can be designed with multiple configurations while still being capable of delivering electrical stimulation transcranially and transdermally into a subject.

Figure 21A:
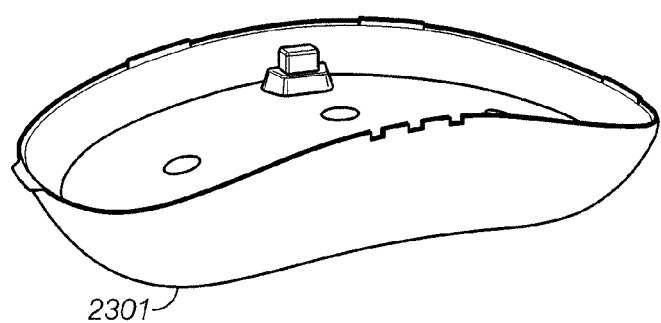
FIG. 21A shows one variation of TES applicator.
Figure 22:
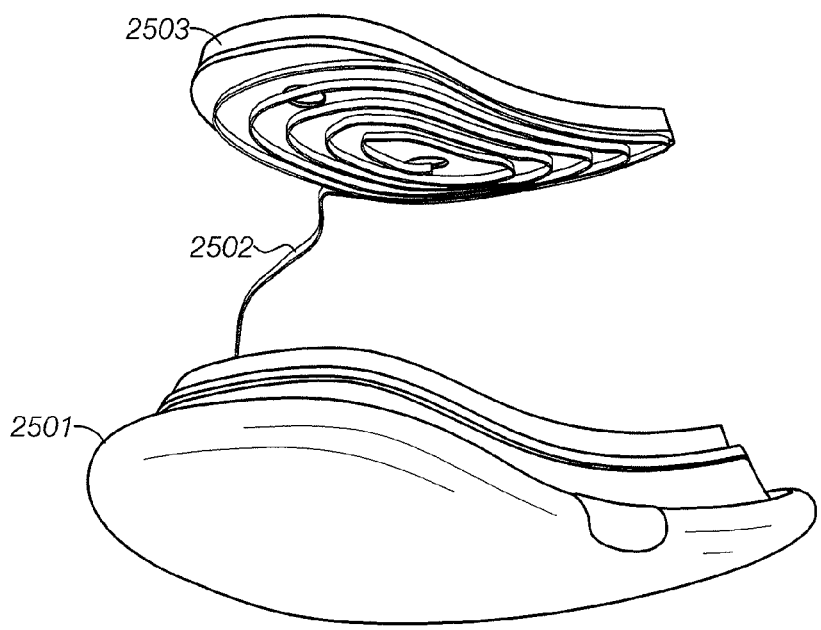
FIG. 22 is a perspective view of the applicator of FIGS. 21A-21B.
Figure 21B:
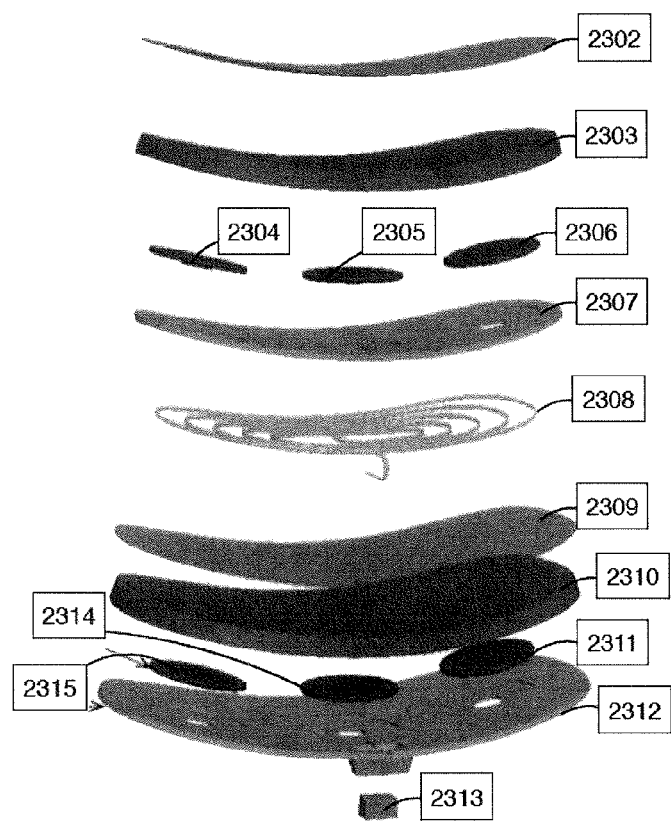
FIG. 21B shows the applicator of FIG. 21A in an exploded view.
Figure 23:
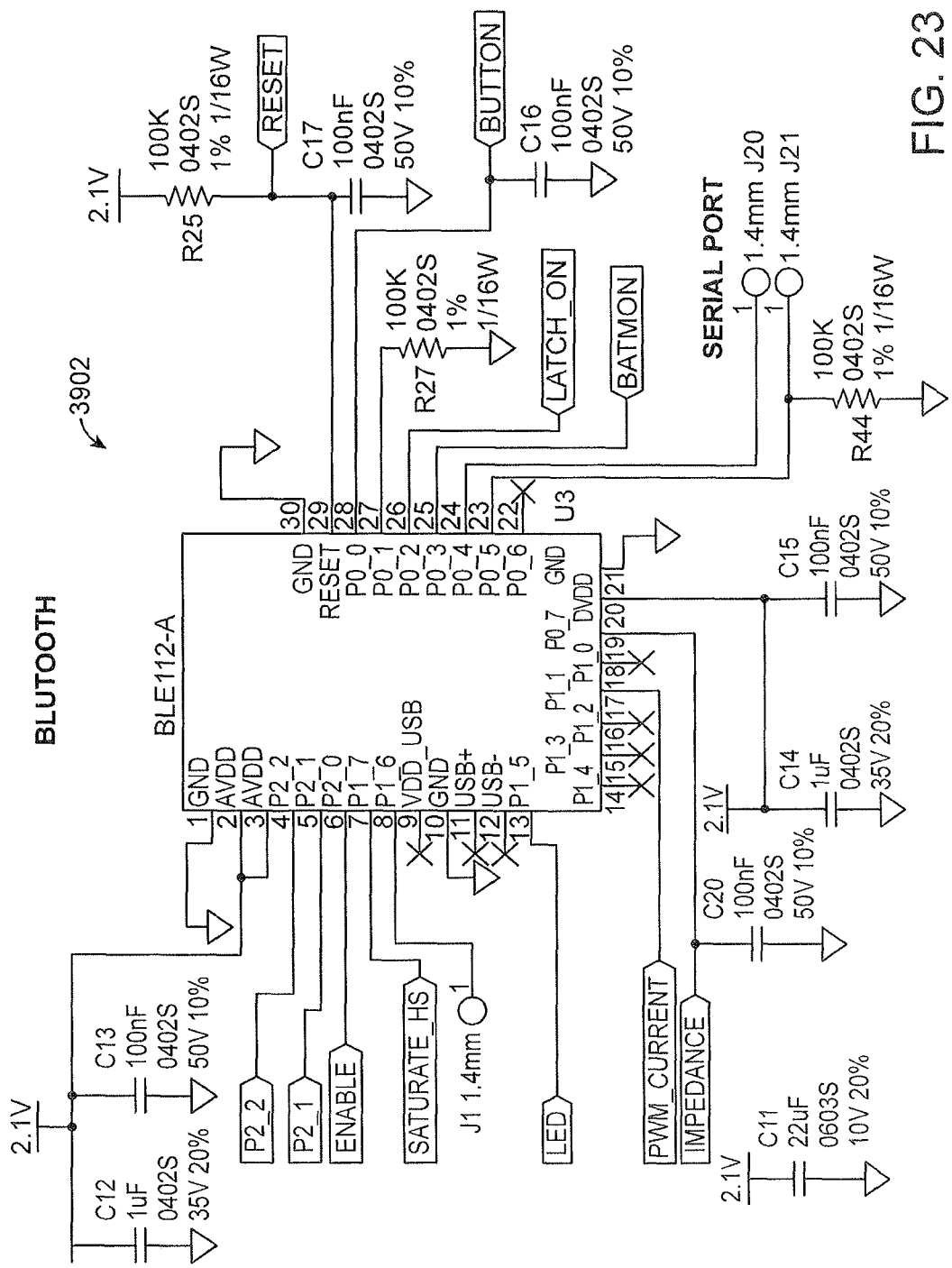
FIG. 23 is a schematic illustrating one variation of a wireless communications module (e.g., Bluetooth module) that may be used as part of a TES applicator.
Figure 24:
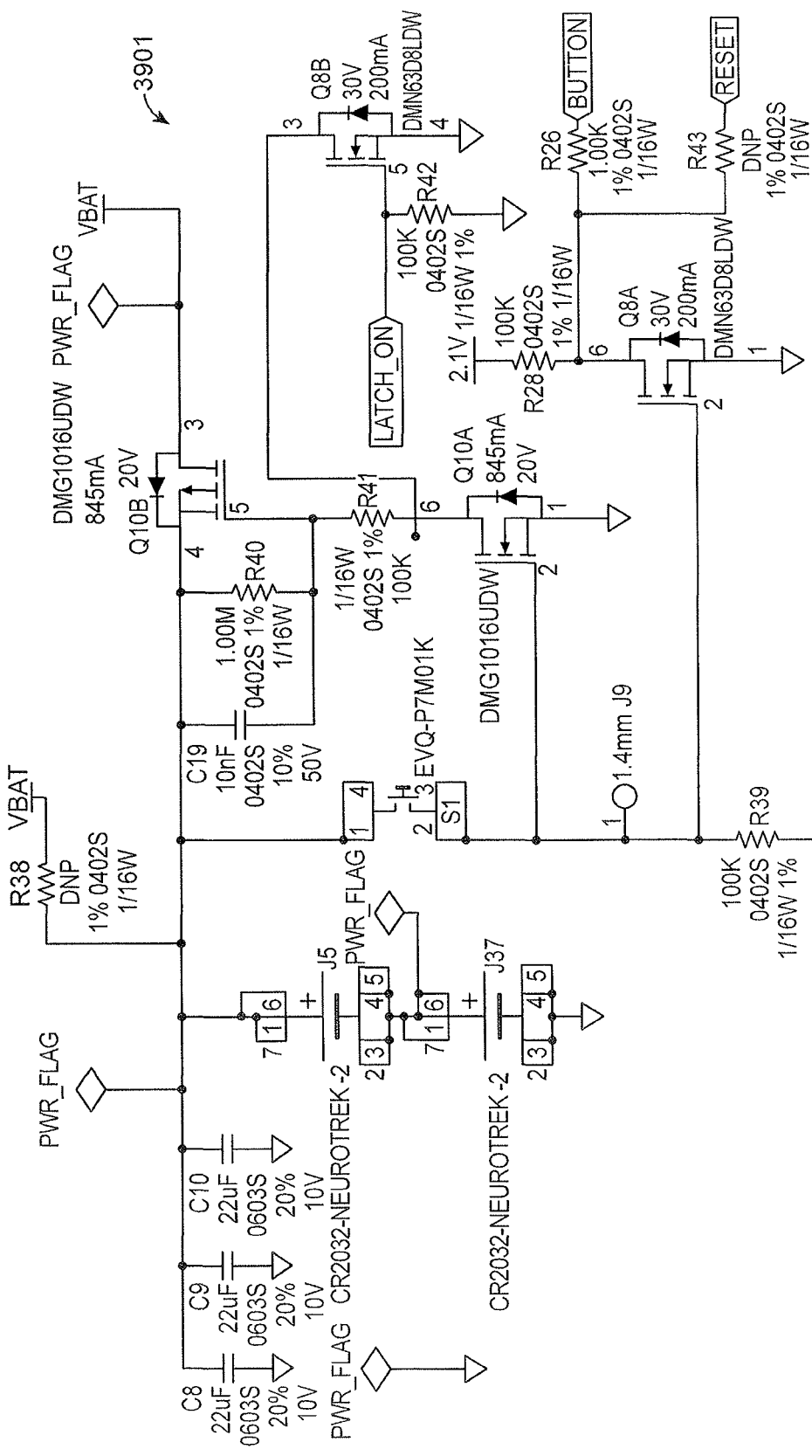
FIG. 24 is a schematic illustrating one variation of a smart power switch that may be used as part of a TES applicator.
Figure 25:
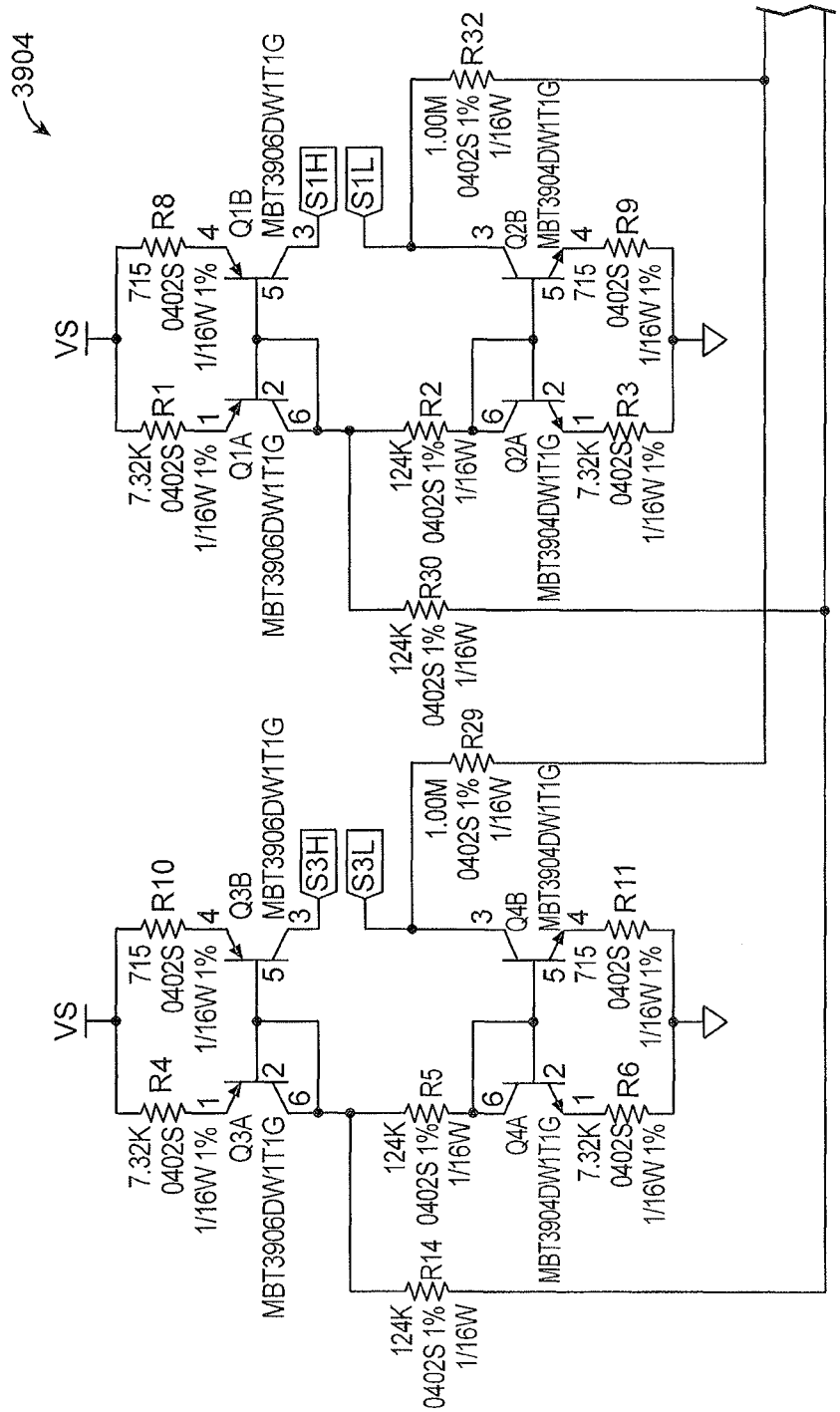
FIG. 25 is a schematic of current sources that may be part of a TES applicator as described herein.
Figure 25:
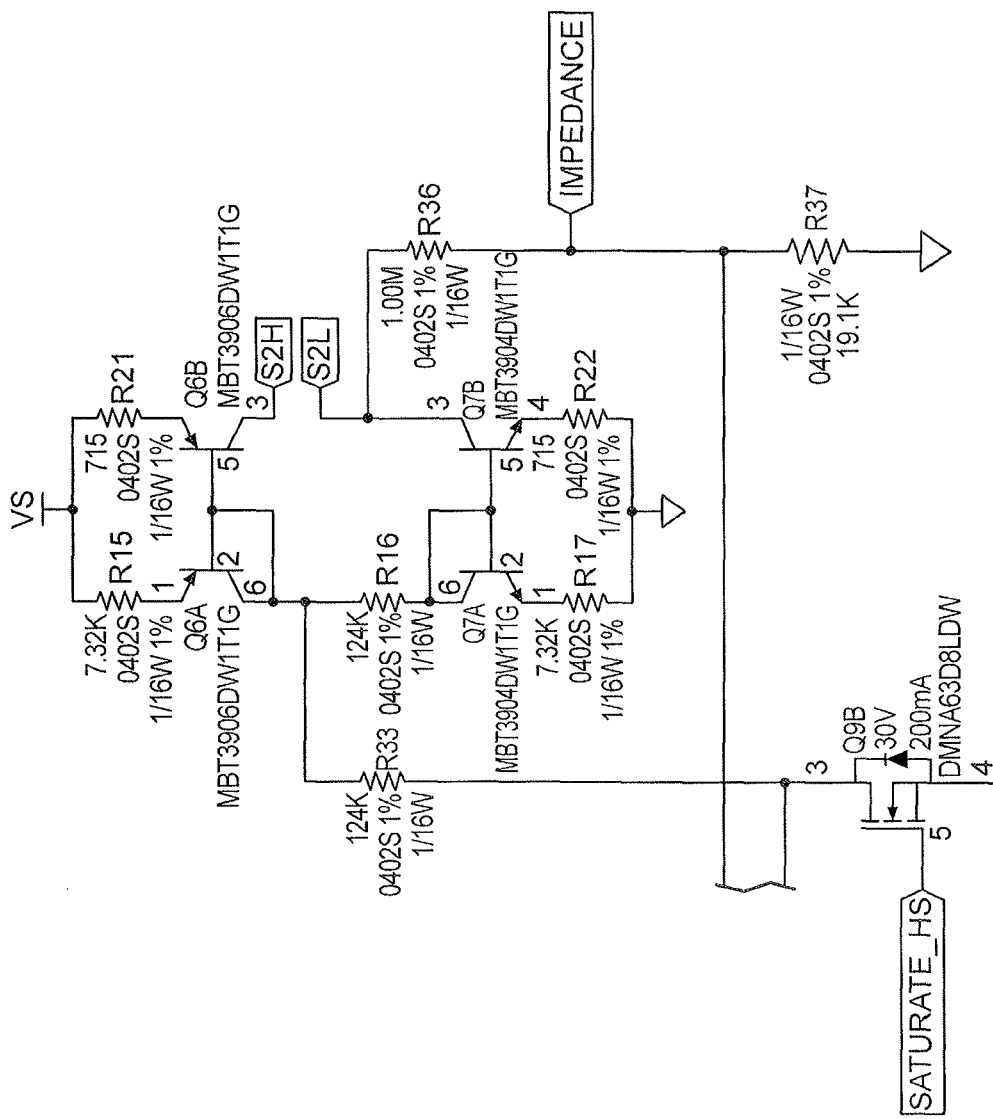
Figure 26:
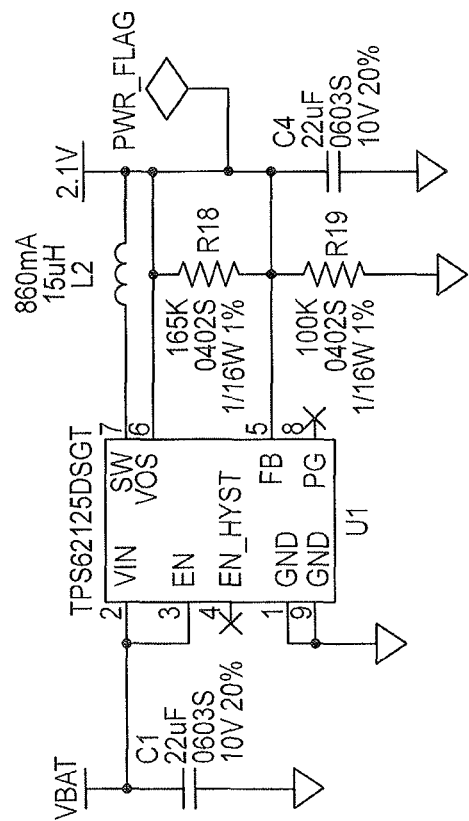
FIG. 26 is a schematic of a buck converter for a TES applicator.

FIGS. 21A to 27 illustrate one variation of a TES applicator apparatus as described herein. In this example, the TES applicator is configured as an adherent and self-contained TES system that is battery powered, communicates wirelessly with a remote controller unit and includes a master assembly (body with control module therein and an attached electrode) and a slave assembly (second electrode), coupled only by an electrically conductive wire. The master incorporates a microcontroller (control module) for managing the current delivery, a battery, a wireless communication module, other electronic circuitry, and an adherent electrode assembly. The slave assembly contains an adherent electrode assembly, is tethered to the master assembly (only) by a multicore wire, and fits in the case of the master assembly until a subject is ready for a TES session. To begin a TES session a subject may (in some variations) separate the slave assembly from the master assembly housing and places both adherent electrodes on his/her body in the appropriate locations, consistent with the instructions for a particular configuration as described herein. The electrode assemblies may be replaceable and/or disposable. For example, FIGS. 21A and 21B show renderings of one variation of a TES system 2301 (FIG. 21A) and 'exploded' view of the TES system (FIG. 21B). The system includes components of an electrode assembly of a slave assembly: peel and stick adhesive film 2302; electrically conductive adhesive electrode 2303; Ag/AgCl current spreaders (and pH buffering units) 2304, 2305, 2306; and tethered electrode base (e.g. made of molded styrene or pressure formed PET) 2307. The slave assembly is connected to the master assembly by flexible conductive wire 2308. The master assembly also has an electrode assembly comprising: peel and stick adhesive film 2309; electrically conductive adhesive electrode 2310; Ag/AgCl current spreaders (and pH buffering units) 2311, 2314, 2315; tethered electrode base (e.g. made of molded styrene or pressure formed PET) 2312; and connector 2313 for attaching to and delivering current from a control module of the master assembly. FIG. 22 shows a view of a TES applicator ("puck") with slave electrode 2503 assembly separate from master assembly 2501 and tethered by wire 2502 connecting the two.

The body of the TES applicator may be made of any appropriate material, for example, pressure formed PET or injection molded styrene, and may be a reusable control module enclosure ('keeper') of master assembly that contains: power, wireless communication, programmable processor, and other electrical components.

Figure 27:
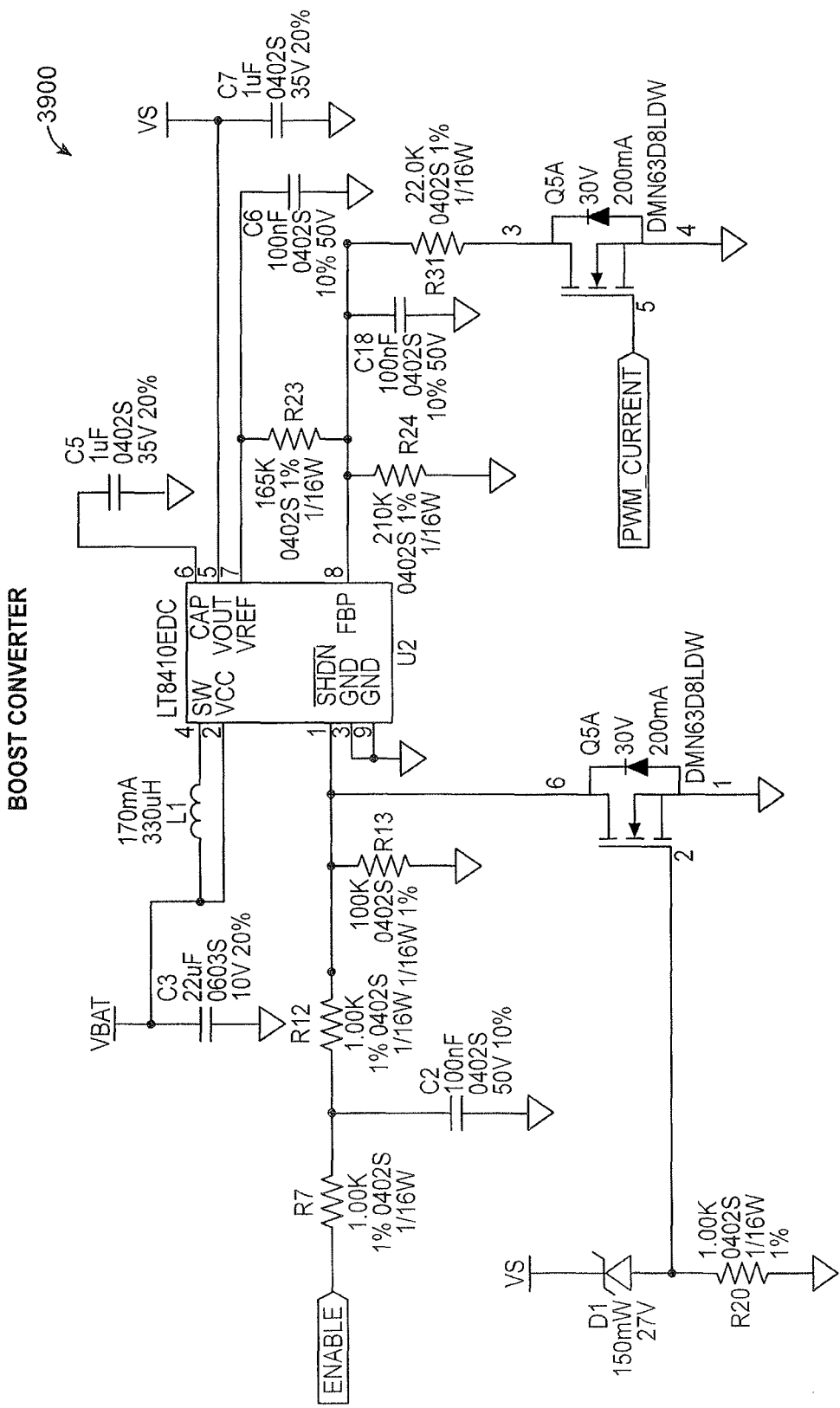
FIG. 27 is a schematic of a burst converter for a TES applicator as described herein.

Circuit diagrams of certain components for a TES system are shown in FIGS. 23 to 27 including the wireless Bluetooth module 3902 (FIG. 23), smart power switch 3901 (FIG. 24), current sources 3904 (FIG. 25), buck convertor 3903 (FIG. 26) and burst converter 3900 (FIG. 27). Circuitry for LED, battery voltage monitoring, programming interface, power supply access, current sources connector and the like are not shown.

An advantageous feature of a TES applicator having a master assembly and a slave assembly may be that the TES system can be detached and connected only by a flexible, electrically conductive tethering wire. In some embodiments, the electrically conductive tethering wire can be a ribbon cable or a multi-core wire. The electrode assemblies on both the master and slave units are thus electrically coupled to the reusable control module of the master assembly. The electrically conductive tethering wire may be part of the disposable electrode assembly. A subject (user) may unfurl the electrically conductive tethering wire as needed so that the master and slave electrode assemblies can be adhered to appropriate parts of the head to deliver TES neuromodulation to a brain region of interest. This embodiment is advantageous because the relative position of the two assemblies is only constrained by the length of an electrically conductive flexible wire connecting the two assemblies. This embodiment provides flexibility for electrode positioning, because the electrode assemblies are adherent, small, and not part of a larger assembly that constrains the relative position where a plurality of electrodes is in contact with the head or body.

A small battery or supercapacitor may be sufficient to supply the power for a TES session. The primary power drain for a TES system is the current delivered to the body of a subject. Even a relatively high tDCS current of 6 mA delivered for 30 minutes only requires 3 mA-hours (mAh), easily attainable from a portable battery (e.g. a commercially available rechargeable 3.7V 150 mAh lithium ion polymer battery weighs less than 5 grams). Pulsed stimulation protocols are even more efficient in terms of power requirements. Embodiments that incorporate one or more capacitors and/or supercapacitors are useful for shorter or lower current TES sessions (e.g. a 3.6F supercapacitor provides 1 mAh, sufficient for 6 mA direct current to be delivered for 5 minutes and even longer pulsed stimulation sessions). Additional power may be required for other electrical components of a battery-powered TES system, informing battery and capacitor choices for a given TES duration and protocol.

An audio port or charging connector for a smartphone or tablet may be used to supply power and/or control signals to a TES system. In advantageous embodiments, the audio port or charging connector for a smartphone or tablet is used to charge a battery or capacitor of a TES system so that electrical stimulation can be delivered at a later time when the smartphone or tablet is no longer connected to the TES system. In some embodiments, power is supplied to a TES system by a manually-operated crank charging system or one or more solar cells.

The systems and methods described herein may permit users to 'bookmark' a transdermal electrical stimulation waveform to provide commentary, tagging, feedback, and/or social sharing. The experience of receiving transdermal electrical stimulation extends in time and waveforms may be designed so that the experience changes over the course of seconds to minutes. For instance, a phosphene may be delivered at a particular time point; or a parameter of stimulation may be changed (e.g. a peak intensity, stimulation frequency, pulse width, or other parameter may be ramped over a period of time) that induces a variation in the neuromodulation delivered to the subject and thus may modify in quality or intensity a cognitive effect induced in the subject. A user interface may permit a subject to associate a point in time during a waveform with a comment, rating, tag, highlight, or other information that communicates something about the experience of that transdermal electrical stimulation by the user.

Also described herein are non-transitory computer-readable storage medium storing a set of instructions capable of being executed by a remote processor (and particularly a smartphone or the like), when executed by the computing device containing the remote processor causes a user interface to be presented that enables a user to generate a comment, rating, tag, highlight, or other information that communicates something about the experience of that transdermal electrical stimulation by the user and automatically associates that information with a transdermal electrical stimulation waveform. In one embodiment, a database entry is made for the comment that includes a ranking and a tag, as well as a unique ID for the user, the waveform, and the time during the waveform at which the comment is made. For instance, a user interface may include a data entry field (e.g. text field that incorporates 'auto-complete' functionality based on previously entered tags), button, pull-down menu, or ranking system (select 1 or more stars) on a touchscreen display such that a user can generate a comment about stimulation that is automatically associated with the waveform and time during the waveform.

One beneficial feature of this embodiment is that comments, tags, rankings, etc. can be compiled across users (all users; sets of users defined demographically, psychographically, socially (e.g. composed of friends on Facebook), or otherwise) and across sessions so that a particular user can compare experiences between sessions using the same transdermal electrical stimulation waveform. In an embodiment, a non-transitory computer-readable storage medium storing a set of instructions capable of being executed by a remote processor (and particularly a smartphone or the like), when executed by the computing device containing the remote processor causes a display on the computing device (or communicably connected to the computing device, i.e. via screen sharing or Apple TV) to show a user commentary across users and/or sessions for a selected waveform, including commentary associated with portions of the waveform that the user has not yet experienced during a TES session. Thus, a user will form an expectation of highly salient or otherwise interesting (or uninteresting) portions of a waveform (i.e. 'watch out for phosphenes' or 'turn up the intensity here'). The display of commentary and feedback can be quantitative (e.g. a heat map showing the average ranking across sections of the waveform as a function of time or the density of feedback during a particular portion of a TES waveform). Different metadata may be displayed automatically depending on the amount of feedback available and/or the temporal scale of the waveform being displayed.

Similarly, metadata from sensors worn by or otherwise interrogating a TES user such as physiological sensors (e.g. measuring galvanic skin response, temperature, heart rate, heart rate variability, breathing rate, pupil dilation, movements, cortisol levels, amylase levels) can be aligned temporally with a waveform.

Any of the systems and methods for adapting a TES waveform described herein may account for impedance and/or capacitance during use.

In general, TES waveforms may account for expected changes in electrode and/or skin impedance during a session (or across sessions). Degrading electrodes generally exhibit increased impedance and may deliver current non-uniformly across the electrode-dermal surface (thereby causing increased skin discomfort at current intensity boundaries). In contrast, during a TES session extending minutes, tissue (skin) impedance generally decreases. Impedance of tissue (skin) is known to be frequency-dependent. Generally, higher frequencies of alternating or pulsed stimulation exhibit lower impedance relative to lower frequencies. Frequency dependence of a user's tissue can be estimated or tested empirically.

In general, TES waveforms for configurations described herein may compensate for changing electrical properties of electrode(s) and tissue by altering the frequency, intensity, duty cycle, waveform shape, or other waveform parameter.

Impedance checks or estimates (e.g. from historical data from the user or other users) can be used ahead of time to select a waveform or electrode configuration (e.g. including composition, size, and/or positioning) so that effective and comfortable transdermal electrical stimulation can be delivered for neuromodulation that induces a desired cognitive effect.

In an embodiment, the electrical properties of a user (e.g. frequency-dependent skin impedance) can be used to automatically change the properties of a TES waveform. Both initial (pre-stimulation) and stimulation-induced changes in electrical properties of a user's tissue can help guide waveform selection and/or adjustment for comfort and efficacy.

The system can measure impedance and/or capacitance data from a user once or repeatedly. Repeated measurements can occur at regular intervals, in response to a selection by a user or third party via a user interface on a wearable TES system or controller communicably connected to a wearable TES system (e.g. a smartphone or tablet wirelessly communicating with a TES system). Measured impedance and/or capacitance data is beneficially stored to improve future device function. Impedance and/or capacitance data stored locally on a machine-readable computer memory component of a wearable TES may be beneficial as diagnostic information for improving the function of that unit. Measured impedance and/or capacitance data may also be transferred from a wearable TES system via wired or wireless communication protocols for storage on a machine-readable computer memory component of a computer, smartphone, tablet, dedicated computing unit, or other computerized system. Impedance and/or capacitance data transmitted in real-time or asynchronously via the Internet to a remote server is advantageous because it permits automated storage and integration of data from many users and TES systems for improved device comfort and function.

Beneficial embodiments of TES systems comprise electrical circuitry for measuring impedance and/or capacitance that transmit these data to a machine-readable hardware external to the wearable TES system (including remote servers connected via the Internet) associate metadata with the measurements, including the user, and hardware component versions (e.g. electrodes). Metadata may also include geographical data (i.e. collected from a GPS system contained within the TES system or a separate hardware controller of the TES system such as a smartphone or tablet computer). Geographical data can be used to associate impedance and/or capacitance values with temperature, humidity, and other ambient factors that can affect the electrical properties of electrodes and/or human tissue.

Examples of TES applicators and systems operating as described herein to modify a subject's cognitive state are provided in FIGS. 11-15B.

Figure 11:
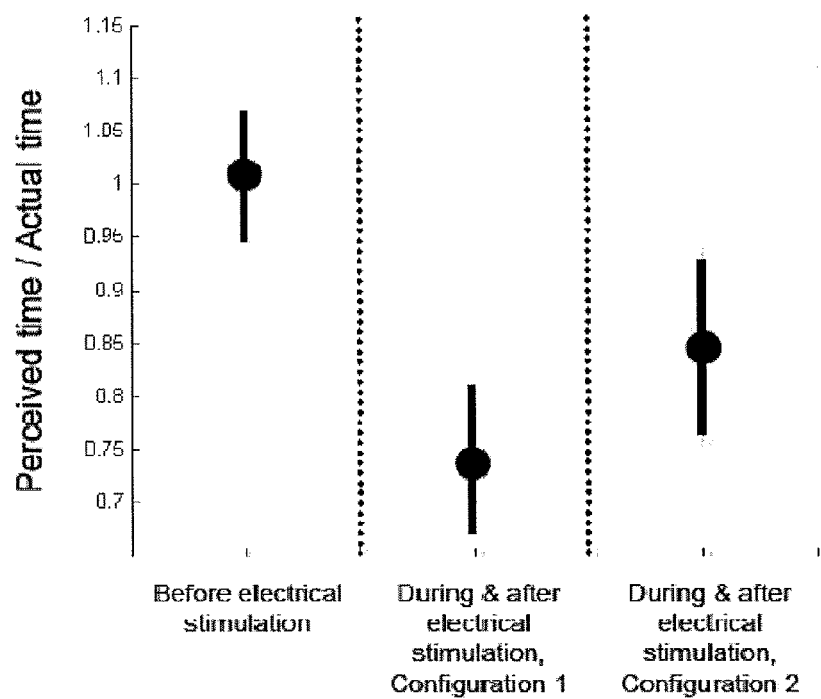
FIG. 11 illustrates the changes in perceived passage of time during and after a TES stimulation session using configuration 1 as described herein.

For example, FIG. 11 illustrates the ratio of perceived time divided by actual time averaged across subjects receiving TES stimulation as described herein. Before electrical stimulation (left data point in FIG. 11), the ratio is about 1, consistent with subjects accurately estimating the passage of time. During stimulation, subjects received transcranial direct current stimulation at a maximum current intensity of 1.0 mA delivered through electrodes positioned according to configuration 1 with the lateral electrode placed on the subject's right side. A rectangular 1.3"×2.1" PALS® Platinum electrode (Axelgaard Manufacturing Co., LTD, part number 891200) served as the anode (106) and a square 2"×2" electrode (Axelgaard Manufacturing Co., LTD, part number UF2020) served as the cathode (105). As a result, during and after stimulation, subjects estimated that time passed slowly: the average time estimate from subjects was about 75% of the actual amount of time that had passed (center data point in FIG. 11). Similarly, subjects receiving stimulation using configuration 2 (TES at 1.5 mA delivered through electrodes positioned according to configuration 2 with both electrodes placed on the subject's right side; a rectangular 1.3"×2.1" PALS® Platinum electrode (Axelgaard Manufacturing Co., LTD, part number 891200) served as the anode and a round (about 1" diameter) Little PALS® ECG electrode (Axelgaard Manufacturing Co., LTD, part number SEN5001) served as the cathode), gave an average estimate of time passage during and after stimulation that was about 85% of the actual amount of time that had passed (right data point in FIG. 11). These results show that TES stimulation for configurations 1 and 2 induces a subjective perception of time passing quickly, a perceptual quality corresponding to cognitive states of focus, attention, and flow.

Figure 12:
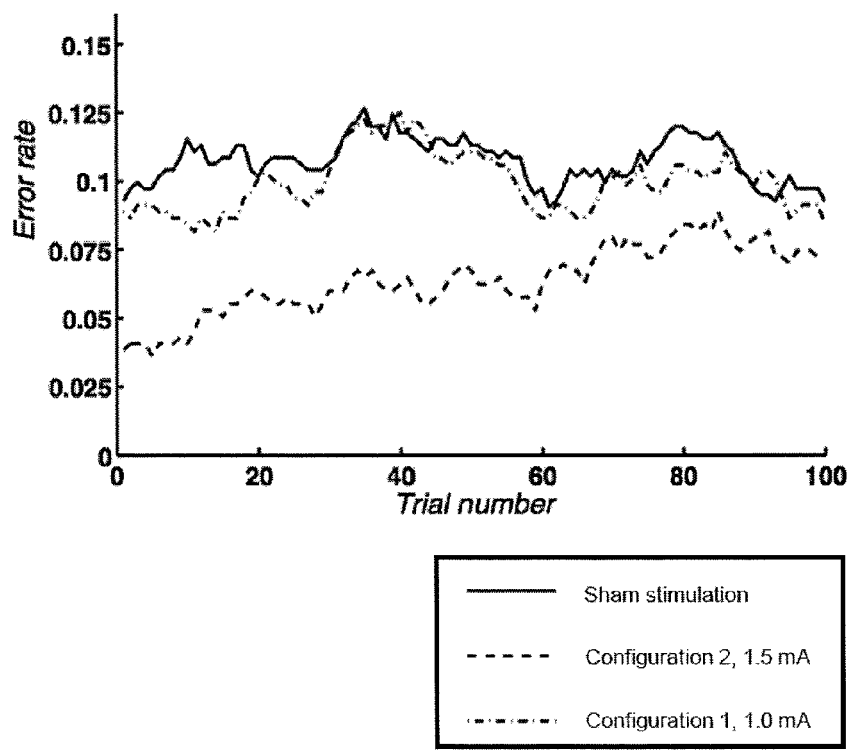
FIG. 12 shows data from subjects performing the 'n-back' task during TES (e.g., tDCS) and sham stimulation.

As shown in FIG. 12, direct current TES using configuration 2 at 1.5 mA also resulted in a significant improvement in performance on a working memory task. In separate sessions on three different days, subjects performed the 'n-back' (where n=2) task while receiving TES or sham stimulation. The n-back task probes working memory, an executive function system closely linked to intellectual function, attention, literacy, and educational success. Working memory is not easily improved with training, suggesting that TES systems and methods for improving working memory could lead to improved intellectual abilities in subjects. In repeated trials, more robust effects were found across subject's using a higher (e.g., 3 mA) intensity.

Figure 13:
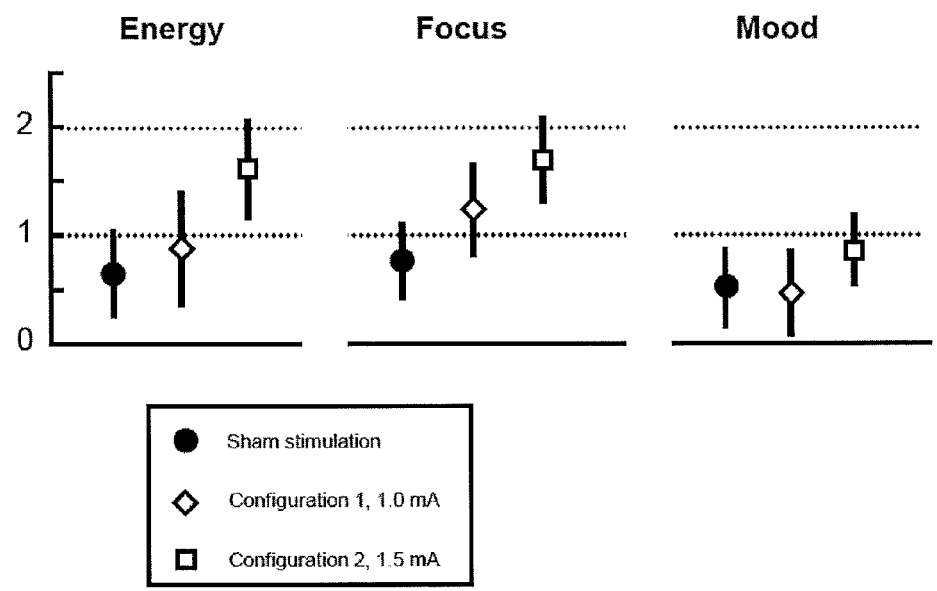
FIG. 13 illustrates subjects' self-reported energy, focus, and mood during TES (e.g., tDCS) and sham stimulation.

FIG. 13 shows average error rates across subjects as a function of trial number in a 100-trial n-back session. Subjects receiving TES using configuration 1 performed at the same baseline level of about 10% error rate as subjects receiving sham "S1" stimulation. In contrast, subjects receiving stimulation using configuration 2 TES had significantly fewer errors, particularly for the first about 50 trials of the n-back session. These results show that a direct current TES stimulation using >1.5 (and more robustly, greater than 3 mA) intensity significantly improves performance on the n-back task, consistent with an enhancement in working memory during stimulation. In contrast, a lower (1 mA) intensity session had no effect on n-back performance relative to sham "S1" stimulation.

This was also seen, for example, when configuration 3 (at an intensity of between 3 and 3.5 mA) was used. In this example, TES increased energy, focus, and mood. Higher energy levels, increased focus, and improved mood are highly desirable changes in cognitive state for enhanced productivity, activity, and happiness. In separate sessions on three different days, subjects completed a survey that assessed subjective perceptions of energy, focus, and mood after receiving TES (configuration 1) stimulation, TES (configuration 2) stimulation, TES (configuration 3) stimulation, sham "S1" stimulation, or sham "S2" stimulation.

Figure 14:
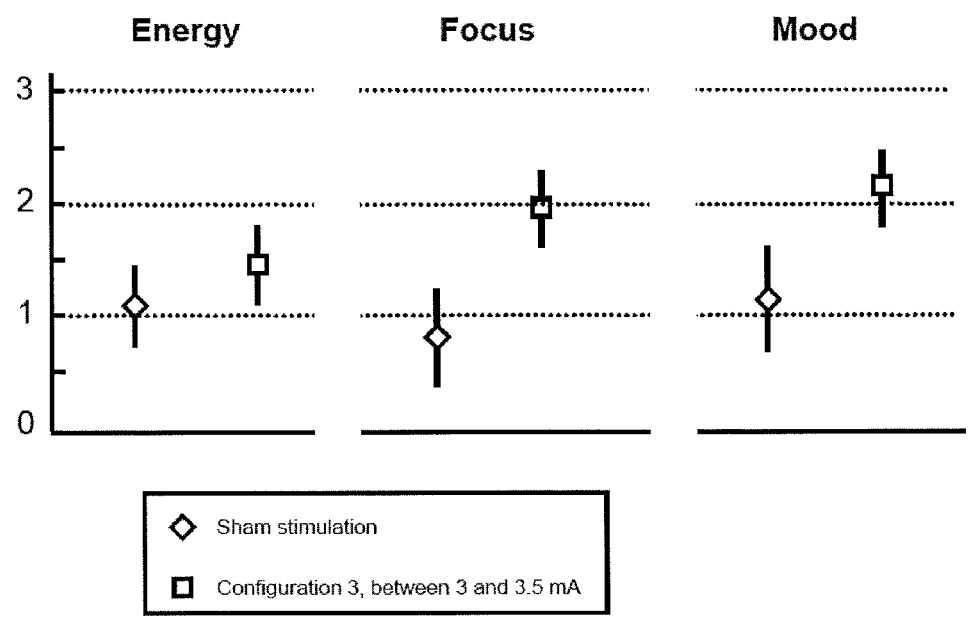
FIG. 14 illustrates subjects' self-reported energy, focus, and mood during TES (e.g., tDCS) and sham stimulation.

FIGS. 12 and 13 show average (+/−SEM) survey results for energy, focus, and mood, normalized to a pre-stimulation baseline survey where higher scores correspond to higher levels of energy, improved focus, and a better mood. Note that sham stimulation survey results greater than 0 likely correspond to a placebo effect. Relative to sham "S1" stimulation, configuration 1 TES induced a moderate improvement in focus, but did not significantly affect energy or mood (FIG. 12). Relative to sham "S1" stimulation, configuration 2 TES induced a substantial improvement in energy and focus in subjects, but did not significantly affect mood (FIG. 12). Relative to sham "S2" stimulation, configuration 3 TES led to subjective reports of improved focus and mood, but did not significantly affect subjective reports about energy levels (FIG. 14). These results show that: a configuration 1 session improves subjects' focus by a small amount, but does not affect their focus or mood; a TES configuration 2 session improves subjects' energy and focus, but does not affect their mood; and a TES configuration 3 session improves subjects' focus and mood, but does not affect their energy. Increasing the intensity, and controlling the frequency (and DC offset and duty cycle as described above) provided substantially more robust effects.

Figures 15A, 15B:
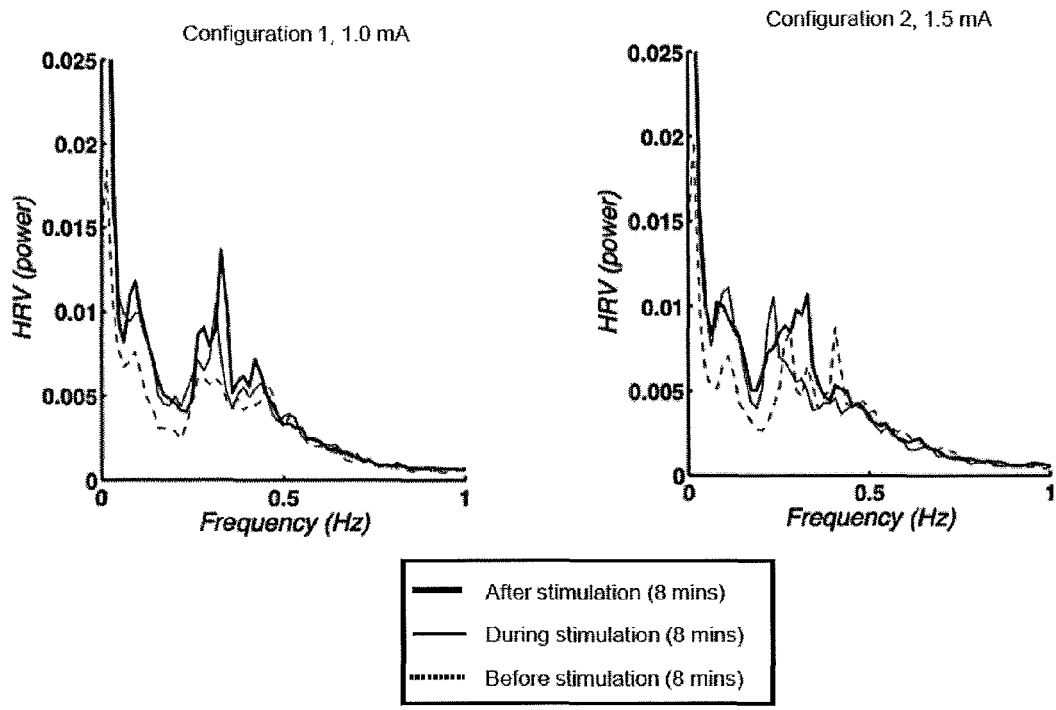
FIGS. 15A and 15B are Fourier transform plots of heart rate variability data collected before, during, and after TES (tDCS) stimulation as described herein for configuration 1 and 2 respectively.

FIGS. 15A and 15B examine the effect of TES on heart rate variability. Heart rate variability (HRV) measures the variability of inter-heartbeat intervals and is considered to be a sensitive assay of autonomic nervous system function. In separate sessions on two different days, subjects wore a pulse sensor system before, during, and after a configuration 1 or configuration 2 TES session. FIGS. 15A and 15B show an average Fourier transform of HRV across subjects receiving a configuration 1 (FIG. 15A) or configuration 2 (FIG. 15B) TES session. Either form of TES stimulation induced increased HRV that was not frequency specific. These results show that a configuration 1 or configuration 2 TES session induces increased heart rate variability and suggests that these forms of transcranial electrical stimulation are effective for controlling the autonomic nervous system and thus a wide range of physiological functions within and outside of the brain.

Figure 16:
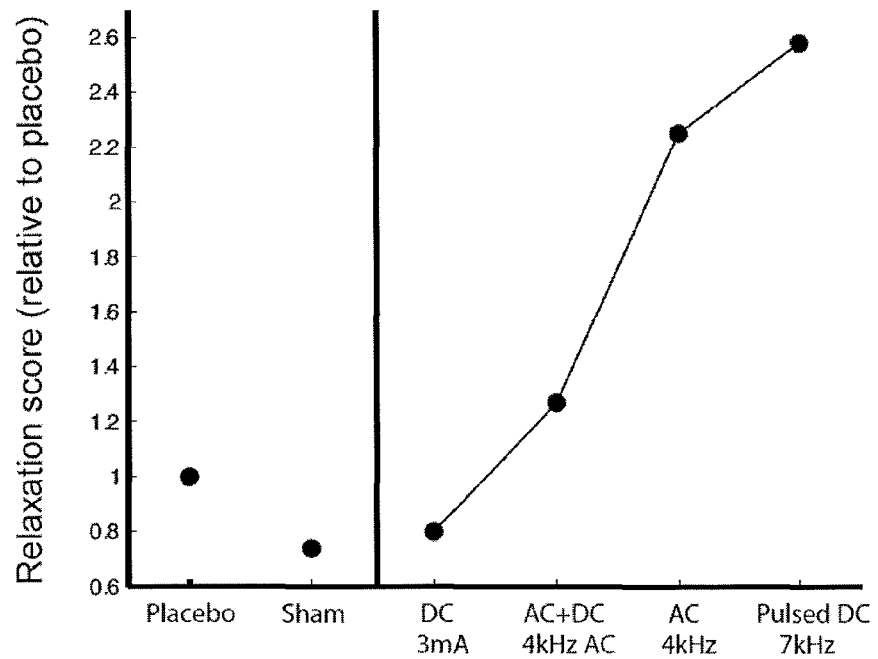
FIG. 16 illustrates subjects' level of relaxation during TES using placebo condition, sham stimulation, and various forms alternating and direct current TES using configuration 3 described herein.

FIG. 16 illustrates high-intensity TES stimulation on subjects' level of relaxation with electrodes positioned according to Configuration 3. In this example, subjects received TES, placebo, or sham stimulation and were assessed for subjective feelings of relaxation with electrodes positioned according to configuration 3. Scores are shown in FIG. 16 and were normalized so that the placebo condition was equivalent to a relaxation score of 1. Sham stimulation caused a slight decrease in average relaxation scores among subjects. Direct current stimulation at 3 mA also did not cause an increase in relaxation. In contrast, alternating current stimulation (4 kHz square wave biphasic; inTENSity unit, Current Solutions LLC, Austin Tex.; current intensity was controlled by subjects up to a maximum of 10 mA) in isolation or combined with direct current caused increased relaxation. Pulsed direct current stimulation induced the largest increases in relaxation (Idrostar system, STD Pharmaceuticals, Inc, Hereford England; 7 kHz pulsing, about 42% duty cycle, current intensity was controlled by subjects up to a maximum of 10 mA). A TES system with electrodes positioned according to configuration 3 provides feelings of enhanced relaxation in subjects when configured with appropriate TES protocols.

Figure 17:
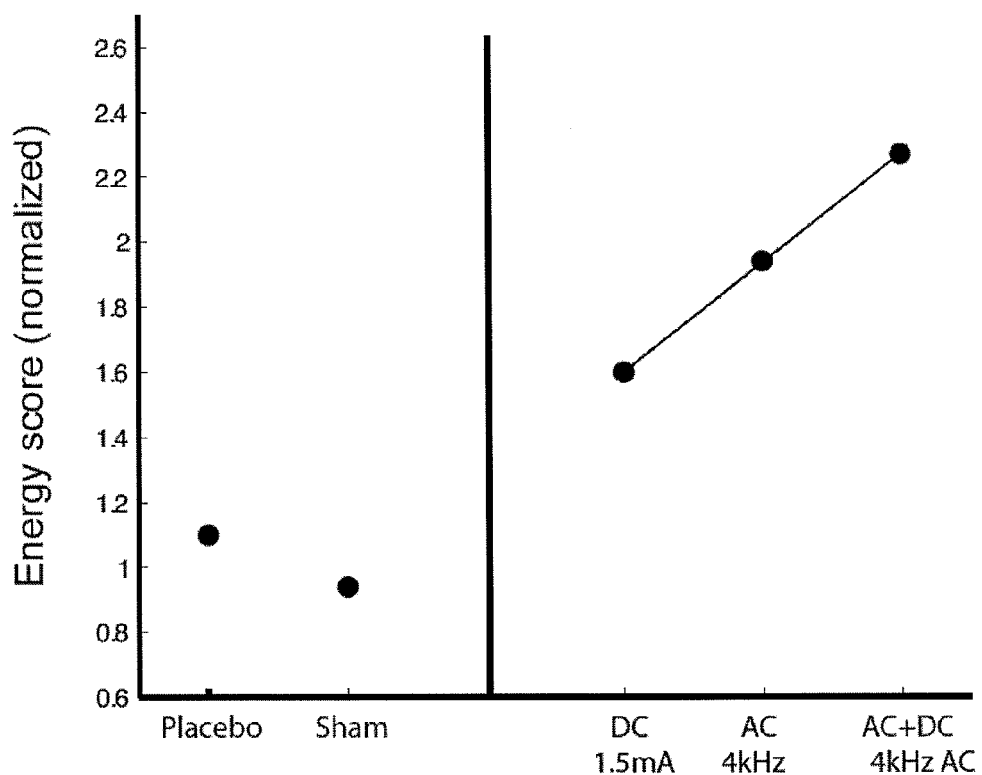
FIG. 17 illustrates subjects' level of relaxation during TES using placebo condition, sham stimulation, and various forms alternating and direct current TES using configuration 3, described herein.

FIG. 17 illustrates the effects of a TES protocol in configuration 2 on subjects' feelings of energy. In this example, subjects received TES, placebo, or sham stimulation and were assessed for subjective feelings of energy with electrodes positioned according to configuration 2. Scores are shown in FIG. 17. Sham stimulation caused a slight decrease in average relaxation scores among subjects relative to placebo. Direct current stimulation at 1.5 mA caused a moderate increase in feelings of energy. Alternating current stimulation (4 kHz square wave biphasic; inTENSity unit, Current Solutions LLC, Austin Tex.; current intensity was controlled by subjects up to a maximum of 10 mA) in isolation or combined with direct current (1.5 mA) caused larger enhancements in subjects' feelings of energy. A TES system with electrodes positioned according to configuration 2 provides feelings of enhanced energy in subjects when configured with appropriate TES protocols.

Figures 18A, 18B:
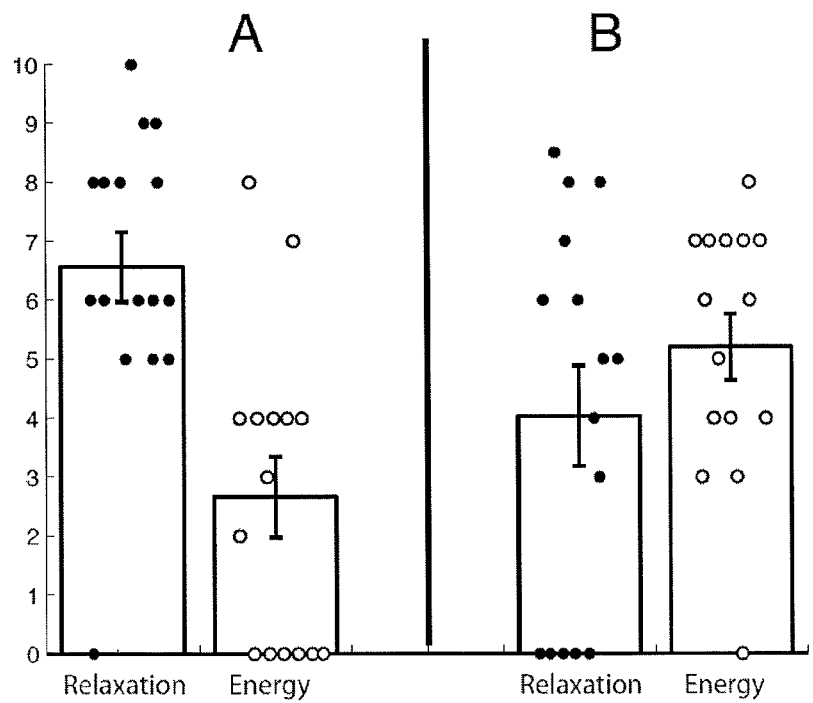
FIGS. 18A and 18B illustrate subjects' energy during TES using placebo condition, sham stimulation, and various forms alternating and direct current TES using configuration 2, described herein.

FIGS. 18A and 18B illustrate the effects of configuration 2 and configuration 3 on a subject's feelings of relaxation and energy. In this example, subjects received pulsed direct current stimulation from an Idrostar system STD Pharmaceuticals, Inc, Hereford England; 7 kHz pulsing, about 42% duty cycle, current intensity was controlled by subjects up to a maximum of 10 mA). In a first session, subjects had electrodes positioned according to configuration 3 and reported subjective feelings of relaxation and energy after 10 minutes of electrical stimulation. Subjects reported high levels of relaxation but low levels of energy on a customized 10-point scale (FIG. 18A). After a 10 minute "washout" period, subjects' electrodes were shifted to positions for configuration 2 and pulsed direct current stimulation began again. After this second 10 minute electrical stimulation session, subjects reported increased energy and lower relaxation scores. These results indicate a robust and reversible neuromodulatory effects from configuration 2 for increasing energy and configuration 3 for increasing relaxation.

Based on experiments such as this one and others, numerous other (negative) experiments using other electrode positions (configurations), position has been found to be extremely important to evoking a particular cognitive effect.

Figure 19A:
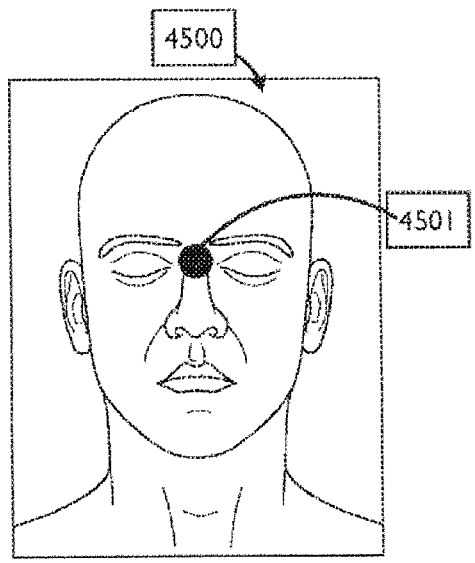
FIGS. 19A and 19B show exemplary electrode positions for a configuration 4; the first electrode position is shown in FIG. 19A and the second electrode position in 19B.
Figure 19B:
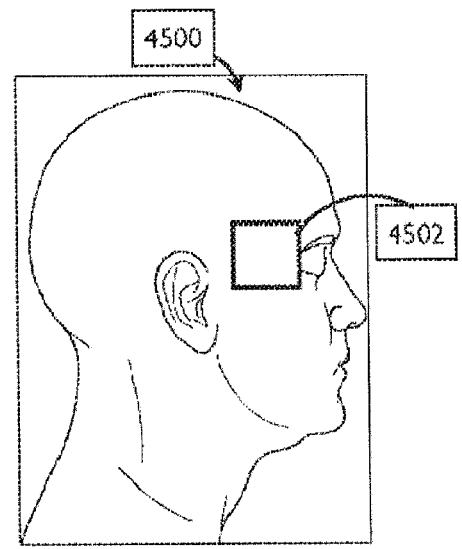

Other configurations (e.g., placement locations) of electrodes may have different effects, and have been exampled. For example FIGS. 19A and 19B illustrate one example of a configuration ("configuration 4") in which an electrode is positioned on the bridge of the subject's nose and a second electrode is positioned on the head greater than a few inches from the first electrode (e.g., on the subject's forehead or temple. Configuration 4 electrode placement is relatively easy for a user to do themselves. Systems and methods for TES using configuration 4 electrically couple a first electrode (e.g., anode) to the subject between the eyes at the bridge of the nose. FIG. 19A shows model subject 4500 with a round anode electrode placed between the eyes on the bridge of the nose. In a preferred embodiment, the anode electrode is less than 1" across and flexible in order to conform to the curvature of the area near the bridge of the nose of a subject. The anode electrode may be round, elliptical, square, rectangular, or an irregular shape configured for ease of placement on the curved areas of the nose. In a preferred embodiment, a second electrode (e.g., cathode) is located at a site selected from the list including, but not limited to: temple 4502 (as shown in FIG. 19B), forehead, neck, mastoid, shoulder, arm, or elsewhere on the face, head, neck, or body below the neck. A second electrode can be placed on either side of the body. In some embodiments, multiple cathode electrodes can be used.

The forehead electrode can be easily affixed using a mirrored surface or smartphone (or tablet) camera, and the neck cathode positioning does not need to be precise. In at least some instances, Configuration 4 requires relatively high currents, e.g. TES (tDCS) of at least about 3 mA, to achieve desired cognitive effects. Electrodes placed on the head according to configuration 4 can be used as part of a TES system for delivering electrical stimulation to induce a change in cognitive state for enhancing a state of calm in a subject, enhancing drowsiness so that it is easier to fall asleep, or inducing sleep. Configuration 4 may be used as part of a TES system configured to deliver one or more of: direct currents with maximum intensity greater than 3 mA; pulsed direct currents with maximum intensity greater than 5 mA; or alternating currents with maximum intensity greater than +/−5 mA.

Figure 20:
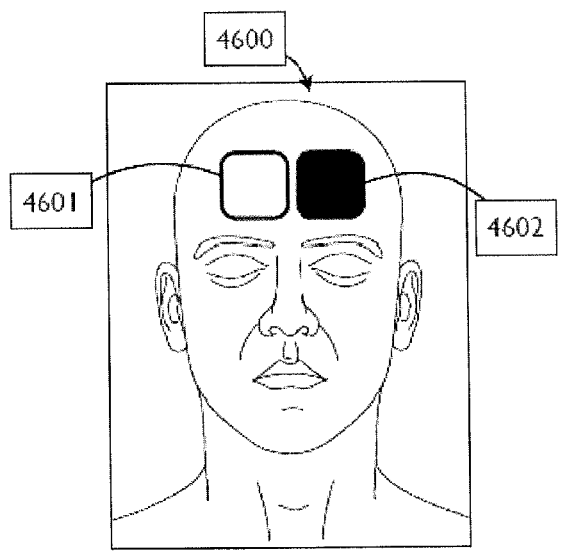
FIG. 20A shows an example of a configuration 5.
FIG. 20B shows an example of a configuration 6.

FIG. 20A illustrates another configuration, referred to herein (for convenience) as "configuration 5". In this example, the use of configuration 5 for TES as described herein may result in an induced cognitive effect including, but not limited to: increased energy; enhanced focus; improved mood; and feelings of pleasantness. Configuration 5 may cause neuromodulation by targeting one or more of: the brain; one or more cranial nerves; one or more nerves; and one or more nerve ganglia. As shown in FIG. 20A, configuration 5 electrode placement is relatively easy for a user to do themselves, by attaching both the first and second electrodes to the subject's forehead. FIG. 20A shows model subject 4600 with rounded square electrodes placed adjoining each other or within 2 cm of each other on the forehead. A first electrode (e.g., anode) 4602 is positioned above the subject's left eye and a second electrode (e.g., cathode) 4601 is positioned above the subject's right eye. In some embodiments, multiple isoelectric electrodes can replace a single anode or cathode.

Interestingly, a similar placement nearby these regions is ineffective; positioning with a small electrode more superior and lateral on the subject's left forehead and second electrode (e.g., oval shaped electrode) above the subject's right eyebrow does not result in this induced cognitive effect, showing the importance of configuration (placement) of electrodes. The forehead electrodes in configuration 5 can be affixed by the subject himself or herself using a mirrored surface or camera (e.g., smartphone or tablet camera) to guide them. Configuration 5 may be robustly result in modification of a cognitive state by using high currents (e.g. TES stimulation of at least about 3 mA) as described herein to achieve desired cognitive effects, requiring electrodes and/or stimulation protocols to be selected for reduced pain and irritation in a user.

Figure 20B:
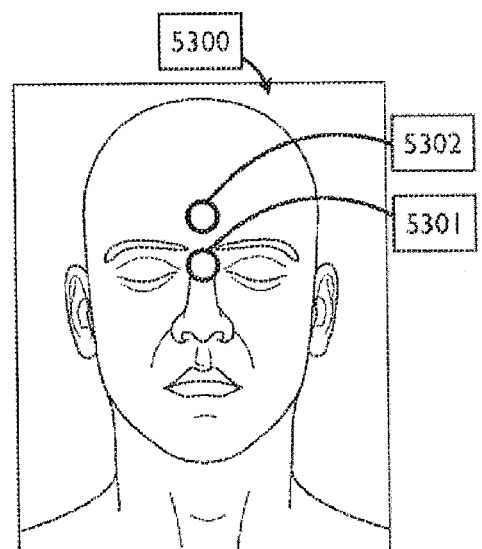

FIG. 20B illustrates another example of a configuration, referred to herein as configuration 6. In configuration 6, the first electrode (e.g., anode) is placed over the bridge of the nose (e.g., the nasion region) and a second electrode (e.g., a small, round cathode) is positioned right above it, e.g., nearby within a few cm. The cognitive effects evoked using this configuration may be bimodal in terms of energy and sleepiness depending on waveform delivered.

Subjects treated with TES using configuration 6 may experience different forms of neuromodulation with distinct cognitive effects depending on the waveform and intensity delivered. Configuration 6 electrically couples an electrode to a subject between the eyes at the bridge of the nose ('nasal' electrode) and a second electrode near the midline on the forehead ('forehead' electrode), superior to the nasal electrode. The nasal electrode may be about 1" or less across and flexible in order to conform to the curvature of the area near the bridge of the nose of a subject (e.g. 1" diameter PALS platinum electrodes from Axelgaard Manufacturing Co., Ltd.; Fallbrook, Calif.). The forehead electrode may be close to (i.e. about 1 cm) and directly above (superior to) the nasal electrode. The forehead electrode may also be a 1" flexible round electrode or may be selected to have a different size, shape, and/or composition. Generally, electrodes less than about 2" in diameter are preferable to be used as the forehead electrode in configuration 6 in order to avoid side effects. A forehead electrode may be positioned slightly lateral to the left or right of the midline on the forehead and/or further superior on the forehead.

FIG. 20B shows model subject 5300 with electrodes placed according to configuration 6. Either of the electrodes can be configured as the anode or cathode. However, preferred embodiments are configured with round nasal electrode 5301 as the anode and round forehead electrode 5302 affixed to the lower medial forehead area directly above nasal electrode 5301. In some embodiments, multiple isoelectric electrodes can replace a single anode or cathode. In FIG. 20B, the nasal electrode is an anode and the forehead electrode is a cathode.

Systems and methods with this electrode configuration deliver different electrical stimulation waveforms to achieve distinct cognitive effects, as described below. For example, a first waveform delivers TES using an alternating transcranial electrical stimulation current at a frequency between 3 kHz and 5 kHz (100% duty cycle, no direct current offset) at an intensity greater than 2 mA (preferably greater than 5 mA) and induces neuromodulation in a subject with cognitive effects including, but not limited to: increased drowsiness; increased desire to sleep: induction of sleep; induction of a relaxed state of mind; and induction of a calm state of mind. In alternative embodiments, shorter duty cycles and a DC offset less than about 2 mA is used to enhance the cognitive effects achieved from this waveform. One side effect reported for TES using this type of waveform is mild sinus pressure.

A second waveform delivers TES using an alternating transcranial electrical stimulation current at a frequency less than 3 kHz (100% duty cycle, no direct current offset; preferably between 300 Hz and 1 kHz) at an intensity greater than 1 mA (preferably greater than 2 mA) induces neuromodulation with cognitive effects including, but not limited to: increased energy and enhanced wakefulness. One side effect reported for TES using this type of waveform is tingliness or itching in the skin of the face and scalp, presumably due to trigeminal nerve stimulation. Lower frequencies of alternating current stimulation are associated with higher skin impedance and more substantial side effects that can be disruptive to the experience of the induced cognitive effect in the user.

By alternating, interleaving, and/or combining the first and second alternating current transcranial electrical stimulation waveforms described above, a subject can achieve titrated levels of energy and relaxation, as well as beneficial and enjoyable experiences wherein a subject's levels of energy and relaxation vary over time. Electrode positioning for configuration 6 is important to get both effects with minimal undesirable side effects. Embodiments wherein the electrodes are in close proximity (i.e. nearest electrode edges about 1 cm or less from each other) minimize resistance in the stimulation circuit, improving energy efficiency of a TES system. Energy efficiency is a beneficial quality of portable and battery-powered TES systems. Another benefit of placing the electrodes on the nasal region and directly above on the lower medial portion of the forehead is to reduce undesirable side effects. If one of the electrodes is more lateral and near the eyelid area (e.g. temples), irritating eye twitchiness can occur with the 400 Hz alternating current stimulation protocol and a calming/sleepiness effect can be mitigated by facial tingling (presumably due to trigeminal nerve activation) with the 4000 Hz alternating current stimulation protocol.

Another beneficial optional feature using configuration 6 is to ramp the current intensity up and/or down quickly for waveforms to enhance either form of neuromodulation due to the pleasurability and interesting sensory quality of the neuromodulatory effects and sensory side effects, as described in greater detail above.

A system for TES using configurations such as configuration 6 may include a set of eyeglasses or other worn band, assembly, or cap that holds the electrodes in place. For instance, sunglasses or 'shutter shades' can be used to hold a nasal electrode and forehead electrode firmly in place.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all subranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of modifying a subject's cognitive state, the method comprising:
    activating a transdermal electrical stimulation (TES) applicator to deliver a pulsed, asymmetric, biphasic transdermal electrical stimulation having a frequency of 750 Hz or greater and an intensity of greater than 3 mA between a first electrode positioned on the subject's skin on a temple or forehead region on a first side of the subject's body and a second electrode on the subject's skin on either the mastoid region of the first side of the subject's body or on the subject's neck; and
    modifying the subject's cognitive state by applying the biphasic transdermal electrical stimulation between the first and second electrodes for 10 seconds or longer.

2. The method of claim 1, wherein modifying the subject's cognitive state by applying the biphasic transdermal electrical stimulation for 10 seconds or longer comprises applying intervals of the biphasic transdermal stimulation having a frequency of 750 Hz or greater and an intensity of greater than 3 mA during the 10 seconds or longer.

3. The method of claim 1, further comprising wearing the TES applicator on the subject's head or neck.

4. The method of claim 1, wherein activating the TES applicator to deliver the pulsed, asymmetric, biphasic transdermal electrical stimulation further comprises, applying a capacitive discharge current to the electrodes to oppose any capacitance built-up during the delivery of the biphasic transdermal electrical stimulation.

5. The method of claim 1, wherein activating the TES applicator to deliver the pulsed, asymmetric, biphasic transdermal electrical stimulation further comprises, applying a capacitive discharge current periodically within each cycle of the biphasic transdermal electrical stimulation to oppose any capacitance built-up during the delivery of the biphasic transdermal electrical stimulation.

6. The method of claim 1, wherein activating the TES applicator comprises activating the TES applicator to deliver the biphasic transdermal electrical stimulation having a duty cycle of greater than 10 percent.

7. The method of claim 1, wherein modifying the subject's cognitive state comprises enhancing attention, alertness, or mental focus, and wherein the second electrode is positioned on the subject's skin on the mastoid region of the first side of the subject's body.

8. The method of claim 1, wherein modifying the subject's cognitive state comprises enhancing a calm or relaxed mental state, and wherein the second electrode is positioned on the back of the subject's neck.

9. The method of claim 1, wherein activating the TES applicator comprises wirelessly triggering activation of the TES applicator.

10. The method of claim 1, further comprising varying the applied biphasic transdermal electrical stimulation while the biphasic transdermal stimulation is applied.

11. The method of claim 1, further comprising varying the applied biphasic transdermal electrical stimulation while keeping the biphasic transdermal electrical stimulation within a duty cycle of greater than 10 percent, the frequency of 750 Hz or greater, and the intensity of greater than 3 mA.

12. The method of claim 1, further comprising ramping the biphasic transdermal electrical stimulation during the application by modifying one or more of the intensity, frequency and duty cycle from an initial state and then restoring the one or more of the intensity, frequency and duty cycle back to the initial state.

13. A method of modifying a subject's cognitive state, the method comprising:
    positioning a first electrode on the subject's skin on a temple or forehead region on a first side of the subject's body;
    positioning an electrode on the subject's skin on either the mastoid region of the first side of the subject's body or on the subject's neck;
    activating a wearable transdermal electrical stimulation (TES) applicator to deliver a pulsed, asymmetric, biphasic transdermal electrical stimulation having a frequency of 750 Hz or greater and an intensity of greater than 3 mA between the first and second electrodes; and
    modifying the subject's cognitive state by applying the biphasic transdermal electrical stimulation between the first and second electrodes for 10 seconds or longer.

14. A wearable transdermal electrical stimulation (TES) applicator device for modifying a subject's cognitive state, the device comprising:
    a body;
    a first connector configured to connect to a first electrode;
    a second connector configured to connect to a second electrode; and
    a TES control module at least partially within the body and comprising a processor, a timer and a waveform generator, wherein the TES control module is adapted to deliver a TES waveform between electrodes connected to the first and second connectors, the TES waveform comprising a pulsed, asymmetric, biphasic electrical stimulation signal having a frequency of 750 Hz or greater, a duty cycle of greater than 10 percent, and an intensity of greater than 3 mA;
    wherein the TES control module is configured to modulate a parameter of the TES waveform based on received subject input.

15. The device of claim 14, wherein the TES control module comprises a user interface configured to allow the user to adjust one or more TES waveform parameter to modify the effective intensity of the TES waveform during delivery of the TES waveform.

16. The device of claim 14, wherein the first connector comprises a snap configured to connect to an electrode assembly.

17. The device of claim 14, wherein the TES control module is configured to deliver the TES waveform for greater than 10 seconds.

18. The device of claim 14, wherein the TES control module is configured to deliver the TES waveform for 10 second or longer comprises applying intervals of the biphasic transdermal stimulation having a frequency of 750 Hz or greater and an intensity of greater than 3 mA during the 10 seconds or longer.

19. The device of claim 14, wherein the second connector comprises an elongate wire.

20. The device of claim 14, further comprising a wireless receiver coupled to the TES control module.

21. The device of claim 14, wherein the first connector is on an outer surface of the body.

22. The device of claim 14, further comprising an electrode assembly comprising the first and second electrodes.

23. The device of claim 14, further comprising a power source.

24. The device of claim 14, further comprising a high-voltage power source having a voltage of greater than 40 V.

25. The device of claim 14, further comprising a manual control on the body coupled to the TES control module.

26. The device of claim 14, further comprising a capacitive discharge circuit, wherein the TES control module is configured to trigger the capacitive discharge circuit to apply a current opposing capacitance on the electrodes during the delivery of the pulsed, asymmetric, biphasic electrical stimulation.

27. The device of claim 14, wherein the TES control module is further adapted to deliver the pulsed, asymmetric, biphasic electrical stimulation signal having the frequency of 750 Hz or greater, the duty cycle of greater than 10 percent, and the intensity of greater than 3 mA, wherein the stimulation is not charge balanced.

28. A wearable transdermal electrical stimulation (TES) applicator device for modifying a subject's cognitive state, the device comprising:
   a body;
   a first connector on the body configured to connect to a first electrode;
   a second connector on the body configured to connect to a second electrode; and
   a TES control module at least partially within the body, the TES control module including a power source, a processor, a timer, and a waveform generator, wherein the TES control module is adapted to deliver a pulsed, asymmetric, biphasic electrical stimulation signal between electrodes connected to the first and second connectors, having a frequency of 750 Hz or greater, a duty cycle of greater than 10 percent, and an intensity of greater than 3 mA, wherein the stimulation is not charge balanced; and
   a wireless receiver connected to the TES control module;
   wherein the wearable TES applicator weighs less than 50 grams and is configured to modulate a parameter of the TES waveform based on received subject input.

* * * * *